US009981913B2

(12) United States Patent
Mohan

(10) Patent No.: US 9,981,913 B2
(45) Date of Patent: May 29, 2018

(54) LIVER X RECEPTOR (LXR) MODULATORS

(71) Applicant: Ralexar Therapeutics, Inc., Malvern, PA (US)

(72) Inventor: Raju Mohan, Malvern, PA (US)

(73) Assignee: Ralexar Therapeutics, Inc., Malvern, PA (US)

( * ) Notice: Subject to any disclaimer, the term of this patent is extended or adjusted under 35 U.S.C. 154(b) by 0 days. days.

(21) Appl. No.: 14/916,292

(22) PCT Filed: Sep. 4, 2014

(86) PCT No.: PCT/US2014/054065
§ 371 (c)(1),
(2) Date: Mar. 3, 2016

(87) PCT Pub. No.: WO2015/035027
PCT Pub. Date: Mar. 12, 2015

(65) Prior Publication Data
US 2016/0214943 A1    Jul. 28, 2016

Related U.S. Application Data

(60) Provisional application No. 61/873,746, filed on Sep. 4, 2013.

(51) Int. Cl.
| | | |
|---|---|---|
| *C07D 231/12* | (2006.01) | |
| *C07D 413/14* | (2006.01) | |
| *C07D 231/14* | (2006.01) | |
| *C07D 233/64* | (2006.01) | |
| *C07D 233/90* | (2006.01) | |
| *C07D 409/04* | (2006.01) | |

(52) U.S. Cl.
CPC ......... *C07D 231/12* (2013.01); *C07D 231/14* (2013.01); *C07D 233/64* (2013.01); *C07D 233/90* (2013.01); *C07D 409/04* (2013.01); *C07D 413/14* (2013.01)

(58) Field of Classification Search
CPC .. C07D 231/12; C07D 413/14; C07D 231/14; C07D 233/64; C07D 233/90; C07D 409/04
See application file for complete search history.

(56) References Cited

U.S. PATENT DOCUMENTS

| 8,008,303 | B2 | 8/2011 | Wheelhouse et al. |
|---|---|---|---|
| 8,987,318 | B2 | 3/2015 | Mohan |
| 2005/0038248 | A1 | 2/2005 | Henderson et al. |
| 2005/0080111 | A1 | 4/2005 | Bayne et al. |
| 2006/0030612 | A1 | 2/2006 | Steffan et al. |
| 2006/0261319 | A1 | 11/2006 | Gaskins |
| 2006/0270628 | A1* | 11/2006 | Das .................. C07D 403/10 514/63 |
| 2010/0069367 | A1 | 3/2010 | Boren |
| 2010/0075964 | A1 | 3/2010 | Busch |
| 2010/0168093 | A1 | 7/2010 | Pericas-Brondo et al. |
| 2010/0331295 | A1 | 12/2010 | Busch |
| 2011/0294784 | A1 | 12/2011 | Asberom |
| 2012/0040977 | A1 | 2/2012 | Li et al. |
| 2015/0152094 | A1 | 6/2015 | Mohan |
| 2016/0221956 | A1 | 8/2016 | Mohan |

FOREIGN PATENT DOCUMENTS

| CN | 101248048 | 8/2008 |
|---|---|---|
| CN | 102584705 | 7/2012 |
| WO | WO 2002/024632 | 3/2002 |
| WO | WO 2003/099769 | 12/2003 |
| WO | WO 2003/099775 | 12/2003 |
| WO | WO 2004/058717 | 7/2004 |
| WO | WO 2005/023782 | 3/2005 |
| WO | WO 2005/113499 | 12/2005 |
| WO | WO 2006/003923 | 1/2006 |
| WO | WO 2006/069155 | 6/2006 |
| WO | WO 2006/109633 | 10/2006 |
| WO | WO 2007/002559 | 1/2007 |
| WO | WO 2007/002563 | 1/2007 |
| WO | WO 2007/034279 | 3/2007 |
| WO | WO 2007/092065 | 8/2007 |
| WO | WO 2008/049047 | 4/2008 |
| WO | WO 2008/104077 | 9/2008 |
| WO | WO 2009/011850 | 1/2009 |
| WO | WO 2009/020683 | 2/2009 |
| WO | WO 2009/021868 | 2/2009 |
| WO | WO 2009/086123 | 7/2009 |
| WO | WO 2009/086138 | 7/2009 |
| WO | WO 2009/140089 | 11/2009 |
| WO | WO 2009/150109 | 12/2009 |
| WO | WO 2010/054229 | 5/2010 |
| WO | WO 2010/059627 | 5/2010 |
| WO | WO 2010/096170 | 8/2010 |
| WO | WO 2010/138598 | 12/2010 |

(Continued)

OTHER PUBLICATIONS

Boren et al., 2008, caplus an 2008:736475.*
Chang et al., Molecular Endrocrinology, vol. 22, Issue 11, 2008, 12 pages.*
CAS RN 1005621-87-3, STN Entry Date Feb. 28, 2008, 1 page.
CAS RN 1005664-76-5, STN Entry Date Feb. 28, 2008, 1 page.
CAS RN 1005700-88-8, STN Entry Date Feb. 28, 2008, 1 page.
CAS RN 1199770-53-0, STN Entry Date Dec. 31, 2009, 1 page.
CAS RN 1199771-22-6, STN Entry Date Dec. 31, 2009, 1 page.
CAS RN 263160-65-2, STN Entry Date Apr. 26, 2000, 1 page.
CAS RN 292826-84-7, STN Entry Date Oct. 5, 2000, 1 page.
CAS RN 300589-02-0, STN Entry Date Oct. 31, 2000, 1 page.
CAS RN 957264-80-1, STN Entry Date Dec. 10, 2007, 1 page.
CAS RN 957493-13-9, STN Entry Date Dec. 11, 2007, 1 page.
CAS RN 957947-23-8, STN Entry Date Dec. 13, 2007, 1 page.
CAS RN 959009-61-1, STN Entry Date Dec. 20, 2007, 1 page.

(Continued)

*Primary Examiner* — Sun Jae Yoo
(74) *Attorney, Agent, or Firm* — Fish & Richardson P.C.

(57) ABSTRACT

Described herein are liver X receptor (LXR) modulators and methods of utilizing LXR modulators in the treatment of dermal diseases, disorders or conditions. Also described herein are pharmaceutical compositions containing such compounds.

14 Claims, No Drawings

(56) References Cited

FOREIGN PATENT DOCUMENTS

| WO | WO 2011/045415 | 4/2011 |
|---|---|---|
| WO | WO 2011/046733 | 4/2011 |
| WO | WO 2012/019093 | 2/2012 |
| WO | WO 2012/020820 | 2/2012 |
| WO | WO 2012/027710 | 3/2012 |
| WO | WO 2012/135082 | 10/2012 |
| WO | WO 2013/130892 | 9/2013 |
| WO | WO2013130892 A1 | 9/2013 |
| WO | WO 2014/028461 | 2/2014 |
| WO | WO 2015/035015 | 3/2015 |

OTHER PUBLICATIONS

CAS RN 959583-29-0, STN Entry Date Dec. 26, 2007, 1 page.
Chang et al., "Liver X Receptor Is a Therapeutic Target for Photoaging and Chronological Skin Aging," Mol. Endocrinol., 2008, 22(11):2407-2419.
Chen, H. -S., et al, "Synthesis of 2-Pyrazolyl-5-substituted-1,3,4-oxadiazoles and Their Biological Activities", Chemical Journal of Chinese Universities, 2000, 21(10), 1520-1523 [English Abstract].
Dai et al, "Liver X receptor β protects dopaminergic neurons in a mouse model of Parkinson disease," PNAS, 2012, 109:13112-13117.
Extended European Search Report in European Application No. 13754329.4, dated Oct. 12, 2015, 6 pages.
Extended European Search Report in European Application No. 14841483.2, dated Jan. 9, 2017, 6 pages.
Finn et al., "Discovery of a Potent and Selective Series of Pyrazole Bacterial Methionyl-Trna Synthetase Inhibitors," Bioorganic & Medicinal Chemistry Letters, Jan. 2003, 13(13):2231-2234.
Fluhr et al., "Topical Liver X Receptor Activators Accelerate Postnatal Acidification of Stratum Corneum and Improve Function in the Neonate," J. Investigative Dermatology, Dec. 2005, 125:1206-1214.
Fowler et al., "Liver X receptor activators display anti-inflammatory activity in irritant and allergic contact dermatitis models: liver-X-receptor-specific inhibition of inflammation and primary cytokine production," J. Invest. Dermatol., Feb. 2003, 120:246-255.
GenBank® accession No. AAM90897, GI: 22087254, Cholesterol and bile acids regulate xenosensor signaling in drug-mediated induction of cytochromes P450, dated Aug. 12, 2002, 1 page.
GenBank® accession No. AAY43056 GI: 66220403, Sus scrofa nuclear orphan receptor LXR-alpha mRNA, dated May 22, 2005, 1 page.
GenBank® accession No. P55055, GI: 296439251, NER, a new member of the gene family encoding the human steroid hormone nuclear receptor, dated Sep. 5, 2012, 7 pages.
GenBank® accession No. Q13133, GI: 23503089, LXR, a nuclear receptor that defines a distinct retinoid response pathway, dated Sep. 5, 2012, 6 pages.
GenBank® accession No. Q5BIS6, GI: 116242681, Characterization of 954 bovine full-CDS cDNA sequences, dated Nov. 28, 2012, 3 pages.
GenBank® accession No. Q5E9B6, GI: 75060925, Characterization of 954 bovine full-CDS cDNA sequences, dated Sep. 5, 2012, 3 pages.
GenBank® accession No. Q60644, GI: 10720386, Isolation of proteins that interact specifically with the retinoid X receptor: two novel orphan receptors, dated Sep. 5, 2012, 4 pages.
GenBank® accession No. Q62685, GI: 11465384, A novel orphan receptor specific for a subset of thyroid hormone-responsive elements and its interaction with the retinoid/thyroid hormone receptor subfamily, dated Oct. 3, 2012, 3 pages.
GenBank® accession No. Q62755, GI: 13124670, OR-1, a member of the nuclear receptor superfamily that interacts with the 9-cis-retinoic acid receptor, dated Sep. 5, 2012, 3 pages.
GenBank® accession No. Q9Z0Y9, GI: 341942229, LXRalpha functions as a cAMP-responsive transcriptional regulator of gene expression, dated Sep. 5, 2012, 5 pages.

Geyeregger et al., "Liver X receptors in cardiovascular and metabolic disease," Cell. Mol. Life Sci., Mar. 2006, 63:524-539.
Hatano et al., "Murine atopic dermatitis responds to peroxisome proliferator-activated receptor α, β/δ(but not γ), and liver-X-receptor activators," The Journal of Allergy and Clinical Immunology, 2010, 125(1):160-169.
Huynh, T., et al, "Optimization of pyrazole inhibitors of Coactivator Associated Arginine Methyltransferase 1 (CARM1)", Bioorganic & Medicinal Chemistry Letters, 2009, 19(11), 2924-7.
International Preliminary Report on Patentability in International Application No. PCT/US2013/028438, dated Sep. 2, 2014, 8 pages.
International Preliminary Report on Patentability in International Application No. PCT/US2014/054065, dated Mar. 17, 2016, 15 pages.
International Preliminary Report on Patentability in International Application No. PCT/US2014/54043, dated Mar. 8, 2016, 9 pages.
International Search Report and the Written Opinion in International Application No. PCT/US2014/54043, dated Nov. 25, 2014, 16 pages.
International Search Report in International Application No. PCT/US2013/028438, dated Jun. 18, 2013, 4 pages.
Ishida, "Regulated expression of apolipoprotein E by human retinal pigment epithelial cells," Journal of Lipid Research, 2004, 45:263-271.
Koldamova et al., "The liver X receptor ligand T0901317 decreases amyloid beta production in vitro and in a mouse model of Alzheimer's disease," J. Biol. Chem., Feb. 2005, 280:4079-88.
Kumar et al., "Liver X receptor expression in human melanocytes, does it have a role in the pathogenesis of vitiligo?," Experimental Dermatology, 2009, 19:61-64.
Lee et al., "Liver X Receptor Activation Inhibits Melanogenesis through the Acceleration of ERK-Mediated MITF Degradation," J. Invest Dermatol., Dec. 6, 2012, 133:1063-1071.
Lefterov et al., "Expression profiling in APP23 mouse brain: inhibition of Aβ amyloidosis and inflammation in response to LXR agonist treatment," Mol. Neurodegeneration, 2007, 2:20.
Madison, "Barrier Function of the Skin: "La Raison d'Etre" of the Epidermis," J. Investigative Dermatology, Aug. 2003, 121(2):231-241.
Man et al., "Basis for Improved Permeability Barrier Homeostasis Induced by PPAR and LXR Activators: Liposensors Stimulate Lipid Synthesis, Lamellar Body Secretion, and Post-Secretory Lipid Processing," J. Investigative Dermatology, 2006, 126:386-392.
Martres et al., "The Discovery of equipotent PPARalpha/gamma dual activators," Bioorganic & Medicinal Chemistry Letters, Dec. 1, 2008, 18(23):6251-6254.
Mauch et al., "CNS Synaptogenesis Promoted by Glia-Derived Cholesterol," Science, Nov. 2001, 294:1354-7.
Office Action in Chinese Application No. 201380018482.7, dated Apr. 11, 2016, 15 pages, with English translation.
Office Action in Chinese Application No. 201380018482.7, dated Aug. 18, 2015, 24 pages, with English translation.
Office Action in Japanese Application No. 2014-560060, dated Aug. 16, 2016, 13 pages, with English translation.
Pencheva et al., "Convergent multi-miRNA targeting of ApoE drives LRP1/LRP8-dependent melanoma metastasis and angiogenesis," Cell, Nov. 21, 2012, 151(5):1068-1082.
Pietrzak et al., "Lipid Disturbances in Psoriasis: An Update," Mediators of Inflammation, 2010, 13 pages.
Reply to European Search Report in European Application No. 13754329.4, dated Apr. 29, 2016, 17 pages.
Riddell et al., "The LXR agonist TO901317 selectively lowers hippocampal Abeta42 and improves memory in the Tg2576 mouse model of Alzheimer's disease," Mol. Cell Neurosci., Apr. 2007, 34:621-8.
Russell et al., "Characterization of liver X receptor expression and function in human skin and the pilosebaceous unit," Experimental Dermatology, 2007, 16:844-852.
Safety Pharmacology of LXR Agonists, 2 pages.
Schmuth et al., "Thematic review series: skin lipids. Peroxisome proliferator-activated receptors and liver X receptors in epidermal biology," Journal of Lipid Research, Mar. 2008, 49:499-509.

(56) References Cited

OTHER PUBLICATIONS

Sene et al., "Impaired cholesterol efflux in senescent macrophages promotes age-related macular degeneration," Cell Metabolism, Apr. 2013, 17:549-561.

Supplementary Partial European Search Report in European Application No. 14842802.2, dated Dec. 20, 2016, 7 pages.

Therrien, E., et al, "1,2-Diamines as inhibitors of co-activator associated arginine methyltransferase 1 (CARM1)", Bioorganic & Medicinal Chemistry Letters, 2009, 19(23), 6725-6732.

Tice et al., "The Medical Chemistry of Liver X Receptor (LXR) Modulators," J. Med Chem, May 15, 2014, retrieved from http://pubs.acs.org, 102 pages.

Viennois et al., "Targeting liver X receptors in human health: deadlock or promising trail?," Expert. Opin. Ther. Targets, 2011, 15(2):219-232.

Willy et al., "LXR, a nuclear receptor that defines a distinct retinoid response pathway," Genes & Development, May 1995, 9:1033-1045.

Written Opinion of the International Searching Authority in International Application No. PCT/US2013/028438, dated Jun. 18, 2013, 7 pages.

Zelcer and Tontonz, "Liver X receptors as integrators of metabolic and inflammatory signaling," J. Clinical Investigation, Mar. 2006, 116(3):607-614.

Zhang-Gandhi and Drew, "Liver X receptor and retinoid X receptor agonists inhibit inflammatory responses of microglia and astrocytes," J. Neuroimmunology, 2007, 183:50-59.

Transmittal of the International Search Report and the Written Opinion of the International Searching Authority for PCT/US2014/54065 dated Dec. 19, 2014, 23 pages.

\* cited by examiner

LIVER X RECEPTOR (LXR) MODULATORS

This application is a § 371 National Stage Application of PCT/US2014/054065, filed Sep. 4, 2014, which, in turn, claims the benefit of priority of U.S. Provisional Appl. No. 61/873,746, filed Sep. 4, 2013, each of which is incorporated herein by reference in its entirety.

BACKGROUND OF THE INVENTION

Liver X receptor (LXR) activation is associated with inflammation, hyperproliferative and/or disordered skin barrier differentiation. LXR activation also modulates multiple pathways underlying the etiology and pathology of skin aging.

SUMMARY OF THE INVENTION

Described herein are compounds of Formula I, IA, IB, II, IIA, IIB, III, IIIA, IIIB, IV, IVA, and IVB, pharmaceutical compositions that include such compounds, and methods of use thereof, for modulating LXR. In one aspect is the topical administration of at least one liver X receptor (LXR) modulator described herein to the skin of a mammal in the treatment of dermal diseases, disorders or conditions.

Provided herein are methods and compositions comprising topical administration of a liver X receptor (LXR) modulator for treatment of dermal diseases, disorders or conditions. Dermal diseases, disorders or conditions include, but are not limited to, skin aging, scarring, psoriasis, dermatitis, eczema, urticaria, rosacea, burns, acne, or any other condition described herein. Dermal diseases or disorders also refer to pigmentary disorders including but not limited to vitiligo. Dermal diseases also refer to skin malignancies and cancer, including melanoma and metastatic forms of these diseases.

In another embodiment is the use of a compound of Formula I, IA, IB, II, IIA, IIB, III, IIIA, IIIB, IV, IVA, and IVB, or a pharmaceutically acceptable salt, in the manufacture of a medicament for the treatment of a disease, disorder, or condition that would benefit from LXR modulation (such as any of the methods described herein). In another embodiment is the a compound of Formula I, IA, IB, II, IIA, IIB, III, IIIA, IIIB, IV, IVA, and IVB, or a pharmaceutically acceptable salt, for use in treatment of the treatment of a disease, disorder, or condition that would benefit from LXR modulation (such as any of the methods described herein).

Accordingly, provided herein are methods and compositions for maintenance of the dermal barrier and/or normalization of the dermal barrier and/or reducing injury to the dermal barrier and/or regeneration of the dermal barrier.

In one aspect provided herein is a method for treating the epidermis of a mammalian subject suffering from a perturbed epidermal barrier function, said method comprising topically administering to said epidermis a topical composition comprising an active ingredient that is an activator of the liver X receptor (LXR), said active ingredient being present in a concentration that is effective in enhancing barrier development.

In another aspect, provided herein is a method for treating the epidermis or mucous membrane of a terrestrial mammalian subject suffering from a condition of disturbed differentiation or excess proliferation, said method comprising topically administering to said epidermis or mucous membrane a topical composition comprising an active ingredient that is an activator of the liver X receptor (LXR), said active ingredient being present in a concentration that is effective in enhancing barrier development.

In some embodiments of the methods or compositions described above, the activator of LXR is a compound of Formula I, IA, IB, II, IIA, IIB, III, IIIA, IIIB, IV, IVA, and IVB as described herein. In some embodiments of the methods or compositions described above, the concentration of said active ingredient in the topical composition is from about 0.1 μM to 100 μM.

In one aspect is the use of a LXR modulator in the manufacture of a topical formulation for use in the treatment of a dermal disease, disorder or condition in a mammal. In one aspect is the use of a LXR modulator and a second therapeutic agent in the manufacture of a topical formulation for use in the treatment of a dermal disease, disorder or condition in a mammal.

In another aspect is a compound of Formula (I):

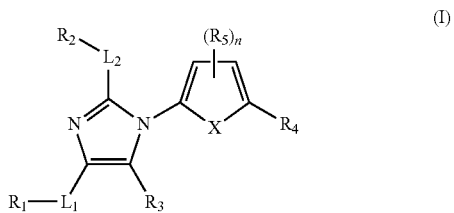

wherein:

X is —O—, —S—, or —C($R_6$)=C($R_6$)—;

$L_1$ and $L_2$ are each independently a bond, $C_1$-$C_6$alkyl, or $C_1$-$C_6$heteroalkyl; wherein $C_1$-$C_6$alkyl and $C_1$-$C_6$heteroalkyl are optionally substituted with at least one $R_7$;

$R_1$ is halogen, —$CF_3$, —$OR_8$, —N($R_8$)$_2$, —C(=O)$R_8$, —C(=O)O$R_8$, —C(=O)N($R_8$)$_2$, —C(=N—OH)$R_8$, —C(=S)N($R_8$)$_2$, $C_1$-$C_6$alkyl, $C_1$-$C_6$heteroalkyl, or optionally substituted $C_2$-$C_7$heterocycloalkyl;

$R_2$ is —C(=O)O$R_9$;

$R_3$ is hydrogen, halogen, $C_1$-$C_6$alkyl, or $C_1$-$C_6$haloalkyl;

$R_4$ is aryl or heteroaryl; wherein aryl and heteroaryl are substituted with at least one $R_{11}$;

each $R_5$ is independently halogen, $C_1$-$C_6$alkyl, or $C_1$-$C_6$haloalkyl;

each $R_6$ is independently hydrogen, halogen, $C_1$-$C_6$alkyl, or $C_1$-$C_6$haloalkyl;

each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

each $R_{11}$ is independently halogen, nitro, —$OR_{10}$, —N($R_{10}$)$_2$, —CN, —C(=O)$R_{10}$, —C(=O)O$R_{10}$, —C(=O)N($R_{10}$)$_2$, —N$R_{10}$C(=O)$R_{10}$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and n is 0-2;

or a pharmaceutically acceptable salt, pharmaceutically acceptable solvate, or pharmaceutically acceptable prodrug thereof.

In one embodiment is a compound of Formula I wherein $L_2$ is a bond. In another embodiment is a compound of Formula I wherein $L_2$ is $C_1$-$C_6$alkyl optionally substituted with at least one $R_7$. In another embodiment is a compound of Formula I wherein $L_2$ is —$CH_2$—. In another embodiment is a compound of Formula I wherein $L_2$ is $C_1$-$C_2$alkyl substituted with at least one $R_7$; and each $R_7$ is independently $C_1$-$C_6$alkyl, —$C_1$-$C_6$alkyl-aryl, or optionally substituted aryl. In a further embodiment is a compound of Formula I wherein $R_2$ is —C(=O)O$R_9$, and $R_9$ is $C_1$-$C_6$alkyl or $C_1$-$C_6$heteroalkyl. In a further embodiment is a compound of Formula I wherein $L_1$ is a bond. In a further embodiment is a compound of Formula I wherein $R_1$ is —$CF_3$, —C(=O)$R_8$, —C(=O)O$R_8$, —C(=O)N($R_8$)$_2$, or —C(=$CH_2$)$CH_3$. In some embodiments is a compound of Formula I wherein $R_1$ is —$CF_3$. In some embodiments is a compound of Formula I wherein $R_1$ is —C(=O)$R_8$, and $R_8$ is $C_1$-$C_6$alkyl. In some embodiments is a compound of Formula I wherein $R_1$ is —C(=O)O$R_8$, and $R_8$ is $C_1$-$C_6$alkyl. In some embodiments is a compound of Formula I wherein $R_1$ is —C(=$CH_2$)$CH_3$. In another embodiment is a compound of Formula I wherein $L_1$ is a $C_1$-$C_6$alkyl and $R_1$ is hydrogen. In another embodiment of the aforementioned embodiments is a compound of Formula I wherein $R_4$ is phenyl substituted with one $R_{11}$. In another embodiment of the aforementioned embodiments is a compound of Formula I wherein $R_4$ is phenyl substituted with one $R_{11}$, $R_{11}$ is —$SO_2R_{10}$, and $R_{10}$ is $C_1$-$C_6$alkyl. In another embodiment of the aforementioned embodiments is a compound of Formula I wherein $R_4$ is phenyl substituted with at least two $R_{11}$. In another embodiment of the aforementioned embodiments is a compound of Formula I wherein $R_4$ is phenyl substituted with at least two $R_{11}$ and each $R_{11}$ is independently halogen, optionally substituted $C_1$-$C_6$alkyl, —$SO_2R_{10}$, —$NR_{10}SO_2R_{10}$, or —$SO_2N(R_{10})_2$. In another embodiment of the aforementioned embodiments is a compound of Formula I wherein n is 0. In another embodiment of the aforementioned embodiments is a compound of Formula I wherein $R_3$ is hydrogen. In another embodiment of the aforementioned embodiments is a compound of Formula I wherein $R_3$ is halogen. In another embodiment of the aforementioned embodiments is a compound of Formula I wherein X is —O—. In another embodiment of the aforementioned embodiments is a compound of Formula I wherein X is —S—. In another embodiment of the aforementioned embodiments is a compound of Formula I wherein X is —CH=CH—.

In another aspect is a compound of Formula (II):

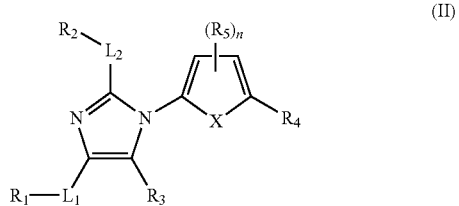

(II)

wherein:
X is —O—, —S—, or —C($R_6$)=C($R_6$)—;
$L_1$ is a bond, $C_1$-$C_6$alkyl, or $C_1$-$C_6$heteroalkyl; wherein $C_1$-$C_6$alkyl and $C_1$-$C_6$heteroalkyl are optionally substituted with at least one $R_7$;
$L_2$ is a $C_1$-$C_6$alkyl, or $C_1$-$C_6$heteroalkyl;
$R_1$ is —C(=O)O$R_8$;

$R_2$ is hydrogen, —O$R_9$, —N($R_9$)$_2$, —C(=O)$R_9$, —C(=O)N($R_9$)$_2$, —C(=N—OH)$R_9$, —C(=S)N($R_9$)$_2$, $C_1$-$C_6$alkyl, $C_3$-$C_8$cycloalkyl, $C_1$-$C_6$haloalkyl, $C_1$-$C_6$heteroalkyl, or optionally substituted heterocycloalkyl;

$R_3$ is hydrogen, halogen, $C_1$-$C_6$alkyl, or $C_1$-$C_6$haloalkyl;

$R_4$ is aryl or heteroaryl; wherein aryl and heteroaryl are substituted with at least one $R_{11}$;

each $R_5$ is independently halogen, $C_1$-$C_6$alkyl, or $C_1$-$C_6$haloalkyl;

each $R_6$ is independently hydrogen, halogen, $C_1$-$C_6$alkyl, or $C_1$-$C_6$haloalkyl;

each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —$NR_{10}$C(=O)$R_{10}$, —$NR_{10}SO_2R_{10}$, —SO$R_{10}$, —$SO_2R_{10}$, —$SO_2N(R_{10})_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and n is 0-2;

or a pharmaceutically acceptable salt, pharmaceutically acceptable solvate, or pharmaceutically acceptable prodrug thereof.

In another embodiment is a compound of Formula II wherein $L_1$ is a bond. In another embodiment is a compound of Formula II wherein $L_1$ is $C_1$-$C_6$alkyl optionally substituted with at least one $R_7$. In another embodiment is a compound of Formula II wherein $L_1$ is —$CH_2$—. In a further embodiment is a compound of Formula II wherein $R_1$ is —C(=O)O$R_8$, and $R_8$ is $C_1$-$C_6$alkyl or $C_1$-$C_6$heteroalkyl. In a further embodiment is a compound of Formula II wherein $L_2$ is $C_1$-$C_6$alkyl. In a further embodiment is a compound of Formula II wherein $R_2$ is hydrogen. In another embodiment of the aforementioned embodiments is a compound of Formula II wherein $R_4$ is phenyl substituted with one $R_{11}$. In another embodiment of the aforementioned embodiments is a compound of Formula II wherein $R_4$ is phenyl substituted with one $R_{11}$, $R_{11}$ is —$SO_2R_{10}$, and $R_{10}$ is $C_1$-$C_6$alkyl. In another embodiment of the aforementioned embodiments is a compound of Formula II wherein $R_4$ is phenyl substituted with at least two $R_{11}$. In another embodiment of the aforementioned embodiments is a compound of Formula II wherein $R_4$ is phenyl substituted with at least two $R_{11}$ and each $R_{11}$ is independently halogen, optionally substituted $C_1$-$C_6$alkyl, —$SO_2R_{10}$, —$NR_{10}SO_2R_{10}$, or —$SO_2N(R_{10})_2$. In another embodiment of the aforementioned embodiments is a compound of Formula II wherein n is 0. In another embodiment of the aforementioned embodiments is a compound of Formula II wherein $R_3$ is hydrogen. In another embodiment of the aforementioned embodiments is a compound of Formula II wherein $R_3$ is halogen. In another embodiment of the aforementioned embodiments is a compound of Formula II wherein X is —O—. In another embodiment of the aforementioned embodiments is a compound of Formula II wherein X is —S—. In another embodiment of the aforementioned embodiments is a compound of Formula II wherein X is —CH=CH—.

Also provided is a compound of Formula (III):

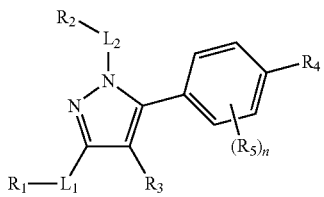

wherein:
$L_1$ is a bond, $C_1$-$C_6$alkyl, or $C_1$-$C_6$heteroalkyl; wherein $C_1$-$C_6$alkyl and $C_1$-$C_6$heteroalkyl are optionally substituted with at least one $R_7$;
$L_2$ is a $C_1$-$C_6$alkyl, or $C_1$-$C_6$heteroalkyl;
$R_1$ is —C(=O)O$R_8$;
$R_2$ is hydrogen, —O$R_9$, —N($R_9$)$_2$, —C(=O)$R_9$, —C(=O)N($R_9$)$_2$, —C(=N—OH)$R_9$, —C(=S)N($R_9$)$_2$, $C_1$-$C_6$alkyl, $C_3$-$C_8$cycloalkyl, $C_1$-$C_6$haloalkyl, $C_1$-$C_6$heteroalkyl, or optionally substituted heterocycloalkyl;
$R_3$ is hydrogen, halogen, $C_1$-$C_6$alkyl, or $C_1$-$C_6$haloalkyl;
$R_4$ is aryl or heteroaryl; wherein aryl and heteroaryl are substituted with at least one $R_{11}$;
each $R_5$ is independently halogen, $C_1$-$C_6$alkyl, or $C_1$-$C_6$haloalkyl;
each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;
$R_8$ is hydrogen, $C_1$-$C_6$alkyl, $C_1$-$C_6$heteroalkyl, —$C_1$-$C_6$alkyl-aryl, aryl, or heteroaryl;
$R_9$ is hydrogen, $C_1$-$C_6$alkyl, $C_1$-$C_6$heteroalkyl, —$C_1$-$C_6$alkyl-aryl, aryl, or heteroaryl;
each $R_{10}$ are each independently hydrogen, $C_1$-$C_6$alkyl, $C_1$-$C_6$heteroalkyl, —$C_1$-$C_6$alkyl-aryl, aryl, or heteroaryl;
each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —N$R_{10}$C(=O)$R_{10}$, —N$R_{10}$SO$_2$$R_{10}$, —SO$R_{10}$, —SO$_2$$R_{10}$, —SO$_2$N($R_{10}$)$_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and
n is 0-4;
or a pharmaceutically acceptable salt, pharmaceutically acceptable solvate, or
pharmaceutically acceptable prodrug thereof.

In another aspect is a compound of Formula (IV):

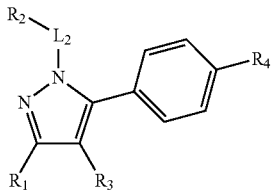

wherein:
$R_1$ is $C_1$-$C_6$ alkyl or $C_2$-$C_6$ alkenyl, wherein said $C_1$-$C_6$ alkyl is optionally substituted by 1, 2, 3, or 4 substituents independently selected from hydoxy, $C_1$-$C_4$ alkoxy, and $C_1$-$C_4$ haloalkoxy;

$L_2$ is a $C_1$-$C_6$ alkyl;
$R_2$ is C(=O)O$R_9$;
$R_3$ is hydrogen or $C_1$-$C_6$alkyl;
$R_4$ is phenyl substituted with at least one $R_{11}$;
each $R_9$ is independently hydrogen or $C_1$-$C_6$alkyl;
each $R_{10}$ is independently hydrogen or $C_1$-$C_6$alkyl; and
each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —N$R_{10}$C(=O)$R_{10}$, —N$R_{10}$SO$_2$$R_{10}$, —SO$R_{10}$, —SO$_2$$R_{10}$, —SO$_2$N($R_{10}$)$_2$, —C(=O)OCH$_2$SCH$_3$, $C_1$-$C_6$alkyl, or $C_1$-$C_6$ haloalkyl, wherein said $C_1$-$C_6$ alkyl is optionally substituted by 1, 2, 3, or 4 substituents independently selected from cyano, hydoxy, $C_1$-$C_4$ alkoxy, $C_1$-$C_4$ haloalkoxy, amino, $C_1$-$C_4$ alkylamino, and di($C_1$-$C_4$ alkyl)amino;
provided that at least one $R_{11}$ is —N$R_{10}$C(=O)$R_{10}$, —N$R_{10}$SO$_2$$R_{10}$, —SO$R_{10}$, —SO$_2$$R_{10}$, or —SO$_2$N($R_{10}$)$_2$;
or a pharmaceutically acceptable salt, pharmaceutically acceptable solvate, or
pharmaceutically acceptable prodrug thereof.

In another aspect is a pharmaceutical composition comprising a compound of Formula I, IA, IB, II, IIA, IIB, III, IIIA, IIIB, IV, IVA, and IVB, or a pharmaceutically acceptable salt thereof, and a pharmaceutically acceptable carrier.

In another aspect is a method of treating a disease, disorder or condition in a mammal that would benefit from LXR modulation comprising administering to the mammal a compound of Formula I, IA, IB, II, IIA, IIB, III, IIIA, IIIB, IV, IVA, and IVB, or a pharmaceutically acceptable salt, pharmaceutically acceptable solvate, or pharmaceutically acceptable prodrug thereof.

In a further embodiment is a method of treating a disease, disorder or condition in a mammal that would benefit from LXR modulation comprising administering to the mammal a compound of Formula I, IA, IB, II, IIA, IIB, III, IIIA, IIIB, IV, IVA, and IVB, or a pharmaceutically acceptable salt, pharmaceutically acceptable solvate, or pharmaceutically acceptable prodrug thereof; wherein the disease, disorder or condition in a mammal is a dermal disease, disorder or condition selected from skin aging, scarring, psoriasis, dermatitis, eczema, urticaria, rosacea, burns, and acne.

In another aspect is a method of modulating LXR activity comprising contacting LXR, or portion thereof, with a compound of Formula I, IA, IB, II, IIA, IIB, III, IIIA, IIIB, IV, IVA, and IVB, or a pharmaceutically acceptable salt, pharmaceutically acceptable solvate, or pharmaceutically acceptable prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

LXR was first described by Willy, P. J., et al., "LXR, a nuclear receptor that defines a distinct retinoid response pathway," Genes & Development 9:1033-1045 (Cold Spring Harbor Laboratory Press).

The liver X receptors (LXR alpha and LXR beta) are highly expressed in the epidermis and LXR activators stimulate keratinocyte proliferation and differentiation. Activation of LXRs also improves permeability barrier homeostasis by a number of mechanisms, including stimulating epidermal lipid synthesis, increasing lamellar body formation and secretion, and increasing the activity of enzymes required for the extracellular processing of lipids in the stratum corneum, leading to the formation of lamellar membranes that mediate permeability barrier function. LXR activation is also anti-inflammatory, reducing inflammation in animal models of allergic and irritant contact dermatitis. (Schmuth et al. 2008, Journal of Lipid Research, 49, 499-509).

The epidermis serves to form a barrier against excessive transcutaneous water loss to the environment. This barrier is formed by the anucleate, cornified, outermost layers of the epidermis, collectively known as the stratum corneum. The stratum corneum regulates a natural rate of water loss in the skin, a process called Transepidermal Water Loss (or TEWL). Normal, healthy moisturized skin loses about 80-100 grams of water into the atmosphere each day. The TEWL process is affected by the integrity of the epidermal barrier and lipid structure and for healthy skin, these elements regulate the rate of TEWL and help maintain the proper moisture levels in the stratum corneum.

Thus, maintenance of a normal epidermal barrier is a physiological means of inhibiting epidermal hyperproliferation.

Examples of conditions that involve or give rise to a disrupted or dysfunctional epidermal barrier are: inflammation to mucous membranes, such as cheilitis, chapped lips, nasal irritation and vulvovaginitis; eczematous dermnatitides, such as atopic and seborrheic dermatitis, allergic or irritant contact dermatitis, eczema craquelee, photoallergic dermatitis, phototoxic dermatitis, phytophotodermatitis, radiation dermatitis, and stasis dermatitis; ulcers and erosions resulting from trauma, burns, bullous disorders, or ischemia of the skin or mucous membranes; several forms of ichthyoses; epidermolysis bullosae; psoriasis; hypertrophic scars and keloids and cutaneous changes of intrinsic aging and photoaging; and the like.

The constituents of the epidermis that play a role in maintenance of a functional barrier are the intercellular, lamellar bilayer sheets of stratum corneum lipids. The synthesis of stratum corneum lipids is relatively autonomous from circulating or dietary influences. The synthetic response is regulated instead by alterations in permeability barrier functions. The regulation occurs through changes in the activities, phosphorylation (activation) state, mass, and mRNA for the rate-limiting enzymes of each of the three key lipids: serine palmitoyl transferase (for ceramides), HMG-CoA reductase (for cholesterol), and both acetyl CoA carboxylase and fatty acid synthase (for fatty acids). Other results of alterations in barrier function are the regulation of key enzymes of extracellular lipid processing. One such enzyme is beta-glucocerebrosidase, which catalyzes the conversion of precursor glycosylceramides into ceramides.

It has now been discovered that the formation of a mature, fully differentiated stratum corneum and a functional epidermal permeability barrier are accelerated by the topical administration of certain activators of liver X receptor (LXR) with its two isoforms, LXR alpha and LXR beta.

LXR activators improve barrier function by at least two parallel mechanisms—stimulation of epidermal differentiation and lipid production. Since increased epidermal lipid production likely generates additional endogenous activators of these nuclear hormone receptors, this process can be viewed as a type of feed-forward mechanism that coordinately regulates generation of both the corneocytes and the extracellular matrix of the stratum corneum.

Hatano et al. have shown that topical application of LXR activators improves multiple parameters of the AD-like dermatosis in a hapten-induced mouse model (Hatano et al (2010) The Journal of Allergy and Clinical Immunology 125 (1) 160-169. This model recapitulates virtually all of the known clinical, structural, functional, lipid biochemical, and immunologic abnormalities of human AD.

Inherited abnormalities in proteins important for the barrier predispose to the development of atopic dermatitis (AD). Conversely, normalization of barrier function would, in turn, reduce the two major drivers of inflammation in AD. Provided herein are methods for reducing cytokine generation, originating from, for example, perturbed corneocytes. In one embodiment, treatment with topical LXR activators reduces IL-la and TNFα levels. In addition, improved permeability barrier function simultaneously reduces the transdermal penetration of pro-inflammatory xenobiotes, including haptens and microbial pathogens.

Chang et al (Mol Endocrinol 2008, 22, 2407-2419) have shown the efficacy of the LXR ligands in normal human epidermal keratinocytes and in a mouse model of photoaging. A comprehensive molecular basis for the efficacy in the mouse model was established by in vitro studies in normal human epidermal keratinocytes and in skin cell preparations from LXR wild-type and LXR knock-out mice. In these studies, LXR activators:

(a) reduced the expression of cytokines and metalloproteinases in UV-activated epidermal keratinocytes and TNFα-activated dermal fibroblasts (b) increased the expression of keratinocyte differentiation markers (c) increased the expression of genes required for fatty acid synthesis in keratinocytes (d) increased the expression of cholesterol binding proteins and lipid transporters in skin cells (e) increased the expression of enzymes involved in ceramide synthesis in keratinocytes.

Lee et al (J Invest Dermatol. 2012 Dec. 6. doi: 10.1038/jid.2012.409. [Epub ahead of print]) have shown that in human primary melanocytes, MNT-1, and B16 melanoma cells, LXR activation and LXR agonists have been shown to inhibit melanogenesis by downregulating melanogenic enzymes through Ras- and ERK-induced MITF degradation. This supports the rationale that LXRs may be key target proteins for in pigmentary disorders and that LXR agonists may be beneficial in the treatment of dermal pigmantary disorders including vitiligo.

Pencheva et al (*Cell*. 2012 Nov. 21; 151(5):1068-82) have shown that targeting apolipoproteins in the skin such as ApoE convergently effects molecular targets such as LRP1/LRP8 which are implicated in melanoma metastasis and angiogenesis. As ApoE is a target gene for LXR, LXR activation may be beneficial in the treatment of dermal malignancies including metastatic melanoma.

Accordingly provided herein are methods and compositions comprising LXR activators as active ingredients in a formulation that is pharmaceutically acceptable for topical administration.

Topical formulations containing LXR activators or activators described herein are applied to beneficial effect to skin and/or mucus membranes. The activators are formulated as lotions, solutions, gels, creams, emollient creams, unguents, sprays, or any other form that will permit topical application. The formulation may also contain one or more agents that promote the spreading of the formulation over the affected area, but are otherwise biologically inactive.

Examples of these agents are surfactants, humectants, wetting agents, emulsifiers, or propellants.

Amounts that are referred to herein as effective in enhancing barrier development are any amount that will cause a substantial relief of the symptoms of a disrupted or dysfunctional epidermal permeability barrier when applied repeatedly over time. The optimum amounts in any given instance will be readily apparent to those skilled in the art or are capable of determination by routine experimentation.

Examples of skin conditions that are susceptible to topical treatment with LXR activators are: atopic and seborrheic dermatitis; inflammation to mucous membranes, such as cheilitis, chapped lips, nasal irritation and vulvovaginitis; eczematous dermatitis resulting from allergic and irritant contact, eczema craquelee, radiation and stasis dermatitis; ulcers and erosions due to chemical or thermal burns, bullous disorders, or vascular compromise or ischemia including venous, arterial, embolic or diabetic ulcers; ichthyoses, with or without an associated barrier abnormality; epidermolysis bullosa; psoriasis; hypertrophic scars and keloids; intrinsic aging, photo aging and/or dermatoheliosus; melanoma and non-melanoma skin cancer, including lignin melanoma, basal cell carcinoma, squamous cell carcinoma, actinic keratoses, and virally induced neoplasia (warts and condylomata accuminata).

Optimal methods and frequency of administration will be readily apparent to those skilled in the art or are capable of determination by routine experimentation. Effective results in most cases are achieved by topical application of a thin layer over the affected area, or the area where one seeks to achieve the desired effect. Depending on the condition being addressed, its stage or degree, and whether application is done for therapeutic or preventive reasons, effective results are achieved with application rates of from one application every two or three days to four or more applications per day.

The methods and compositions described herein are generally applicable to the treatment of mammalian skin including for example humans, domestic pets, and livestock and other farm animals.

Definitions

In the context of this disclosure, a number of terms shall be utilized.

As used herein, the term "about" or "approximately" means within 20%, preferably within 10%, and more preferably within 5% of a given value or range.

The term a "therapeutically effective amount" as used herein refers to the amount of an LXR modulator that, when administered to a mammal in need, is effective to at least partially ameliorate or to at least partially prevent conditions related to skin aging.

As used herein, the term "expression" includes the process by which polynucleotides are transcribed into mRNA and translated into peptides, polypeptides, or proteins.

The term "modulate" encompasses either a decrease or an increase in activity or expression depending on the target molecule. For example, a TIMP1 modulator is considered to modulate the expression of TIMP1 if the presence of such TIMP1 modulator results in an increase or decrease in TIMP1 expression.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The terms "induce" or "induction" of TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSynuclein (αSyn), or decorin expression refer to an increase, induction, or otherwise augmentation of TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, or decorin mRNA and/or protein expression. The increase, induction, or augmentation can be measured by one of the assays provided herein. Induction of TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, or decorin expression does not necessarily indicate maximal expression of TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, or decorin. An increase in TIMP1, ABCA12, or decorin expression can be, for example, at least about 10%, 20%, 30%, 40%, 50%, 60%, 70%, 80%, 90% or more. In one embodiment, induction is measured by comparing TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, or decorin mRNA expression levels from untreated keratinocytes to that of TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, or decorin mRNA expression levels from LXR modulator-treated keratinocytes.

The terms "inhibit" or "inhibition" of TNFα, MMP1, MMP3, or IL-8 expression refer to a reduction, inhibition, or otherwise diminution of TNFα, MMP1, MMP3, or IL-8 mRNA and/or protein expression. The reduction, inhibition, or diminution of binding can be measured by one of the assays provided herein. Inhibition of TNFα, MMP1, MMP3, or IL-8 expression does not necessarily indicate a complete negation of TNFα, MMP1, MMP3, or IL-8 expression. A reduction in expression can be, for example, at least about 10%, 20%, 30%, 40%, 50%, 60%, 70%, 80%, 90% or more. In one embodiment, inhibition is measured by comparing TNFα, MMP1, MMP3, or IL-8 mRNA expression levels from untreated keratinocytes to that of TNFα, MMP1, MMP3, or IL-8 mRNA expression levels from LXR modulator-treated keratinocytes.

"Liver X receptor" or "LXR" refers to both LXRα and LXRβ, and variants, isoforms, and active fragments thereof. LXRβ is ubiquitously expressed, while LXRα expression is limited to liver, kidney, intestine, spleen, adipose tissue, macrophages, skeletal muscle, and, as demonstrated herein, skin. Representative GenBank® accession numbers for LXRα sequences include the following: human (*Homo sapiens*, Q 13133), mouse (*Mus musculus*, Q9Z0Y9), rat (*Rattus norvegicus*, Q62685), cow (*Bos taurus*, Q5E9B6), pig (*Sus scrofa*, AAY43056), chicken (*Gallus gallus*, AAM90897). Representative GenBank® accession numbers for LXRβ include the following: human (*Homo sapiens*, P55055), mouse (*Mus musculus*, Q60644), rat (*Rattus norvegicus*, Q62755), cow (*Bos taurus*, Q5BIS6).

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

"Proinflammatory cytokine" as used herein refers to any cytokine that can activate cytotoxic, inflammatory, or delayed hypersensitivity reactions. Exemplary proinflammatory cytokines include colony stimulating factors (CSFs), for example granulocyte-macrophage CSF, granulocyte CSF, erythropoietin; transforming growth factors (TGFs), for example TGFβ; interferons (IFNs), for example IFNα, IFNβ, IFNγ; interleukins (ILs), for example IL-1α, IL-1β, IL-3, IL-6, IL-7, IL-8, IL-9, IL-11, IL-12, IL-15; tumor necrosis factors (TNFs), for example TNFα, TNFβ; adherence proteins, for example intracellular adhesion molecule (ICAM), vascular cell adhesion molecule (VCAM); growth factors, for example leukemia inhibitory factor (LIF), macrophage migration-inhibiting factor (MIF), epidermal growth factor (EGF), platelet-derived growth factor (PDGF), fibroblast growth factor (FGF), insulin-like growth factor (IGF), nerve growth factor (NGF), B-cell growth factor (BCGF); chemokines, for example monocyte chemoattractant proteins (MCP-1, MCP-2, MCP-3), macrophage inflammatory protein (MIP), growth-related oncogene, gamma interferon-inducible protein; leukotrienes, for example leukotriene B$_4$, leukotrine D$_4$; vasoactive factors, for example histamine, bradykinin, platelet activating factor (PAF); prostaglandins, for example prostaglandin E2.

The term "skin aging" includes conditions derived from intrinsic chronological aging (for example, deepened expression lines, reduction of skin thickness, inelasticity, and/or unblemished smooth surface), those derived from photoaging (for example, deep wrinkles, yellow and leathery surface, hardening of the skin, elastosis, roughness, dyspigmentations (age spots) and/or blotchy skin), and those derived from steroid-induced skin thinning.

LXR Modulators

LXR modulators contemplated for use in the compositions and methods described herein are compounds with LXRα and/or LXRβ modulator activities. The term "LXR modulator" includes LXRα and/or LXRβ agonists, antagonists and tissue selective LXR modulators, as well as other agents that induce the expression and/or protein levels of LXRs in the skin cells.

Preferred compounds will be LXR modulators with LXRα and/or LXRβ modulator activities. Preferred LXR modulators are LXR activators. The term "LXR activator" or "activator of the LXR" includes LXRα and/or LXRβ agonists, partial agonists and tissue selective LXR modulators, as well as other agents that induce the expression and/or protein levels of LXRs in the skin cells.

In one embodiment is a compound of Formula (I):

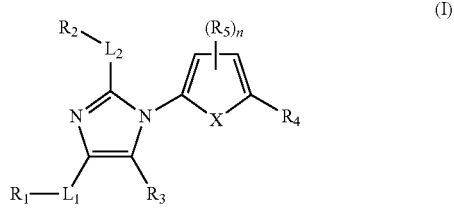

wherein:

X is —O—, —S—, or —C(R$_6$)=C(R$_6$)—;

L$_1$ and L$_2$ are each independently a bond, C$_1$-C$_6$alkyl, or C$_1$-C$_6$heteroalkyl; wherein C$_1$-C$_6$alkyl and C$_1$-C$_6$heteroalkyl are optionally substituted with at least one R$_7$;

R$_1$ is halogen, —CF$_3$, —OR$_8$, —N(R$_8$)$_2$, —C(=O)R$_8$, —C(=O)OR$_8$, —C(=O)N(R$_8$)$_2$, —C(=N—OH)R$_8$, —C(=S)N(R$_8$)$_2$, C$_1$-C$_6$alkyl, C$_1$-C$_6$heteroalkyl, or optionally substituted C$_2$-C$_7$heterocycloalkyl;

R$_2$ is —C(=O)OR$_9$;

R$_3$ is hydrogen, halogen, C$_1$-C$_6$alkyl, or C$_1$-C$_6$haloalkyl;

R$_4$ is aryl or heteroaryl; wherein aryl and heteroaryl are substituted with at least one R$_{11}$;

each R$_5$ is independently halogen, C$_1$-C$_6$alkyl, or C$_1$-C$_6$haloalkyl;

each R$_6$ is independently hydrogen, halogen, C$_1$-C$_6$alkyl, or C$_1$-C$_6$haloalkyl;

each R$_7$ is independently C$_1$-C$_6$alkyl, C$_3$-C$_8$cycloalkyl, C$_1$-C$_6$haloalkyl, C$_1$-C$_6$heteroalkyl, —C$_1$-C$_6$alkyl-aryl, optionally substituted aryl, or optionally substituted heteroaryl;

each R$_8$, each R$_9$, and each R$_{10}$ are each independently hydrogen, C$_1$-C$_6$alkyl, C$_1$-C$_6$heteroalkyl, —C$_1$-C$_6$alkyl-aryl, aryl, or heteroaryl;

each R$_{11}$ is independently halogen, nitro, —OR$_{10}$, —N(R$_{10}$)$_2$, —CN, —C(=O)R$_{10}$, —C(=O)OR$_{10}$, —C(=O)N(R$_{10}$)$_2$, —NR$_{10}$C(=O)R$_{10}$, —NR$_{10}$SO$_2$R$_{10}$, —SOR$_{10}$, —SO$_2$R$_{10}$, —SO$_2$N(R$_{10}$)$_2$, —C(=O)OCH$_2$SCH$_3$, optionally substituted C$_1$-C$_6$alkyl, optionally substituted C$_3$-C$_8$cycloalkyl, optionally substituted C$_1$-C$_6$haloalkyl, optionally substituted C$_1$-C$_6$heteroalkyl, optionally substituted —C$_1$-C$_6$alkyl-aryl, optionally substituted aryl, or optionally substituted heteroaryl; and n is 0-2;

or a pharmaceutically acceptable salt, pharmaceutically acceptable solvate, or pharmaceutically acceptable prodrug thereof.

In some embodiments is a compound of Formula I wherein X is —O—. In further embodiments is a compound of Formula I wherein R$_1$ is halogen, —CF$_3$, —OR$_8$, —N(R$_8$)$_2$, —C(=O)R$_8$, —C(=O)OR$_8$, —C(=O)N(R$_8$)$_2$, —C(=N—OH)R$_8$, —C(=S)N(R$_8$)$_2$, C$_1$-C$_6$alkyl, C$_1$-C$_6$heteroalkyl, or optionally substituted C$_2$-C$_7$heterocycloalkyl. In some embodiments is a compound of Formula I wherein R$_1$ is halogen. In some embodiments is a compound of Formula I wherein R$_1$ is —CF$_3$. In some embodiments is a compound of Formula I wherein R$_1$ is —OR$_8$. In some embodiments is a compound of Formula I wherein R$_1$ is —N(R$_8$)$_2$. In some embodiments is a compound of Formula I wherein R$_1$ is —C(=O)R$_8$. In some embodiments is a compound of Formula I wherein R$_1$ is —C(=O)OR$_8$. In some embodiments is a compound of Formula I wherein R$_1$ is —C(=O)N(R$_8$)$_2$. In some embodiments is a compound of Formula I wherein R$_1$ is —C(=N—OH)R$_8$. In some embodiments is a compound of Formula I wherein R$_1$ is —C(=S)N(R$_8$)$_2$. In some embodiments is a compound of Formula I wherein R$_1$ is C$_1$-C$_6$alkyl. In some embodiments is a compound of Formula I wherein R$_1$ is C$_1$-C$_6$heteroalkyl. In some embodiments is a compound of Formula I wherein R$_1$ is optionally substituted C$_2$-C$_7$heterocycloalkyl. In further embodiments is a compound of Formula I wherein R$_8$ is hydrogen, C$_1$-C$_6$alkyl, C$_1$-C$_6$heteroalkyl, —C$_1$-C$_6$alkyl-aryl, aryl, or heteroaryl. In some embodiments is a compound of Formula I wherein R$_8$ is hydrogen. In some embodiments is a compound of Formula I wherein R$_8$ is C$_1$-C$_6$alkyl. In some embodiments is a compound of Formula I wherein R$_8$ is methyl. In some embodiments, R$_8$ is ethyl. In some embodiments is a compound of Formula I wherein R$_8$ is C$_1$-C$_6$heteroalkyl. In some embodiments is a compound of Formula I wherein R$_8$ is —C$_1$-C$_6$alkyl-aryl. In some embodiments is a compound of Formula I wherein $R_8$ is aryl. In some embodiments is a compound of Formula I wherein $R_8$ is heteroaryl.

In some embodiments is a compound of Formula I wherein X is —O—, $R_2$ is —C(=O)$OR_9$, and $R_9$ is hydrogen, $C_1$-$C_6$alkyl, $C_1$-$C_6$heteroalkyl, —$C_1$-$C_6$alkyl-aryl, aryl, or heteroaryl. In some embodiments is a compound of Formula I wherein X is —O—, $R_2$ is —C(=O)$OR_9$, and $R_9$ is hydrogen. In some embodiments is a compound of Formula I wherein X is —O—, $R_2$ is —C(=O)$OR_9$, and $R_9$ is $C_1$-$C_6$alkyl. In some embodiments is a compound of Formula I wherein X is —O—, $R_2$ is —C(=O)$OR_9$, and $R_9$ is methyl. In some embodiments is a compound of Formula I wherein X is —O—, $R_2$ is —C(=O)$OR_9$, and $R_9$ is ethyl. In some embodiments is a compound of Formula I wherein X is —O—, $R_2$ is —C(=O)$OR_9$, and $R_9$ is $C_1$-$C_6$heteroalkyl. In some embodiments is a compound of Formula I wherein X is —O—, $R_2$ is —C(=O)$OR_9$, and $R_9$ is —$C_1$-$C_6$alkyl-aryl. In some embodiments is a compound of Formula I wherein X is —O—, $R_2$ is —C(=O)$OR_9$, and $R_9$ is aryl. In some embodiments is a compound of Formula I wherein X is —O—, $R_2$ is —C(=O)$OR_9$, and $R_9$ is heteroaryl.

In some embodiments is a compound of Formula I wherein X is —O— and $L_1$ and $L_2$ are each independently a bond, $C_1$-$C_6$alkyl, or $C_1$-$C_6$heteroalkyl; wherein $C_1$-$C_6$alkyl and $C_1$-$C_6$heteroalkyl are optionally substituted with at least one $R_7$. In further embodiments is a compound of Formula I wherein X is —O—, and $L_1$ and $L_2$ are each a bond. In further embodiments is a compound of Formula I wherein X is —O—, $L_1$ is a bond, and $L_2$ is $C_1$-$C_6$alkyl optionally substituted with at least one $R_7$. In further embodiments is a compound of Formula I wherein X is —O—, $L_1$ is a bond, and $L_2$ is $C_1$-$C_6$heteroalkyl optionally substituted with at least one $R_7$. In further embodiments is a compound of Formula I wherein X is —O—, and $L_1$ and $L_2$ are each $C_1$-$C_6$alkyl optionally substituted with at least one $R_7$. In further embodiments is a compound of Formula I wherein X is —O—, $L_1$ is $C_1$-$C_6$alkyl optionally substituted with at least one $R_7$, and $L_2$ is a bond. In further embodiments is a compound of Formula I wherein X is —O—, $L_1$ is $C_1$-$C_6$alkyl optionally substituted with at least one $R_7$, and $L_2$ is $C_1$-$C_6$heteroalkyl optionally substituted with at least one $R_7$. In further embodiments is a compound of Formula I wherein X is —O—, and $L_1$ and $L_2$ are each $C_1$-$C_6$heteroalkyl optionally substituted with at least one $R_7$. In further embodiments is a compound of Formula I wherein X is —O—, $L_1$ is $C_1$-$C_6$heteroalkyl optionally substituted with at least one $R_7$, and $L_2$ is a bond. In further embodiments is a compound of Formula I wherein X is —O—, $L_1$ is $C_1$-$C_6$heteroalkyl optionally substituted with at least one $R_7$, and $L_2$ is $C_1$-$C_6$alkyl optionally substituted with at least one $R_7$. In a further embodiment of the aforementioned embodiments is a compound of Formula I wherein each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments of the aforementioned embodiments is a compound of Formula I wherein each $R_7$ is $C_1$-$C_6$alkyl. In some embodiments of the aforementioned embodiments is a compound of Formula I wherein each $R_7$ is —$C_1$-$C_6$alkyl-aryl. In some embodiments of the aforementioned embodiments is a compound of Formula I wherein each $R_7$ is optionally substituted aryl.

In some embodiments is a compound of Formula I wherein X is —O— and $R_4$ is aryl or heteroaryl; wherein aryl and heteroaryl are substituted with at least one $R_{11}$. In some embodiments is a compound of Formula I wherein $R_4$ is aryl substituted with one $R_{11}$. In some embodiments is a compound of Formula I wherein $R_4$ is aryl substituted with two $R_{11}$. In some embodiments is a compound of Formula I wherein $R_4$ is aryl substituted with three $R_{11}$. In further embodiments is a compound of Formula I wherein $R_4$ is phenyl substituted with one $R_{11}$. In further embodiments is a compound of Formula I wherein $R_4$ is phenyl substituted with two $R_{11}$. In further embodiments is a compound of Formula I wherein $R_4$ is phenyl substituted with three $R_{11}$. In some embodiments is a compound of Formula I wherein $R_4$ is heteroaryl substituted with one $R_{11}$. In some embodiments is a compound of Formula I wherein $R_4$ is heteroaryl substituted with two $R_{11}$. In some embodiments is a compound of Formula I wherein $R_4$ is heteroaryl substituted with three $R_{11}$.

In some embodiments is a compound of Formula I wherein X is —O—, $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, —$NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula I wherein X is —O—, $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, —$NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments is a compound of Formula I wherein $R_{11}$ is —$OR_{10}$. In further embodiments is a compound of Formula I wherein $R_{11}$ is —$N(R_{10})_2$. In further embodiments is a compound of Formula I wherein $R_{11}$ is —CN. In further embodiments is a compound of Formula I wherein $R_{11}$ is —C(=O)$R_{10}$. In further embodiments is a compound of Formula I wherein $R_{11}$ is —C(=O)$OR_{10}$. In further embodiments is a compound of Formula I wherein $R_{11}$ is —C(=O)$N(R_{10})_2$. In further embodiments is a compound of Formula I wherein $R_{11}$ is —$NR_{10}$C(=O)$R_{10}$. In further embodiments is a compound of Formula I wherein $R_{11}$ is $NR_{10}SO_2R_{10}$. In further embodiments is a compound of Formula I wherein $R_{11}$ is —$SOR_{10}$. In further embodiments is a compound of Formula I wherein $R_{11}$ is —$SO_2R_{10}$. In further embodiments is a compound of Formula I wherein $R_{11}$ is —$SO_2N(R_{10})_2$. In further embodiments is a compound of Formula I wherein $R_{11}$ is —C(=O)$OCH_2SCH_3$. In further embodiments is a compound of Formula I wherein $R_{11}$ is $C_1$-$C_6$alkyl. In further embodiments is a compound of Formula I wherein $R_{11}$ is optionally substituted $C_3$-$C_8$cycloalkyl. In further embodiments is a compound of Formula I wherein $R_{11}$ is $C_1$-$C_6$haloalkyl. In further embodiments is a compound of Formula I wherein $R_{11}$ is $C_1$-$C_6$heteroalkyl. In further embodiments is a compound of Formula I wherein $R_{11}$ is —$C_1$-$C_6$alkyl-aryl. In further embodiments is a compound of Formula I wherein $R_{11}$ is optionally substituted aryl. In further embodiments is a compound of Formula I wherein $R_{11}$ is optionally substituted heteroaryl. In yet further embodiments is a compound of Formula I wherein each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments is a compound of Formula I wherein $R_{10}$ is hydrogen. In some embodiments is a compound of Formula I wherein $R_{10}$ is $C_1$-$C_6$alkyl. In some embodiments is a compound of Formula I wherein $R_{10}$ is $C_1$-$C_6$heteroalkyl. In some embodiments is a compound of Formula I wherein $R_{10}$ is $-C_1-C_6$alkyl-aryl. In some embodiments is a compound of Formula I wherein $R_{10}$ is aryl. In some embodiments is a compound of Formula I wherein $R_{10}$ is heteroaryl.

In another embodiment is a compound of Formula I wherein X is $-O-$, $R_2$ is $C(=O)OR_9$, $R_9$ is $C_1-C_6$alkyl, and $L_2$ is a bond. In another embodiment is a compound of Formula I wherein X is $-O-$, $R_2$ is $C(=O)OR_9$, $R_9$ is $C_1-C_6$alkyl, $L_2$ is a bond, $L_1$ is a bond and $R_1$ is $-CF_3$. In another embodiment is a compound of Formula I wherein X is $-O-$, $R_2$ is $C(=O)OR_9$, $R_9$ is $C_1-C_6$alkyl, $L_2$ is a bond, $L_1$ is a bond and $R_1$ is $C_1-C_6$alkyl. In another embodiment is a compound of Formula I wherein X is $-O-$, $R_2$ is $C(=O)OR_9$, $R_9$ is $C_1-C_6$alkyl, $L_2$ is a bond, $L_1$ is a bond and $R_1$ is $C(=O)OR_8$. In another embodiment is a compound of Formula I wherein X is $-O-$, $R_2$ is $C(=O)OR_9$, $R_9$ is $C_1-C_6$alkyl, $L_2$ is a bond, $L_1$ is a bond and $R_1$ is $C(=O)R_8$. In a further embodiment of the aforementioned embodiments is a compound of Formula I wherein $R_4$ is phenyl substituted with one $R_{11}$. In a further embodiment of the aforementioned embodiments is a compound of Formula I wherein $R_4$ is phenyl substituted with one $R_{11}$, $R_{11}$ is $-SO_2R_{10}$ and $R_{10}$ is $C_1-C_6$alkyl. In yet a further embodiment of the aforementioned embodiments is a compound of Formula I wherein $R_4$ is phenyl substituted with one $R_{11}$, $R_{11}$ is $-SO_2R_{10}$ and $R_{10}$ is $CH_3$.

In another embodiment is a compound of Formula I wherein X is $-O-$, $R_2$ is $C(=O)OR_9$, $R_9$ is $C_1-C_6$alkyl, and $L_2$ is $C_1-C_6$alkyl. In another embodiment is a compound of Formula I wherein X is $-O-$, $R_2$ is $C(=O)OR_9$, $R_9$ is $C_1-C_6$alkyl, $L_2$ is $C_1-C_6$alkyl, $L_1$ is a bond and $R_1$ is $-CF_3$. In another embodiment is a compound of Formula I wherein X is $-O-$, $R_2$ is $C(=O)OR_9$, $R_9$ is $C_1-C_6$alkyl, $L_2$ is $C_1-C_6$alkyl, $L_1$ is a bond and $R_1$ is $C_1-C_6$alkyl. In another embodiment is a compound of Formula I wherein X is $-O-$, $R_2$ is $C(=O)OR_9$, $R_9$ is $C_1-C_6$alkyl, $L_2$ is $C_1-C_6$alkyl, $L_1$ is a bond and $R_1$ is $C(=O)OR_8$. In another embodiment is a compound of Formula I wherein X is $-O-$, $R_2$ is $C(=O)OR_9$, $R_9$ is $C_1-C_6$alkyl, $L_2$ is $C_1-C_6$alkyl, $L_1$ is a bond and $R_1$ is $C(=O)R_8$. In a further embodiment of the aforementioned embodiments is a compound of Formula I wherein $R_4$ is phenyl substituted with one $R_{11}$. In a further embodiment of the aforementioned embodiments is a compound of Formula I wherein $R_4$ is phenyl substituted with one $R_{11}$, $R_{11}$ is $-SO_2R_{10}$ and $R_{10}$ is $C_1-C_6$alkyl. In yet a further embodiment of the aforementioned embodiments is a compound of Formula I wherein $R_4$ is phenyl substituted with one $R_{11}$, $R_{11}$ is $-SO_2R_{10}$ and $R_{10}$ is $CH_3$.

In another embodiment of the aforementioned embodiments is a compound of Formula I wherein $R_3$ is hydrogen, halogen, $C_1-C_6$alkyl, or $C_1-C_6$haloalkyl. In some embodiments of the aforementioned embodiments is a compound of Formula I wherein $R_3$ is hydrogen. In some embodiments of the aforementioned embodiments is a compound of Formula I wherein $R_3$ is halogen. In some embodiments of the aforementioned embodiments is a compound of Formula I wherein $R_3$ is $C_1-C_6$alkyl. In some embodiments of the aforementioned embodiments is a compound of Formula I wherein $R_3$ is $C_1-C_6$haloalkyl.

In some embodiments is a compound of Formula I wherein X is $-S-$. In further embodiments is a compound of Formula I wherein $R_1$ is halogen, $-CF_3$, $-OR_8$, $-N(R_8)_2$, $-C(=O)R_8$, $-C(=O)OR_8$, $-C(=O)N(R_8)_2$, $-C(=N-OH)R_8$, $-C(=S)N(R_8)_2$, $C_1-C_6$alkyl, $C_1-C_6$heteroalkyl, or optionally substituted $C_2-C_7$heterocycloalkyl. In some embodiments is a compound of Formula I wherein $R_1$ is halogen. In some embodiments is a compound of Formula I wherein $R_1$ is $-CF_3$. In some embodiments is a compound of Formula I wherein $R_1$ is $-OR_8$. In some embodiments is a compound of Formula I wherein $R_1$ is $-N(R_8)_2$. In some embodiments is a compound of Formula I wherein $R_1$ is $-C(=O)R_8$. In some embodiments is a compound of Formula I wherein $R_1$ is $-C(=O)OR_8$. In some embodiments is a compound of Formula I wherein $R_1$ is $-C(=O)N(R_8)_2$. In some embodiments is a compound of Formula I wherein $R_1$ is $-C(=N-OH)R_8$. In some embodiments is a compound of Formula I wherein $R_1$ is $-C(=S)N(R_8)_2$. In some embodiments is a compound of Formula I wherein $R_1$ is $C_1-C_6$alkyl. In some embodiments is a compound of Formula I wherein $R_1$ is $C_1-C_6$heteroalkyl. In some embodiments is a compound of Formula I wherein $R_1$ is optionally substituted $C_2-C_7$heterocycloalkyl. In further embodiments is a compound of Formula I wherein $R_8$ is hydrogen, $C_1-C_6$alkyl, $C_1-C_6$heteroalkyl, $-C_1-C_6$alkyl-aryl, aryl, or heteroaryl. In some embodiments is a compound of Formula I wherein $R_8$ is hydrogen. In some embodiments is a compound of Formula I wherein $R_8$ is $C_1-C_6$alkyl. In some embodiments is a compound of Formula I wherein $R_8$ is methyl. In some embodiments, $R_8$ is ethyl. In some embodiments is a compound of Formula I wherein $R_8$ is $C_1-C_6$heteroalkyl. In some embodiments is a compound of Formula I wherein $R_8$ is $-C_1-C_6$alkyl-aryl. In some embodiments is a compound of Formula I wherein $R_8$ is aryl. In some embodiments is a compound of Formula I wherein $R_8$ is heteroaryl.

In some embodiments is a compound of Formula I wherein X is $-S-$, $R_2$ is $-C(=O)OR_9$, and $R_9$ is hydrogen, $C_1-C_6$alkyl, $C_1-C_6$heteroalkyl, $-C_1-C_6$alkyl-aryl, aryl, or heteroaryl. In some embodiments is a compound of Formula I wherein X is $-S-$, $R_2$ is $-C(=O)OR_9$, and $R_9$ is hydrogen. In some embodiments is a compound of Formula I wherein X is $-S-$, $R_2$ is $-C(=O)OR_9$, and $R_9$ is $C_1-C_6$alkyl. In some embodiments is a compound of Formula I wherein X is $-S-$, $R_2$ is $-C(=O)OR_9$, and $R_9$ is methyl. In some embodiments is a compound of Formula I wherein X is $-S-$, $R_2$ is $-C(=O)OR_9$, and $R_9$ is ethyl. In some embodiments is a compound of Formula I wherein X is $-S-$, $R_2$ is $-C(=O)OR_9$, and $R_9$ is $C_1-C_6$heteroalkyl. In some embodiments is a compound of Formula I wherein X is $-S-$, $R_2$ is $-C(=O)OR_9$, and $R_9$ is $-C_1-C_6$alkyl-aryl. In some embodiments is a compound of Formula I wherein X is $-S-$, $R_2$ is $-C(=O)OR_9$, and $R_9$ is aryl. In some embodiments is a compound of Formula I wherein X is $-S-$, $R_2$ is $-C(=O)OR_9$, and $R_9$ is heteroaryl.

In some embodiments is a compound of Formula I wherein X is $-S-$ and $L_1$ and $L_2$ are each independently a bond, $C_1-C_6$alkyl, or $C_1-C_6$heteroalkyl; wherein $C_1-C_6$alkyl and $C_1-C_6$heteroalkyl are optionally substituted with at least one $R_7$. In further embodiments is a compound of Formula I wherein X is $-S-$, and $L_1$ and $L_2$ are each a bond. In further embodiments is a compound of Formula I wherein X is $-S-$, $L_1$ is a bond, and $L_2$ is $C_1-C_6$alkyl optionally substituted with at least one $R_7$. In further embodiments is a compound of Formula I wherein X is $-S-$, $L_1$ is a bond, and $L_2$ is $C_1-C_6$heteroalkyl optionally substituted with at least one $R_7$. In further embodiments is a compound of Formula I wherein X is $-S-$, and $L_1$ and $L_2$ are each $C_1-C_6$alkyl optionally substituted with at least one $R_7$. In further embodiments is a compound of Formula I wherein X is $-S-$, $L_1$ is $C_1-C_6$alkyl optionally substituted with at least one $R_7$, and $L_2$ is a bond. In further embodiments is a compound of Formula I wherein X is $-S-$, $L_1$ is $C_1-C_6$alkyl optionally substituted with at least one $R_7$, and $L_2$ is $C_1$-$C_6$heteroalkyl optionally substituted with at least one $R_7$. In further embodiments is a compound of Formula I wherein X is —S—, and $L_1$ and $L_2$ are each $C_1$-$C_6$heteroalkyl optionally substituted with at least one $R_7$. In further embodiments is a compound of Formula I wherein X is —S—, $L_1$ is $C_1$-$C_6$heteroalkyl optionally substituted with at least one $R_7$, and $L_2$ is a bond. In further embodiments is a compound of Formula I wherein X is —S—, $L_1$ is $C_1$-$C_6$heteroalkyl optionally substituted with at least one $R_7$, and $L_2$ is $C_1$-$C_6$alkyl optionally substituted with at least one $R_7$. In a further embodiment of the aforementioned embodiments is a compound of Formula I wherein each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments of the aforementioned embodiments is a compound of Formula I wherein each $R_7$ is $C_1$-$C_6$alkyl. In some embodiments of the aforementioned embodiments is a compound of Formula I wherein each $R_7$ is —$C_1$-$C_6$alkyl-aryl. In some embodiments of the aforementioned embodiments is a compound of Formula I wherein each $R_7$ is optionally substituted aryl.

In some embodiments is a compound of Formula I wherein X is —S— and $R_4$ is aryl or heteroaryl; wherein aryl and heteroaryl are substituted with at least one $R_{11}$. In some embodiments is a compound of Formula I wherein $R_4$ is aryl substituted with one $R_{11}$. In some embodiments is a compound of Formula I wherein $R_4$ is aryl substituted with two $R_{11}$. In some embodiments is a compound of Formula I wherein $R_4$ is aryl substituted with three $R_{11}$. In further embodiments is a compound of Formula I wherein $R_4$ is phenyl substituted with one $R_{11}$. In further embodiments is a compound of Formula I wherein $R_4$ is phenyl substituted with two $R_{11}$. In further embodiments is a compound of Formula I wherein $R_4$ is phenyl substituted with three $R_{11}$. In some embodiments is a compound of Formula I wherein $R_4$ is heteroaryl substituted with one $R_{11}$. In some embodiments is a compound of Formula I wherein $R_4$ is heteroaryl substituted with two $R_{11}$. In some embodiments is a compound of Formula I wherein $R_4$ is heteroaryl substituted with three $R_{11}$.

In some embodiments is a compound of Formula I wherein X is —S—, $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, —$NR_{10}SO_2R_{10}$, —$SOR_{10}$, —$SO_2R_{10}$, —$SO_2N(R_{10})_2$, —C(=O)OCH$_2$SCH$_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula I wherein X is —S—, $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, —$NR_{10}SO_2R_{10}$, —$SOR_{10}$, —$SO_2R_{10}$, —$SO_2N(R_{10})_2$, —C(=O)OCH$_2$SCH$_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments is a compound of Formula I wherein $R_{11}$ is —$OR_{10}$. In further embodiments is a compound of Formula I wherein $R_{11}$ is —$N(R_{10})_2$. In further embodiments is a compound of Formula I wherein $R_{11}$ is —CN. In further embodiments is a compound of Formula I wherein $R_{11}$ is —C(=O)$R_{10}$. In further embodiments is a compound of Formula I wherein $R_{11}$ is —C(=O)$OR_{10}$. In further embodiments is a compound of Formula I wherein $R_{11}$ is —C(=O)$N(R_{10})_2$. In further embodiments is a compound of Formula I wherein $R_{11}$ is —$NR_{10}$C(=O)$R_{10}$. In further embodiments is a compound of Formula I wherein $R_{11}$ is $NR_{10}SO_2R_{10}$. In further embodiments is a compound of Formula I wherein $R_{11}$ is —$SOR_{10}$. In further embodiments is a compound of Formula I wherein $R_{11}$ is —$SO_2R_{10}$. In further embodiments is a compound of Formula I wherein $R_{11}$ is —$SO_2N(R_{10})_2$. In further embodiments is a compound of Formula I wherein $R_{11}$ is —C(=O)OCH$_2$SCH$_3$. In further embodiments is a compound of Formula I wherein $R_{11}$ is $C_1$-$C_6$alkyl. In further embodiments is a compound of Formula I wherein $R_{11}$ is optionally substituted $C_3$-$C_8$cycloalkyl. In further embodiments is a compound of Formula I wherein $R_{11}$ is $C_1$-$C_6$haloalkyl. In further embodiments is a compound of Formula I wherein $R_{11}$ is $C_1$-$C_6$heteroalkyl. In further embodiments is a compound of Formula I wherein $R_{11}$ is —$C_1$-$C_6$alkyl-aryl. In further embodiments is a compound of Formula I wherein $R_{11}$ is optionally substituted aryl. In further embodiments is a compound of Formula I wherein $R_{11}$ is optionally substituted heteroaryl. In yet further embodiments is a compound of Formula I wherein each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments is a compound of Formula I wherein $R_{10}$ is hydrogen. In some embodiments is a compound of Formula I wherein $R_{10}$ is $C_1$-$C_6$alkyl. In some embodiments is a compound of Formula I wherein $R_{10}$ is $C_1$-$C_6$heteroalkyl. In some embodiments is a compound of Formula I wherein $R_{10}$ is —$C_1$-$C_6$alkyl-aryl. In some embodiments is a compound of Formula I wherein $R_{10}$ is aryl. In some embodiments is a compound of Formula I wherein $R_{10}$ is heteroaryl.

In another embodiment is a compound of Formula I wherein X is —S—, $R_2$ is C(=O)$OR_9$, $R_9$ is $C_1$-$C_6$alkyl, and $L_2$ is a bond. In another embodiment is a compound of Formula I wherein X is —S—, $R_2$ is C(=O)$OR_9$, $R_9$ is $C_1$-$C_6$alkyl, $L_2$ is a bond, $L_1$ is a bond and $R_1$ is —CF$_3$. In another embodiment is a compound of Formula I wherein X is —S—, $R_2$ is C(=O)$OR_9$, $R_9$ is $C_1$-$C_6$alkyl, $L_2$ is a bond, $L_1$ is a bond and $R_1$ is $C_1$-$C_6$alkyl. In another embodiment is a compound of Formula I wherein X is —S—, $R_2$ is C(=O)$OR_9$, $R_9$ is $C_1$-$C_6$alkyl, $L_2$ is a bond, $L_1$ is a bond and $R_1$ is C(=O)$OR_8$. In another embodiment is a compound of Formula I wherein X is —S—, $R_2$ is C(=O)$OR_9$, $R_9$ is $C_1$-$C_6$alkyl, $L_2$ is a bond, $L_1$ is a bond and $R_1$ is C(=O)$R_8$. In a further embodiment of the aforementioned embodiments is a compound of Formula I wherein $R_4$ is phenyl substituted with one $R_{11}$. In a further embodiment of the aforementioned embodiments is a compound of Formula I wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula I wherein $R_4$ is phenyl substituted with one $R_{11}$, $R_{11}$ is —$SO_2R_{10}$ and $R_{10}$ is CH$_3$.

In another embodiment is a compound of Formula I wherein X is —S—, $R_2$ is C(=O)$OR_9$, $R_9$ is $C_1$-$C_6$alkyl, and $L_2$ is $C_1$-$C_6$alkyl. In another embodiment is a compound of Formula I wherein X is —S—, $R_2$ is C(=O)$OR_9$, $R_9$ is $C_1$-$C_6$alkyl, $L_2$ is $C_1$-$C_6$alkyl, $L_1$ is a bond and $R_1$ is —CF$_3$. In another embodiment is a compound of Formula I wherein X is —S—, $R_2$ is C(=O)$OR_9$, $R_9$ is $C_1$-$C_6$alkyl, $L_2$ is $C_1$-$C_6$alkyl, $L_1$ is a bond and $R_1$ is $C_1$-$C_6$alkyl. In another embodiment is a compound of Formula I wherein X is —S—, $R_2$ is C(=O)$OR_9$, $R_9$ is $C_1$-$C_6$alkyl, $L_2$ is $C_1$-$C_6$alkyl, $L_1$ is a bond and $R_1$ is C(=O)$OR_8$. In another embodiment is a compound of Formula I wherein X is —S—, $R_2$ is C(=O)$OR_9$, $R_9$ is $C_1$-$C_6$alkyl, $L_2$ is $C_1$-$C_6$alkyl, $L_1$ is a bond and $R_1$ is C(=O)$R_8$. In a further embodiment of the aforementioned embodiments is a compound of Formula I wherein $R_4$ is phenyl substituted with one $R_{11}$. In a further embodiment of the aforementioned embodiments is a compound of Formula I wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula I wherein $R_4$ is phenyl substituted with one $R_{11}$, $R_{11}$ is —$SO_2R_{10}$ and $R_{10}$ is $CH_3$.

In another embodiment of the aforementioned embodiments is a compound of Formula I wherein $R_3$ is hydrogen, halogen, $C_1$-$C_6$alkyl, or $C_1$-$C_6$haloalkyl. In some embodiments of the aforementioned embodiments is a compound of Formula I wherein $R_3$ is hydrogen. In some embodiments of the aforementioned embodiments is a compound of Formula I wherein $R_3$ is halogen. In some embodiments of the aforementioned embodiments is a compound of Formula I wherein $R_3$ is $C_1$-$C_6$alkyl. In some embodiments of the aforementioned embodiments is a compound of Formula I wherein $R_3$ is $C_1$-$C_6$haloalkyl.

In some embodiments is a compound of Formula I wherein X is —CH=CH—. In further embodiments is a compound of Formula I wherein $R_1$ is halogen, —$CF_3$, —$OR_8$, —$N(R_8)_2$, —C(=O)$R_8$, —C(=O)$OR_8$, —C(=O)$N(R_8)_2$, —C(=N—OH)$R_8$, —C(=S)$N(R_8)_2$, $C_1$-$C_6$alkyl, $C_1$-$C_6$heteroalkyl, or optionally substituted $C_2$-$C_7$heterocycloalkyl. In some embodiments is a compound of Formula I wherein $R_1$ is halogen. In some embodiments is a compound of Formula I wherein $R_1$ is —$CF_3$. In some embodiments is a compound of Formula I wherein $R_1$ is —$OR_8$. In some embodiments is a compound of Formula I wherein $R_1$ is —$N(R_8)_2$. In some embodiments is a compound of Formula I wherein $R_1$ is —C(=O)$R_8$. In some embodiments is a compound of Formula I wherein $R_1$ is —C(=O)$OR_8$. In some embodiments is a compound of Formula I wherein $R_1$ is —C(=O)$N(R_8)_2$. In some embodiments is a compound of Formula I wherein $R_1$ is —C(=N—OH)$R_8$. In some embodiments is a compound of Formula I wherein $R_1$ is —C(=S)$N(R_8)_2$. In some embodiments is a compound of Formula I wherein $R_1$ is $C_1$-$C_6$alkyl. In some embodiments is a compound of Formula I wherein $R_1$ is $C_1$-$C_6$heteroalkyl. In some embodiments is a compound of Formula I wherein $R_1$ is optionally substituted $C_2$-$C_7$heterocycloalkyl. In further embodiments is a compound of Formula I wherein $R_8$ is hydrogen, $C_1$-$C_6$alkyl, $C_1$-$C_6$heteroalkyl, —$C_1$-$C_6$alkyl-aryl, aryl, or heteroaryl. In some embodiments is a compound of Formula I wherein $R_8$ is hydrogen. In some embodiments is a compound of Formula I wherein $R_8$ is $C_1$-$C_6$alkyl. In some embodiments is a compound of Formula I wherein $R_8$ is methyl. In some embodiments, $R_8$ is ethyl. In some embodiments is a compound of Formula I wherein $R_8$ is $C_1$-$C_6$heteroalkyl. In some embodiments is a compound of Formula I wherein $R_8$ is —$C_1$-$C_6$alkyl-aryl. In some embodiments is a compound of Formula I wherein $R_8$ is aryl. In some embodiments is a compound of Formula I wherein $R_8$ is heteroaryl.

In some embodiments is a compound of Formula I wherein X is —CH=CH—, $R_2$ is —C(=O)$OR_9$, and $R_9$ is hydrogen, $C_1$-$C_6$alkyl, $C_1$-$C_6$heteroalkyl, —$C_1$-$C_6$alkyl-aryl, aryl, or heteroaryl. In some embodiments is a compound of Formula I wherein X is —CH=CH—, $R_2$ is —C(=O)$OR_9$, and $R_9$ is hydrogen. In some embodiments is a compound of Formula I wherein X is —CH=CH—, $R_2$ is —C(=O)$OR_9$, and $R_9$ is $C_1$-$C_6$alkyl. In some embodiments is a compound of Formula I wherein X is —CH=CH—, $R_2$ is —C(=O)$OR_9$, and $R_9$ is methyl. In some embodiments is a compound of Formula I wherein X is —CH=CH—, $R_2$ is —C(=O)$OR_9$, and $R_9$ is ethyl. In some embodiments is a compound of Formula I wherein X is —CH=CH—, $R_2$ is —C(=O)$OR_9$, and $R_9$ is $C_1$-$C_6$heteroalkyl. In some embodiments is a compound of Formula I wherein X is —CH=CH—, $R_2$ is —C(=O)$OR_9$, and $R_9$ is —$C_1$-$C_6$alkyl-aryl. In some embodiments is a compound of Formula I wherein X is —CH=CH—, $R_2$ is —C(=O)$OR_9$, and $R_9$ is aryl. In some embodiments is a compound of Formula I wherein X is —CH=CH—, $R_2$ is —C(=O)$OR_9$, and $R_9$ is heteroaryl.

In some embodiments is a compound of Formula I wherein X is —CH=CH— and $L_1$ and $L_2$ are each independently a bond, $C_1$-$C_6$alkyl, or $C_1$-$C_6$heteroalkyl; wherein $C_1$-$C_6$alkyl and $C_1$-$C_6$heteroalkyl are optionally substituted with at least one $R_7$. In further embodiments is a compound of Formula I wherein X is —CH=CH—, and $L_1$ and $L_2$ are each a bond. In further embodiments is a compound of Formula I wherein X is —CH=CH—, $L_1$ is a bond, and $L_2$ is $C_1$-$C_6$alkyl optionally substituted with at least one $R_7$. In further embodiments is a compound of Formula I wherein X is —CH=CH—, $L_1$ is a bond, and $L_2$ is $C_1$-$C_6$heteroalkyl optionally substituted with at least one $R_7$. In further embodiments is a compound of Formula I wherein X is —CH=CH—, and $L_1$ and $L_2$ are each $C_1$-$C_6$alkyl optionally substituted with at least one $R_7$. In further embodiments is a compound of Formula I wherein X is —CH=CH—, $L_1$ is $C_1$-$C_6$alkyl optionally substituted with at least one $R_7$, and $L_2$ is a bond. In further embodiments is a compound of Formula I wherein X is —CH=CH—, $L_1$ is $C_1$-$C_6$alkyl optionally substituted with at least one $R_7$, and $L_2$ is $C_1$-$C_6$heteroalkyl optionally substituted with at least one $R_7$. In further embodiments is a compound of Formula I wherein X is —CH=CH—, and $L_1$ and $L_2$ are each $C_1$-$C_6$heteroalkyl optionally substituted with at least one $R_7$. In further embodiments is a compound of Formula I wherein X is —CH=CH—, $L_1$ is $C_1$-$C_6$heteroalkyl optionally substituted with at least one $R_7$, and $L_2$ is a bond. In further embodiments is a compound of Formula I wherein X is —CH=CH—, $L_1$ is $C_1$-$C_6$heteroalkyl optionally substituted with at least one $R_7$, and $L_2$ is $C_1$-$C_6$alkyl optionally substituted with at least one $R_7$. In a further embodiment of the aforementioned embodiments is a compound of Formula I wherein each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments of the aforementioned embodiments is a compound of Formula I wherein each $R_7$ is $C_1$-$C_6$alkyl. In some embodiments of the aforementioned embodiments is a compound of Formula I wherein each $R_7$ is —$C_1$-$C_6$alkyl-aryl. In some embodiments of the aforementioned embodiments is a compound of Formula I wherein each $R_7$ is optionally substituted aryl.

In some embodiments is a compound of Formula I wherein X is —CH=CH— and $R_4$ is aryl or heteroaryl; wherein aryl and heteroaryl are substituted with at least one $R_{11}$. In some embodiments is a compound of Formula I wherein $R_4$ is aryl substituted with one $R_{11}$. In some embodiments is a compound of Formula I wherein $R_4$ is aryl substituted with two $R_{11}$.

In some embodiments is a compound of Formula I wherein $R_4$ is aryl substituted with three $R_{11}$. In further embodiments is a compound of Formula I wherein $R_4$ is phenyl substituted with one $R_{11}$. In further embodiments is a compound of Formula I wherein $R_4$ is phenyl substituted with two $R_{11}$. In further embodiments is a compound of Formula I wherein $R_4$ is phenyl substituted with three $R_{11}$. In some embodiments is a compound of Formula I wherein $R_4$ is heteroaryl substituted with one $R_{11}$. In some embodiments is a compound of Formula I wherein $R_4$ is heteroaryl substituted with two $R_{11}$. In some embodiments is a compound of Formula I wherein $R_4$ is heteroaryl substituted with three $R_{11}$.

In some embodiments is a compound of Formula I wherein X is —CH═CH—, $R_4$ is phenyl substituted with at least one $R_{11}$, and each $R_{11}$ is independently —$OR_{10}$, —$N(R_{10})_2$, —CN, —$C(═O)R_{10}$, —$C(═O)OR_{10}$, —$C(═O)N(R_{10})_2$, —$NR_{10}C(═O)R_{10}$, —$NR_{10}SO_2R_{10}$, —$SOR_{10}$, —$SO_2R_{10}$, —$SO_2N(R_{10})_2$, —C(═O)OCH$_2$SCH$_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula I wherein X is —CH═CH—, $R_4$ is heteroaryl substituted with at least one $R_{11}$, and each $R_{11}$ is independently —$OR_{10}$, —$N(R_{10})_2$, —CN, —$C(═O)R_{10}$, —$C(═O)OR_{10}$, —$C(═O)N(R_{10})_2$, —$NR_{10}C(═O)R_{10}$, —$NR_{10}SO_2R_{10}$, —$SOR_{10}$, —$SO_2R_{10}$, —$SO_2N(R_{10})_2$, —C(═O)OCH$_2$SCH$_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments is a compound of Formula I wherein $R_{11}$ is —$OR_{10}$. In further embodiments is a compound of Formula I wherein $R_{11}$ is —$N(R_{10})_2$. In further embodiments is a compound of Formula I wherein $R_{11}$ is —CN. In further embodiments is a compound of Formula I wherein $R_{11}$ is —$C(═O)R_{10}$. In further embodiments is a compound of Formula I wherein $R_{11}$ is —C(═O)$OR_{10}$. In further embodiments is a compound of Formula I wherein $R_{11}$ is —$C(═O)N(R_{10})_2$. In further embodiments is a compound of Formula I wherein $R_{11}$ is —$NR_{10}C(═O)R_{10}$. In further embodiments is a compound of Formula I wherein $R_{11}$ is $NR_{10}SO_2R_{10}$. In further embodiments is a compound of Formula I wherein $R_{11}$ is —$SOR_{10}$. In further embodiments is a compound of Formula I wherein $R_{11}$ is —$SO_2R_{10}$. In further embodiments is a compound of Formula I wherein $R_{11}$ is —$SO_2N(R_{10})_2$. In further embodiments is a compound of Formula I wherein $R_{11}$ is —C(═O)OCH$_2$SCH$_3$. In further embodiments is a compound of Formula I wherein $R_{11}$ is $C_1$-$C_6$alkyl. In further embodiments is a compound of Formula I wherein $R_{11}$ is optionally substituted $C_3$-$C_8$cycloalkyl. In further embodiments is a compound of Formula I wherein $R_{11}$ is $C_1$-$C_6$haloalkyl. In further embodiments is a compound of Formula I wherein $R_{11}$ is $C_1$-$C_6$heteroalkyl. In further embodiments is a compound of Formula I wherein $R_{11}$ is —$C_1$-$C_6$alkyl-aryl. In further embodiments is a compound of Formula I wherein $R_{11}$ is optionally substituted aryl. In further embodiments is a compound of Formula I wherein $R_{11}$ is optionally substituted heteroaryl. In yet further embodiments is a compound of Formula I wherein each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments is a compound of Formula I wherein $R_{10}$ is hydrogen. In some embodiments is a compound of Formula I wherein $R_{10}$ is $C_1$-$C_6$alkyl. In some embodiments is a compound of Formula I wherein $R_{10}$ is $C_1$-$C_6$heteroalkyl. In some embodiments is a compound of Formula I wherein $R_{10}$ is —$C_1$-$C_6$alkyl-aryl. In some embodiments is a compound of Formula I wherein $R_{10}$ is aryl. In some embodiments is a compound of Formula I wherein $R_{10}$ is heteroaryl.

In another embodiment is a compound of Formula I wherein X is —CH═CH—, $R_2$ is $C(═O)OR_9$, $R_9$ is $C_1$-$C_6$alkyl, and $L_2$ is a bond. In another embodiment is a compound of Formula I wherein X is —CH═CH—, $R_2$ is $C(═O)OR_9$, $R_9$ is $C_1$-$C_6$alkyl, $L_2$ is a bond, $L_1$ is a bond and $R_1$ is —$CF_3$. In another embodiment is a compound of Formula I wherein X is —CH═CH—, $R_2$ is C(═O)$OR_9$, $R_9$ is $C_1$-$C_6$alkyl, $L_2$ is a bond, $L_1$ is a bond and $R_1$ is $C_1$-$C_6$alkyl. In another embodiment is a compound of Formula I wherein X is —CH═CH—, $R_2$ is C(═O)$OR_9$, $R_9$ is $C_1$-$C_6$alkyl, $L_2$ is a bond, $L_1$ is a bond and $R_1$ is $C(═O)OR_8$. In another embodiment is a compound of Formula I wherein X is —CH═CH—, $R_2$ is C(═O)$OR_9$, $R_9$ is $C_1$-$C_6$alkyl, $L_2$ is a bond, $L_1$ is a bond and $R_1$ is $C(═O)R_8$. In a further embodiment of the aforementioned embodiments is a compound of Formula I wherein $R_4$ is phenyl substituted with one $R_{11}$. In a further embodiment of the aforementioned embodiments is a compound of Formula I wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula I wherein $R_4$ is phenyl substituted with one $R_{11}$, $R_{11}$ is —$SO_2R_{10}$ and $R_{10}$ is CH$_3$.

In another embodiment is a compound of Formula I wherein X is —CH═CH—, $R_2$ is $C(═O)OR_9$, $R_9$ is $C_1$-$C_6$alkyl, and $L_2$ is $C_1$-$C_6$alkyl. In another embodiment is a compound of Formula I wherein X is —CH═CH—, $R_2$ is $C(═O)OR_9$, $R_9$ is $C_1$-$C_6$alkyl, $L_2$ is $C_1$-$C_6$alkyl, $L_1$ is a bond and $R_1$ is —$CF_3$. In another embodiment is a compound of Formula I wherein X is —CH═CH—, $R_2$ is C(═O)$OR_9$, $R_9$ is $C_1$-$C_6$alkyl, $L_2$ is $C_1$-$C_6$alkyl, $L_1$ is a bond and $R_1$ is $C_1$-$C_6$alkyl. In another embodiment is a compound of Formula I wherein X is —CH═CH—, $R_2$ is C(═O)$OR_9$, $R_9$ is $C_1$-$C_6$alkyl, $L_2$ is $C_1$-$C_6$alkyl, $L_1$ is a bond and $R_1$ is $C(═O)OR_8$. In another embodiment is a compound of Formula I wherein X is —CH═CH—, $R_2$ is $C(═O)OR_9$, $R_9$ is $C_1$-$C_6$alkyl, $L_2$ is $C_1$-$C_6$alkyl, $L_1$ is a bond and $R_1$ is $C(═O)R_8$. In a further embodiment of the aforementioned embodiments is a compound of Formula I wherein $R_4$ is phenyl substituted with one $R_{11}$. In a further embodiment of the aforementioned embodiments is a compound of Formula I wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula I wherein $R_4$ is phenyl substituted with one $R_{11}$, $R_{11}$ is —$SO_2R_{10}$ and $R_{10}$ is CH$_3$.

In another embodiment of the aforementioned embodiments is a compound of Formula I wherein $R_3$ is hydrogen, halogen, $C_1$-$C_6$alkyl, or $C_1$-$C_6$haloalkyl. In some embodiments of the aforementioned embodiments is a compound of Formula I wherein $R_3$ is hydrogen. In some embodiments of the aforementioned embodiments is a compound of Formula I wherein $R_3$ is halogen. In some embodiments of the aforementioned embodiments is a compound of Formula I wherein $R_3$ is $C_1$-$C_6$alkyl. In some embodiments of the aforementioned embodiments is a compound of Formula I wherein $R_3$ is $C_1$-$C_6$haloalkyl.

In some embodiments is a compound of Formula I, wherein X is —CH═CH—; and $L_2$ is $C_1$-$C_6$alkyl. In some embodiments is a compound of Formula I, wherein X is —CH═CH—; and $L_2$ is —CH$_2$—. In some embodiments is a compound of Formula I, wherein X is —CH═CH—; $R_2$ is —C(═O)$OR_9$; and $R_9$ is H or $C_1$-$C_6$alkyl. In some embodiments is a compound of Formula I, wherein X is —CH═CH—; $R_9$ is hydrogen, methyl or ethyl. In some embodiments is a compound of Formula I, wherein X is —CH═CH—; and $L_1$ is a bond. In some embodiments is a compound of Formula I, wherein X is —CH═CH—; and $R_1$ is $C_1$-$C_6$ alkyl or —$CF_3$. In some embodiments is a compound of Formula I, wherein X is —CH═CH—; and $L_1$ is $C_1$-$C_6$ alkyl; and $R_1$ is —$OR_8$. In some embodiments is a compound of Formula I, wherein X is —CH═CH—; and -$L_1$-$R_1$ is isopropyl, —$CF_3$, and —$C(CH_3)_2$OH.

In some embodiments is a compound of Formula I, wherein X is —CH═CH—; and $R_4$ is phenyl substituted with at least one $R_{11}$. In some embodiments is a compound of Formula I, wherein X is —CH═CH—; and at least one $R_{11}$ is —NR$_{10}$SO$_2$R$_{10}$, —SOR$_{10}$, —SO$_2$R$_{10}$, or —SO$_2$N(R$_{10}$)$_2$. In some embodiments is a compound of Formula I, wherein X is —CH═CH—; and at least one $R_{11}$ is —SO$_2$R$_{10}$. In some embodiments is a compound of Formula I, wherein X is —CH═CH—; and each $R_{10}$ is independently $C_1$-$C_6$ alkyl. In some embodiments is a compound of Formula I, wherein X is —CH═CH—; and each $R_{10}$ is methyl. In some embodiments is a compound of Formula I, wherein X is —CH═CH—; and $R_4$ is phenyl substituted with one $R_{11}$, wherein $R_{11}$ is —SO$_2$R$_{10}$ and $R_{10}$ is $C_1$-$C_6$alkyl; or $R_4$ is phenyl substituted with two $R_{11}$, and one $R_{11}$ is —SO$_2$R$_{10}$ and one $R_{11}$ is optionally substituted $C_1$-$C_6$alkyl. In some embodiments is a compound of Formula I, wherein X is —CH═CH—; and $R_4$ is phenyl substituted with one $R_{11}$, wherein $R_{11}$ is —SO$_2$R$_{10}$ and $R_{10}$ is $C_1$-$C_6$alkyl. In some embodiments is a compound of Formula I, wherein X is —CH═CH—; and $R_4$ is phenyl substituted with one $R_{11}$, wherein $R_{11}$ is —SO$_2$R$_{10}$ and $R_{10}$ is methyl. In some embodiments is a compound of Formula I, wherein X is —CH═CH—; and $R_4$ is phenyl substituted with two $R_{11}$, wherein one $R_{11}$ is —SO$_2$CH$_3$ and one $R_{11}$ is —CH$_2$OH. In some embodiments is a compound of Formula I, wherein X is —CH═CH—; and "optionally substituted" means optionally substituted by 1, 2, 3, or 4 substituents independently selected from halo, cyano, $C_1$-$C_4$ alkyl, $C_2$-$C_4$ alkenyl, hydoxy, $C_1$-$C_4$ alkoxy, $C_1$-$C_4$ haloalkyl, $C_1$-$C_4$ haloalkoxy, amino, $C_1$-$C_4$ alkylamino, and di($C_1$-$C_4$ alkyl) amino.

In some embodiments is a compound of Formula I, wherein X is —CH═CH—; and n is 0. In some embodiments is a compound of Formula I, wherein X is —CH═CH—; and $R_3$ is hydrogen.

In some embodiments, the compound is a compound of Formula (IA):

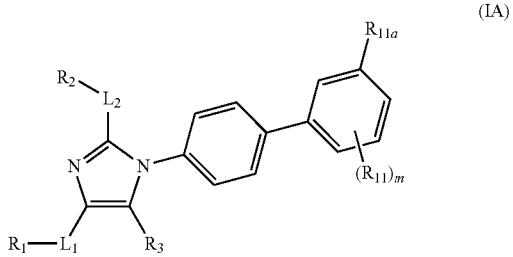

wherein:
m is 0 or 1; and
$R_{11a}$ is —NR$_{10}$SO$_2$R$_{10}$, —SOR$_{10}$, —SO$_2$R$_{10}$, or —SO$_2$N(R$_{10}$)$_2$;
or a pharmaceutically acceptable salt thereof.

In some embodiments, the compound is a compound of Formula (IB):

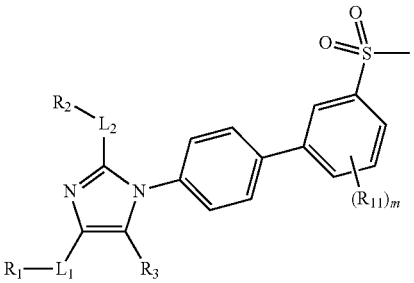

wherein m is 0 or 1;
or a pharmaceutically acceptable salt thereof.

In some embodiments of the compound of Formula (I):
X is —CH═CH—;
$L_2$ is $C_1$-$C_6$alkyl;
$R_2$ is —C(═O)OR$_9$;
$R_9$ is hydrogen or $C_1$-$C_6$alkyl;
$L_1$ is a bond; and $R_1$ is $C_1$-$C_6$ alkyl or —CF$_3$; or
$L_1$ is $C_1$-$C_6$ alkyl; and $R_1$ is —OR$_8$;
$R_4$ is phenyl substituted with at least one $R_{11}$;
each $R_{11}$ is independently $C_1$-$C_6$ alkyl, —NR$_{10}$SO$_2$R$_{10}$, —SOR$_{10}$, —SO$_2$R$_{10}$, or —SO$_2$N(R$_{10}$)$_2$; wherein said $C_1$-$C_6$ alkyl is optionally substituted by 1 hydroxy;
provided that at least one $R_{11}$ is —NR$_{10}$SO$_2$R$_{10}$, —SOR$_{10}$, —SO$_2$R$_{10}$, or —SO$_2$N(R$_{10}$)$_2$;
each $R_{10}$ is independently $C_1$-$C_6$ alkyl;
n is 0; and
$R_3$ is hydrogen.

In some embodiments of the compound of Formula (I):
X is —CH═CH—;
$L_2$ is $C_1$-$C_6$alkyl;
$R_2$ is —C(═O)OR$_9$;
$R_9$ is hydrogen or $C_1$-$C_6$alkyl;
$L_1$ is a bond; and $R_1$ is $C_1$-$C_6$ alkyl or —CF$_3$; or
$L_1$ is $C_1$-$C_6$ alkyl; and $R_1$ is —OR$_8$;
$R_4$ is phenyl substituted with at least one $R_{11}$;
each $R_{11}$ is independently $C_1$-$C_6$ alkyl or —SO$_2$R$_{10}$;
wherein said $C_1$-$C_6$ alkyl is optionally substituted by 1 hydroxy;
provided that at least one $R_{11}$ is —SO$_2$R$_{10}$;
each $R_{10}$ is independently $C_1$-$C_6$ alkyl;
n is 0; and
$R_3$ is hydrogen.

In some embodiments, the compound is selected from:

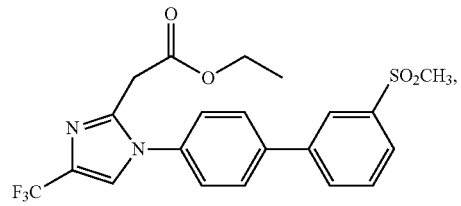

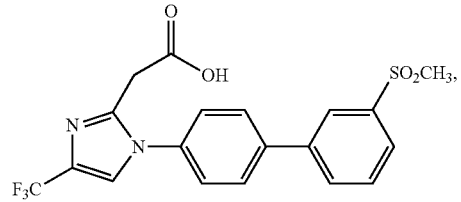

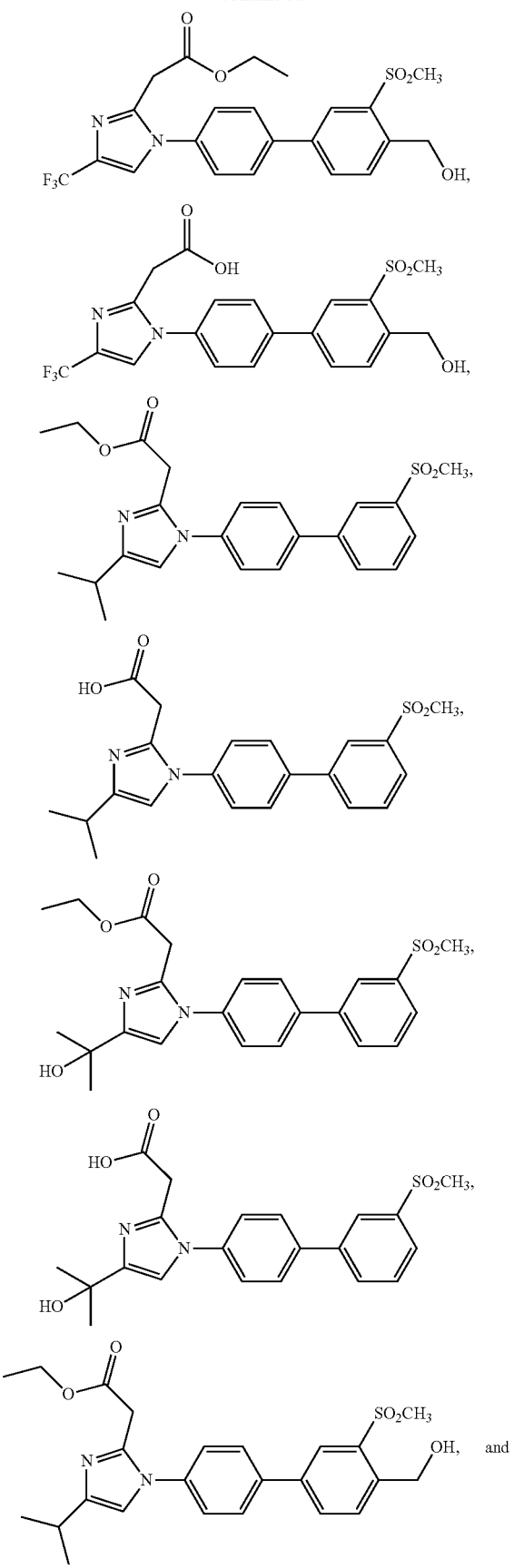

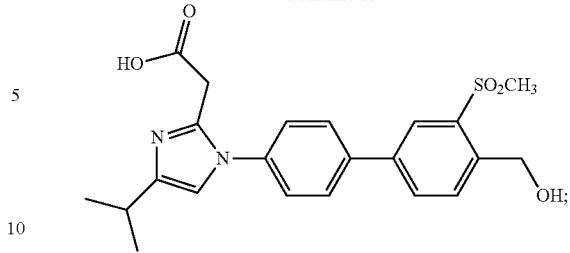

or a pharmaceutically acceptable salt thereof.

In another aspect is a compound of Formula (II):

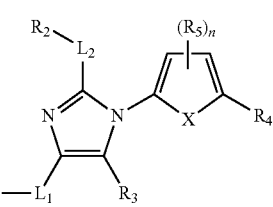

wherein:

X is —O—, —S—, or —C($R_6$)=C($R_6$)—;

$L_1$ is a bond, $C_1$-$C_6$alkyl, or $C_1$-$C_6$heteroalkyl; wherein $C_1$-$C_6$alkyl and $C_1$-$C_6$heteroalkyl are optionally substituted with at least one $R_7$;

$L_2$ is a $C_1$-$C_6$alkyl, or $C_1$-$C_6$heteroalkyl;

$R_1$ is —C(=O)O$R_8$;

$R_2$ is hydrogen, —O$R_9$, —N($R_9$)$_2$, —C(=O)$R_9$, —C(=O)N($R_9$)$_2$, —C(=N—OH)$R_9$, —C(=S)N($R_9$)$_2$, $C_1$-$C_6$alkyl, $C_3$-$C_8$cycloalkyl, $C_1$-$C_6$haloalkyl, $C_1$-$C_6$heteroalkyl, or optionally substituted heterocycloalkyl;

$R_3$ is hydrogen, halogen, $C_1$-$C_6$alkyl, or $C_1$-$C_6$haloalkyl;

$R_4$ is aryl or heteroaryl; wherein aryl and heteroaryl are substituted with at least one $R_{11}$;

each $R_5$ is independently halogen, $C_1$-$C_6$alkyl, or $C_1$-$C_6$haloalkyl;

each $R_6$ is independently hydrogen, halogen, $C_1$-$C_6$alkyl, or $C_1$-$C_6$haloalkyl;

each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;

each $R_8$, each $R_9$, and each $R_{10}$ are each independently hydrogen, $C_1$-$C_6$alkyl, $C_1$-$C_6$heteroalkyl, —$C_1$-$C_6$alkyl-aryl, aryl, or heteroaryl;

each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —N$R_{10}$C(=O)$R_{10}$, —N$R_{10}$SO$_2$$R_{10}$, —SO$R_{10}$, —SO$_2$$R_{10}$, —SO$_2$N($R_{10}$)$_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and n is 0-2;

or a pharmaceutically acceptable salt, pharmaceutically acceptable solvate, or pharmaceutically acceptable prodrug thereof.

In some embodiments is a compound of Formula II wherein X is —O—. In a further embodiment is a compound of Formula II wherein $L_2$ is $C_1$-$C_6$alkyl. In yet a further embodiment is a compound of Formula II wherein $R_2$ is hydrogen, —$OR_9$, —$N(R_9)_2$, —$C(=O)R_9$, —$C(=O)N(R_9)_2$, —$C(=N$—$OH)R_9$, —$C(=S)N(R_9)_2$, $C_1$-$C_6$alkyl, $C_3$-$C_8$cycloalkyl, $C_1$-$C_6$haloalkyl, $C_1$-$C_6$heteroalkyl, or optionally substituted heterocycloalkyl, or optionally substituted heterocycloalkyl. In some embodiments is a compound of Formula II wherein $R_2$ is —$OR_9$. In some embodiments is a compound of Formula II wherein $R_2$ is —$N(R_9)_2$. In some embodiments is a compound of Formula II wherein $R_2$ is —$C(=O)R_9$. In some embodiments is a compound of Formula II wherein $R_2$ is —$C(=O)N(R_9)_2$. In some embodiments is a compound of Formula II wherein $R_2$ is —$C(=N$—$OH)R_9$. In some embodiments is a compound of Formula II wherein $R_2$ is —$C(=S)N(R_9)_2$. In some embodiments is a compound of Formula II wherein $R_2$ is $C_1$-$C_6$alkyl. In some embodiments is a compound of Formula II wherein $R_2$ is $C_3$-$C_8$cycloalkyl. In some embodiments is a compound of Formula II wherein $R_2$ is $C_1$-$C_6$haloalkyl. In some embodiments is a compound of Formula II wherein $R_2$ is $C_1$-$C_6$heteroalkyl. In some embodiments is a compound of Formula II wherein $R_2$ is optionally substituted $C_2$-$C_7$heterocycloalkyl. In further embodiments is a compound of Formula II wherein $R_9$ is hydrogen, $C_1$-$C_6$alkyl, $C_1$-$C_6$heteroalkyl, —$C_1$-$C_6$alkyl-aryl, aryl, or heteroaryl. In some embodiments is a compound of Formula II wherein $R_9$ is hydrogen. In some embodiments is a compound of Formula II wherein $R_9$ is $C_1$-$C_6$alkyl. In some embodiments is a compound of Formula II wherein $R_9$ is methyl. In some embodiments, $R_9$ is ethyl. In some embodiments is a compound of Formula II wherein $R_9$ is $C_1$-$C_6$heteroalkyl. In some embodiments is a compound of Formula II wherein $R_9$ is —$C_1$-$C_6$alkyl-aryl. In some embodiments is a compound of Formula II wherein $R_9$ is aryl. In some embodiments is a compound of Formula II wherein $R_9$ is heteroaryl.

In some embodiments is a compound of Formula II wherein X is —O—, $R_1$ is —$C(=O)OR_8$, and $R_8$ is hydrogen, $C_1$-$C_6$alkyl, $C_1$-$C_6$heteroalkyl, —$C_1$-$C_6$alkyl-aryl, aryl, or heteroaryl. In some embodiments is a compound of Formula II wherein X is —O—, $R_1$ is —$C(=O)OR_8$, and $R_8$ is hydrogen. In some embodiments is a compound of Formula II wherein X is —O—, $R_1$ is —$C(=O)OR_8$, and $R_8$ is $C_1$-$C_6$alkyl. In some embodiments is a compound of Formula II wherein X is —O—, $R_1$ is —$C(=O)OR_8$, and $R_8$ is methyl. In some embodiments is a compound of Formula II wherein X is —O—, $R_1$ is —$C(=O)OR_8$, and $R_8$ is ethyl. In some embodiments is a compound of Formula II wherein X is —O—, $R_1$ is —$C(=O)OR_8$, and $R_8$ is $C_1$-$C_6$heteroalkyl. In some embodiments is a compound of Formula II wherein X is —O—, $R_1$ is —$C(=O)OR_8$, and $R_8$ is —$C_1$-$C_6$alkyl-aryl. In some embodiments is a compound of Formula II wherein X is —O—, $R_1$ is —$C(=O)OR_8$, and $R_8$ is aryl. In some embodiments is a compound of Formula II wherein X is —O—, $R_1$ is —$C(=O)OR_8$, and $R_8$ is heteroaryl.

In some embodiments is a compound of Formula II wherein X is —O—, $L_1$ is a bond, $C_1$-$C_6$alkyl, or $C_1$-$C_6$heteroalkyl wherein $C_1$-$C_6$alkyl and $C_1$-$C_6$heteroalkyl are optionally substituted with at least one $R_7$, and $L_2$ is $C_1$-$C_6$alkyl, or $C_1$-$C_6$heteroalkyl. In a further embodiment is a compound of Formula II wherein X is —O—, $L_1$ is a bond, and $L_2$ is a $C_1$-$C_6$alkyl. In a further embodiment is a compound of Formula II wherein X is —O—, $L_1$ is $C_1$-$C_6$alkyl optionally substituted with at least one $R_7$, and $L_2$ is a $C_1$-$C_6$alkyl. In further embodiments is a compound of Formula II wherein X is —O—, $L_1$ is $C_1$-$C_6$heteroalkyl optionally substituted with at least one $R_7$, and $L_2$ is $C_1$-$C_6$alkyl. In further embodiments is a compound of Formula II wherein X is —O—, $L_1$ is a bond, and $L_2$ is $C_1$-$C_6$heteroalkyl. In further embodiments is a compound of Formula II wherein X is —O—, $L_1$ is $C_1$-$C_6$alkyl optionally substituted with at least one $R_7$, and $L_2$ is $C_1$-$C_6$heteroalkyl. In further embodiments is a compound of Formula II wherein X is —O—, $L_1$ is $C_1$-$C_6$heteroalkyl optionally substituted with at least one $R_7$, and $L_2$ is $C_1$-$C_6$heteroalkyl. In a further embodiment of the aforementioned embodiments is a compound of Formula II wherein each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments of the aforementioned embodiments is a compound of Formula II wherein each $R_7$ is $C_1$-$C_6$alkyl. In some embodiments of the aforementioned embodiments is a compound of Formula II wherein each $R_7$ is —$C_1$-$C_6$alkyl-aryl. In some embodiments of the aforementioned embodiments is a compound of Formula II wherein each $R_7$ is optionally substituted aryl.

In some embodiments is a compound of Formula II wherein X is —O— and $R_4$ is aryl or heteroaryl; wherein aryl and heteroaryl are substituted with at least one $R_{11}$. In some embodiments is a compound of Formula II wherein $R_4$ is aryl substituted with one $R_{11}$. In some embodiments is a compound of Formula II wherein $R_4$ is aryl substituted with two $R_{11}$. In some embodiments is a compound of Formula II wherein $R_4$ is aryl substituted with three $R_{11}$. In further embodiments is a compound of Formula II wherein $R_4$ is phenyl substituted with one $R_{11}$. In further embodiments is a compound of Formula II wherein $R_4$ is phenyl substituted with two $R_{11}$. In further embodiments is a compound of Formula II wherein $R_4$ is phenyl substituted with three $R_{11}$. In some embodiments is a compound of Formula II wherein $R_4$ is heteroaryl substituted with one $R_{11}$. In some embodiments is a compound of Formula II wherein $R_4$ is heteroaryl substituted with two $R_{11}$. In some embodiments is a compound of Formula II wherein $R_4$ is heteroaryl substituted with three $R_{11}$.

In some embodiments is a compound of Formula II wherein X is —O—, $R_4$ is phenyl substituted with at least one $R_{11}$, and each $R_{11}$ is independently —$OR_{10}$, —$N(R_{10})_2$, —CN, —$C(=O)R_{10}$, —$C(=O)OR_{10}$, —$C(=O)N(R_{10})_2$, —$NR_{10}C(=O)R_{10}$, —$NR_{10}SO_2R_{10}$, —$SOR_{10}$, —$SO_2R_{10}$, —$SO_2N(R_{10})_2$, —$C(=O)OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula II wherein X is —O—, $R_4$ is heteroaryl substituted with at least one $R_{11}$, and each $R_{11}$ is independently —$OR_{10}$, —$N(R_{10})_2$, —CN, —$C(=O)R_{10}$, —$C(=O)OR_{10}$, —$C(=O)N(R_{10})_2$, —$NR_{10}C(=O)R_{10}$, —$NR_{10}SO_2R_{10}$, —$SOR_{10}$, —$SO_2R_{10}$, —$SO_2N(R_{10})_2$, —$C(=O)OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments is a compound of Formula II wherein $R_{11}$ is —$OR_{10}$. In further embodiments is a compound of Formula II wherein $R_{11}$ is —$N(R_{10})_2$. In further embodiments is a compound of Formula II wherein $R_{11}$ is —CN. In further embodiments is a compound of Formula II wherein $R_{11}$ is —$C(=O)R_{10}$. In further embodiments is a compound of Formula II wherein $R_{11}$ is —$C(=O)OR_{10}$. In further embodiments is a compound of Formula II wherein $R_{11}$ is —$C(=O)N(R_{10})_2$. In further embodiments is a compound of Formula II wherein $R_{11}$ is —$NR_{10}C(=O)R_{10}$. In further embodiments is a compound of Formula II wherein $R_{11}$ is $NR_{10}SO_2R_{10}$. In further embodiments is a compound of Formula II wherein $R_{11}$ is —$SOR_{10}$. In further embodiments is a compound of Formula II wherein $R_{11}$ is —$SO_2R_{10}$. In further embodiments is a compound of Formula II wherein $R_{11}$ is —$SO_2N(R_{10})_2$. In further embodiments is a compound of Formula II wherein $R_{11}$ is —$C(=O)OCH_2SCH_3$. In further embodiments is a compound of Formula II wherein $R_{11}$ is $C_1$-$C_6$alkyl. In further embodiments is a compound of Formula II wherein $R_{11}$ is optionally substituted $C_3$-$C_8$cycloalkyl. In further embodiments is a compound of Formula II wherein $R_{11}$ is $C_1$-$C_6$haloalkyl. In further embodiments is a compound of Formula II wherein $R_{11}$ is $C_1$-$C_6$heteroalkyl. In further embodiments is a compound of Formula II wherein $R_{11}$ is —$C_1$-$C_6$alkyl-aryl. In further embodiments is a compound of Formula II wherein $R_{11}$ is optionally substituted aryl. In further embodiments is a compound of Formula II wherein $R_{11}$ is optionally substituted heteroaryl. In yet further embodiments is a compound of Formula II wherein each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments is a compound of Formula II wherein $R_{10}$ is hydrogen. In some embodiments is a compound of Formula II wherein $R_{10}$ is $C_1$-$C_6$alkyl. In some embodiments is a compound of Formula II wherein $R_{10}$ is $C_1$-$C_6$heteroalkyl. In some embodiments is a compound of Formula II wherein $R_{10}$ is —$C_1$-$C_6$alkyl-aryl. In some embodiments is a compound of Formula II wherein $R_{10}$ is aryl. In some embodiments is a compound of Formula II wherein $R_{10}$ is heteroaryl.

In another embodiment is a compound of Formula II wherein X is —O—, $R_1$ is $C(=O)OR_8$, $R_8$ is $C_1$-$C_6$alkyl, and $L_1$ is a bond. In another embodiment is a compound of Formula II wherein X is —O—, $R_1$ is $C(=O)OR_8$, $R_8$ is $C_1$-$C_6$alkyl, $L_1$ is a bond, $L_2$ is a $C_1$-$C_6$alkyl and $R_2$ is hydrogen. In another embodiment is a compound of Formula II wherein X is —O—, $R_1$ is $C(=O)OR_8$, $R_8$ is $C_1$-$C_6$alkyl, $L_1$ is a bond, $L_2$ is a $C_1$-$C_6$alkyl and $R_2$ is $C_3$-$C_8$cyclolkyl. In another embodiment is a compound of Formula II wherein X is —O—, $R_1$ is $C(=O)OR_8$, $R_8$ is $C_1$-$C_6$alkyl, $L_1$ is a bond, $L_2$ is $C_1$-$C_6$alkyl and $R_2$ is $C_1$-$C_6$heteroalkyl. In another embodiment is a compound of Formula II wherein X is —O—, $R_1$ is $C(=O)OR_8$, $R_8$ is $C_1$-$C_6$alkyl, $L_1$ is a bond, $L_2$ is $C_1$-$C_6$alkyl and $R_2$ is optionally substituted heterocycloalkyl. In a further embodiment of the aforementioned embodiments is a compound of Formula II wherein $R_4$ is phenyl substituted with one $R_{11}$. In a further embodiment of the aforementioned embodiments is a compound of Formula II wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula II wherein $R_4$ is phenyl substituted with one $R_{11}$, $R_{11}$ is —$SO_2R_{10}$ and $R_{10}$ is $CH_3$.

In another embodiment is a compound of Formula II wherein X is —O—, $R_1$ is $C(=O)OR_8$, $R_8$ is $C_1$-$C_6$alkyl, and $L_1$ is $C_1$-$C_6$alkyl. In another embodiment is a compound of Formula II wherein X is —O—, $R_1$ is $C(=O)OR_8$, $R_8$ is $C_1$-$C_6$alkyl, $L_1$ is $C_1$-$C_6$alkyl, $L_2$ is a $C_1$-$C_6$alkyl and $R_2$ is hydrogen. In another embodiment is a compound of Formula II wherein X is —O—, $R_1$ is $C(=O)OR_8$, $R_8$ is $C_1$-$C_6$alkyl, $L_1$ is $C_1$-$C_6$alkyl, $L_2$ is a $C_1$-$C_6$alkyl and $R_2$ is $C_3$-$C_8$cyclolkyl. In another embodiment is a compound of Formula II wherein X is —O—, $R_1$ is $C(=O)OR_8$, $R_8$ is $C_1$-$C_6$alkyl, $L_1$ is $C_1$-$C_6$alkyl, $L_2$ is $C_1$-$C_6$alkyl and $R_2$ is $C_1$-$C_6$heteroalkyl. In another embodiment is a compound of Formula II wherein X is —O—, $R_1$ is $C(=O)OR_8$, $R_8$ is $C_1$-$C_6$alkyl, $L_1$ is $C_1$-$C_6$alkyl, $L_2$ is $C_1$-$C_6$alkyl and $R_2$ is optionally substituted heterocycloalkyl. In a further embodiment of the aforementioned embodiments is a compound of Formula II wherein $R_4$ is phenyl substituted with one $R_{11}$. In a further embodiment of the aforementioned embodiments is a compound of Formula II wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula II wherein $R_4$ is phenyl substituted with one $R_{11}$, $R_{11}$ is —$SO_2R_{10}$ and $R_{10}$ is $CH_3$.

In another embodiment of the aforementioned embodiments is a compound of Formula II wherein $R_3$ is hydrogen, halogen, $C_1$-$C_6$alkyl, or $C_1$-$C_6$haloalkyl. In some embodiments of the aforementioned embodiments is a compound of Formula II wherein $R_3$ is hydrogen. In some embodiments of the aforementioned embodiments is a compound of Formula II wherein $R_3$ is halogen. In some embodiments of the aforementioned embodiments is a compound of Formula II wherein $R_3$ is $C_1$-$C_6$alkyl. In some embodiments of the aforementioned embodiments is a compound of Formula II wherein $R_3$ is $C_1$-$C_6$haloalkyl.

In some embodiments is a compound of Formula II wherein X is —S—. In a further embodiment is a compound of Formula II wherein $L_2$ is $C_1$-$C_6$alkyl. In yet a further embodiment is a compound of Formula II wherein $R_2$ is hydrogen, —$OR_9$, —$N(R_9)_2$, —$C(=O)R_9$, —$C(=O)N(R_9)_2$, —$C(=N-OH)R_9$, —$C(=S)N(R_9)_2$, $C_1$-$C_6$alkyl, $C_3$-$C_8$cycloalkyl, $C_1$-$C_6$haloalkyl, $C_1$-$C_6$heteroalkyl, or optionally substituted heterocycloalkyl. In some embodiments is a compound of Formula II wherein $R_2$ is —$OR_9$. In some embodiments is a compound of Formula II wherein $R_2$ is —$N(R_9)_2$. In some embodiments is a compound of Formula II wherein $R_2$ is —$C(=O)R_9$. In some embodiments is a compound of Formula II wherein $R_2$ is —$C(=O)N(R_9)_2$. In some embodiments is a compound of Formula II wherein $R_2$ is —$C(=N-OH)R_9$. In some embodiments is a compound of Formula II wherein $R_2$ is —$C(=S)N(R_9)_2$. In some embodiments is a compound of Formula II wherein $R_2$ is $C_1$-$C_6$alkyl. In some embodiments is a compound of Formula II wherein $R_2$ is $C_3$-$C_8$cycloalkyl. In some embodiments is a compound of Formula II wherein $R_2$ is $C_1$-$C_6$haloalkyl. In some embodiments is a compound of Formula II wherein $R_2$ is $C_1$-$C_6$heteroalkyl. In some embodiments is a compound of Formula II wherein $R_2$ is optionally substituted $C_2$-$C_7$heterocycloalkyl. In further embodiments is a compound of Formula II wherein $R_9$ is hydrogen, $C_1$-$C_6$alkyl, $C_1$-$C_6$heteroalkyl, —$C_1$-$C_6$alkyl-aryl, aryl, or heteroaryl. In some embodiments is a compound of Formula II wherein $R_9$ is hydrogen. In some embodiments is a compound of Formula II wherein $R_8$ is $C_1$-$C_6$alkyl. In some embodiments is a compound of Formula II wherein $R_9$ is methyl. In some embodiments, $R_9$ is ethyl. In some embodiments is a compound of Formula II wherein $R_9$ is $C_1$-$C_6$heteroalkyl. In some embodiments is a compound of Formula II wherein $R_9$ is —$C_1$-$C_6$alkyl-aryl. In some embodiments is a compound of Formula II wherein $R_9$ is aryl. In some embodiments is a compound of Formula II wherein $R_9$ is heteroaryl.

In some embodiments is a compound of Formula II wherein X is —S—, $R_1$ is —$C(=O)OR_8$, and $R_8$ is hydrogen, $C_1$-$C_6$alkyl, $C_1$-$C_6$heteroalkyl, —$C_1$-$C_6$alkyl-aryl, aryl, or heteroaryl. In some embodiments is a compound of Formula II wherein X is —S—, $R_1$ is —$C(=O)OR_8$, and $R_8$ is hydrogen. In some embodiments is a compound of Formula II wherein X is —S—, $R_1$ is —$C(=O)OR_8$, and $R_8$ is $C_1$-$C_6$alkyl. In some embodiments is a compound of Formula II wherein X is —S—, $R_1$ is —$C(=O)OR_8$, and $R_8$ is methyl. In some embodiments is a compound of Formula II wherein X is —S—, $R_1$ is —$C(=O)OR_8$, and $R_8$ is ethyl. In some embodiments is a compound of Formula II wherein X is —S—, $R_1$ is —C(=O)$OR_8$, and $R_8$ is $C_1$-$C_6$heteroalkyl. In some embodiments is a compound of Formula II wherein X is —S—, $R_1$ is —C(=O)$OR_8$, and $R_8$ is —$C_1$-$C_6$alkyl-aryl. In some embodiments is a compound of Formula II wherein X is —S—, $R_1$ is —C(=O)$OR_8$, and $R_8$ is aryl. In some embodiments is a compound of Formula II wherein X is —S—, $R_1$ is —C(=O)$OR_8$, and $R_8$ is heteroaryl.

In some embodiments is a compound of Formula II wherein X is —S—, $L_1$ is a bond, $C_1$-$C_6$alkyl, or $C_1$-$C_6$heteroalkyl wherein $C_1$-$C_6$alkyl and $C_1$-$C_6$heteroalkyl are optionally substituted with at least one $R_7$, and $L_2$ is $C_1$-$C_6$alkyl, or $C_1$-$C_6$heteroalkyl. In a further embodiment is a compound of Formula II wherein X is —S—, $L_1$ is a bond, and $L_2$ is a $C_1$-$C_6$alkyl. In a further embodiment is a compound of Formula II wherein X is —S—, $L_1$ is $C_1$-$C_6$alkyl optionally substituted with at least one $R_7$, and $L_2$ is a $C_1$-$C_6$alkyl. In further embodiments is a compound of Formula II wherein X is —S—, $L_1$ is $C_1$-$C_6$heteroalkyl optionally substituted with at least one $R_7$, and $L_2$ is $C_1$-$C_6$alkyl. In further embodiments is a compound of Formula II wherein X is —S—, $L_1$ is a bond, and $L_2$ is $C_1$-$C_6$heteroalkyl. In further embodiments is a compound of Formula II wherein X is —S—, $L_1$ is $C_1$-$C_6$alkyl optionally substituted with at least one $R_7$, and $L_2$ is $C_1$-$C_6$heteroalkyl. In further embodiments is a compound of Formula II wherein X is —S—, $L_1$ is $C_1$-$C_6$heteroalkyl optionally substituted with at least one $R_7$, and $L_2$ is $C_1$-$C_6$heteroalkyl. In a further embodiment of the aforementioned embodiments is a compound of Formula II wherein each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments of the aforementioned embodiments is a compound of Formula II wherein each $R_7$ is $C_1$-$C_6$alkyl. In some embodiments of the aforementioned embodiments is a compound of Formula II wherein each $R_7$ is —$C_1$-$C_6$alkyl-aryl. In some embodiments of the aforementioned embodiments is a compound of Formula II wherein each $R_7$ is optionally substituted aryl.

In some embodiments is a compound of Formula II wherein X is —S— and $R_4$ is aryl or heteroaryl; wherein aryl and heteroaryl are substituted with at least one $R_{11}$. In some embodiments is a compound of Formula II wherein $R_4$ is aryl substituted with one $R_{11}$. In some embodiments is a compound of Formula II wherein $R_4$ is aryl substituted with two $R_{11}$. In some embodiments is a compound of Formula II wherein $R_4$ is aryl substituted with three $R_{11}$. In further embodiments is a compound of Formula II wherein $R_4$ is phenyl substituted with one $R_{11}$. In further embodiments is a compound of Formula II wherein $R_4$ is phenyl substituted with two $R_{11}$. In further embodiments is a compound of Formula II wherein $R_4$ is phenyl substituted with three $R_{11}$. In some embodiments is a compound of Formula II wherein $R_4$ is heteroaryl substituted with one $R_{11}$. In some embodiments is a compound of Formula II wherein $R_4$ is heteroaryl substituted with two $R_{11}$. In some embodiments is a compound of Formula II wherein $R_4$ is heteroaryl substituted with three $R_{11}$.

In some embodiments is a compound of Formula II wherein X is —S—, $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, —$NR_{10}$$SO_2$$R_{10}$, —$SOR_{10}$, —$SO_2$$R_{10}$, —$SO_2$$N(R_{10})_2$, —C(=O)$OCH_2$$SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula II wherein X is —S—, $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, —$NR_{10}$$SO_2$$R_{10}$, —$SOR_{10}$, —$SO_2$$R_{10}$, —$SO_2$$N(R_{10})_2$, —C(=O)$OCH_2$$SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments is a compound of Formula II wherein $R_{11}$ is —$OR_{10}$. In further embodiments is a compound of Formula II wherein $R_{11}$ is —$N(R_{10})_2$. In further embodiments is a compound of Formula II wherein $R_{11}$ is —CN. In further embodiments is a compound of Formula II wherein $R_{11}$ is —C(=O)$R_{10}$. In further embodiments is a compound of Formula II wherein $R_{11}$ is —C(=O)$OR_{10}$. In further embodiments is a compound of Formula II wherein $R_{11}$ is —C(=O)$N(R_{10})_2$. In further embodiments is a compound of Formula II wherein $R_{11}$ is —$NR_{10}$C(=O)$R_{10}$. In further embodiments is a compound of Formula II wherein $R_{11}$ is $NR_{10}$$SO_2$$R_{10}$. In further embodiments is a compound of Formula II wherein $R_{11}$ is —$SOR_{10}$. In further embodiments is a compound of Formula II wherein $R_{11}$ is —$SO_2$$R_{10}$. In further embodiments is a compound of Formula II wherein $R_{11}$ is —$SO_2$$N(R_{10})_2$. In further embodiments is a compound of Formula II wherein $R_{11}$ is —C(=O)$OCH_2$$SCH_3$. In further embodiments is a compound of Formula II wherein $R_{11}$ is $C_1$-$C_6$alkyl. In further embodiments is a compound of Formula II wherein $R_{11}$ is optionally substituted $C_3$-$C_8$cycloalkyl. In further embodiments is a compound of Formula II wherein $R_{11}$ is $C_1$-$C_6$haloalkyl. In further embodiments is a compound of Formula II wherein $R_{11}$ is $C_1$-$C_6$heteroalkyl. In further embodiments is a compound of Formula II wherein $R_{11}$ is —$C_1$-$C_6$alkyl-aryl. In further embodiments is a compound of Formula II wherein $R_{11}$ is optionally substituted aryl. In further embodiments is a compound of Formula II wherein $R_{11}$ is optionally substituted heteroaryl. In yet further embodiments is a compound of Formula II wherein each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments is a compound of Formula II wherein $R_{10}$ is hydrogen. In some embodiments is a compound of Formula II wherein $R_{10}$ is $C_1$-$C_6$alkyl. In some embodiments is a compound of Formula II wherein $R_{10}$ is $C_1$-$C_6$heteroalkyl. In some embodiments is a compound of Formula II wherein $R_{10}$ is —$C_1$-$C_6$alkyl-aryl. In some embodiments is a compound of Formula II wherein $R_{10}$ is aryl. In some embodiments is a compound of Formula II wherein $R_{10}$ is heteroaryl.

In another embodiment is a compound of Formula II wherein X is —S—, $R_1$ is C(=O)$OR_8$, $R_8$ is $C_1$-$C_6$alkyl, and $L_1$ is a bond. In another embodiment is a compound of Formula II wherein X is —S—, $R_1$ is C(=O)$OR_8$, $R_8$ is $C_1$-$C_6$alkyl, $L_1$ is a bond, $L_2$ is a $C_1$-$C_6$alkyl and $R_2$ is hydrogen. In another embodiment is a compound of Formula II wherein X is —S—, $R_1$ is C(=O)$OR_8$, $R_8$ is $C_1$-$C_6$alkyl, $L_1$ is a bond, $L_2$ is a $C_1$-$C_6$alkyl and $R_2$ is $C_3$-$C_8$cyclolkyl. In another embodiment is a compound of Formula II wherein X is —S—, $R_1$ is C(=O)$OR_8$, $R_8$ is $C_1$-$C_6$alkyl, $L_1$ is a bond, $L_2$ is $C_1$-$C_6$alkyl and $R_2$ is $C_1$-$C_6$heteroalkyl. In another embodiment is a compound of Formula II wherein X is —S—, $R_1$ is C(=O)$OR_8$, $R_8$ is $C_1$-$C_6$alkyl, $L_1$ is a bond, $L_2$ is $C_1$-$C_6$alkyl and $R_2$ is optionally substituted heterocycloalkyl. In a further embodiment of the aforementioned embodiments is a compound of Formula II wherein $R_4$ is phenyl substituted with one $R_{11}$. In a further embodiment of the aforementioned embodiments is a compound of Formula II wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula II wherein $R_4$ is phenyl substituted with one $R_{11}$, $R_{11}$ is —$SO_2R_{10}$ and $R_{10}$ is $CH_3$.

In another embodiment is a compound of Formula II wherein X is —S—, $R_1$ is C(=O)$OR_8$, $R_8$ is $C_1$-$C_6$alkyl, and $L_1$ is $C_1$-$C_6$alkyl. In another embodiment is a compound of Formula II wherein X is —S—, $R_1$ is C(=O)$OR_8$, $R_8$ is $C_1$-$C_6$alkyl, $L_1$ is $C_1$-$C_6$alkyl, $L_2$ is a $C_1$-$C_6$alkyl and $R_2$ is hydrogen. In another embodiment is a compound of Formula II wherein X is —S—, $R_1$ is C(=O)$OR_8$, $R_8$ is $C_1$-$C_6$alkyl, $L_1$ is $C_1$-$C_6$alkyl, $L_2$ is a $C_1$-$C_6$alkyl and $R_2$ is $C_3$-$C_8$cyclolkyl. In another embodiment is a compound of Formula II wherein X is —S—, $R_1$ is C(=O)$OR_8$, $R_8$ is $C_1$-$C_6$alkyl, $L_1$ is $C_1$-$C_6$alkyl, $L_2$ is $C_1$-$C_6$alkyl and $R_2$ is $C_1$-$C_6$heteroalkyl. In another embodiment is a compound of Formula II wherein X is —S—, $R_1$ is C(=O)$OR_8$, $R_8$ is $C_1$-$C_6$alkyl, $L_1$ is $C_1$-$C_6$alkyl, $L_2$ is $C_1$-$C_6$alkyl and $R_2$ is optionally substituted heterocycloalkyl. In a further embodiment of the aforementioned embodiments is a compound of Formula II wherein $R_4$ is phenyl substituted with one $R_{11}$. In a further embodiment of the aforementioned embodiments is a compound of Formula II wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula II wherein $R_4$ is phenyl substituted with one $R_{11}$, $R_{11}$ is —$SO_2R_{10}$ and $R_{10}$ is $CH_3$.

In another embodiment of the aforementioned embodiments is a compound of Formula II wherein $R_3$ is hydrogen, halogen, $C_1$-$C_6$alkyl, or $C_1$-$C_6$haloalkyl. In some embodiments of the aforementioned embodiments is a compound of Formula II wherein $R_3$ is hydrogen. In some embodiments of the aforementioned embodiments is a compound of Formula II wherein $R_3$ is halogen. In some embodiments of the aforementioned embodiments is a compound of Formula II wherein $R_3$ is $C_1$-$C_6$alkyl. In some embodiments of the aforementioned embodiments is a compound of Formula II wherein $R_3$ is $C_1$-$C_6$haloalkyl.

In some embodiments is a compound of Formula II wherein X is —CH=CH—. In a further embodiment is a compound of Formula II wherein $L_2$ is $C_1$-$C_6$alkyl. In yet a further embodiment is a compound of Formula II wherein $R_2$ is hydrogen, —$OR_9$, —$N(R_9)_2$, —C(=O)$R_9$, —C(=O)$N(R_9)_2$, —C(=N—OH)$R_9$, —C(=S)$N(R_9)_2$, $C_1$-$C_6$alkyl, $C_3$-$C_8$cycloalkyl, $C_1$-$C_6$haloalkyl, $C_1$-$C_6$heteroalkyl, or optionally substituted heterocycloalkyl. In some embodiments is a compound of Formula II wherein $R_2$ is —$OR_9$. In some embodiments is a compound of Formula II wherein $R_2$ is —$N(R_9)_2$. In some embodiments is a compound of Formula II wherein $R_2$ is —C(=O)$R_9$. In some embodiments is a compound of Formula II wherein $R_2$ is —C(=O)$N(R_9)_2$. In some embodiments is a compound of Formula II wherein $R_2$ is —C(=N—OH)$R_9$. In some embodiments is a compound of Formula II wherein $R_2$ is —C(=S)$N(R_9)_2$. In some embodiments is a compound of Formula II wherein $R_2$ is $C_1$-$C_6$alkyl. In some embodiments is a compound of Formula II wherein $R_2$ is $C_3$-$C_8$cycloalkyl. In some embodiments is a compound of Formula II wherein $R_2$ is $C_1$-$C_6$haloalkyl. In some embodiments is a compound of Formula II wherein $R_2$ is $C_1$-$C_6$heteroalkyl. In some embodiments is a compound of Formula II wherein $R_2$ is optionally substituted $C_2$-$C_7$heterocycloalkyl. In further embodiments is a compound of Formula II wherein $R_9$ is hydrogen, $C_1$-$C_6$alkyl, $C_1$-$C_6$heteroalkyl, —$C_1$-$C_6$alkyl-aryl, aryl, or heteroaryl. In some embodiments is a compound of Formula II wherein $R_9$ is hydrogen. In some embodiments is a compound of Formula II wherein $R_8$ is $C_1$-$C_6$alkyl. In some embodiments is a compound of Formula II wherein $R_9$ is methyl. In some embodiments, $R_9$ is ethyl. In some embodiments is a compound of Formula II wherein $R_9$ is $C_1$-$C_6$heteroalkyl. In some embodiments is a compound of Formula II wherein $R_9$ is —$C_1$-$C_6$alkyl-aryl. In some embodiments is a compound of Formula II wherein $R_9$ is aryl. In some embodiments is a compound of Formula II wherein $R_9$ is heteroaryl.

In some embodiments is a compound of Formula II wherein X is —CH=CH—, $R_1$ is —C(=O)$OR_8$, and $R_8$ is hydrogen, $C_1$-$C_6$alkyl, $C_1$-$C_6$heteroalkyl, —$C_1$-$C_6$alkyl-aryl, aryl, or heteroaryl. In some embodiments is a compound of Formula II wherein X is —CH=CH—, $R_1$ is —C(=O)$OR_8$, and $R_8$ is hydrogen. In some embodiments is a compound of Formula II wherein X is —CH=CH—, $R_1$ is —C(=O)$OR_8$, and $R_8$ is $C_1$-$C_6$alkyl. In some embodiments is a compound of Formula II wherein X is —CH=CH—, $R_1$ is —C(=O)$OR_8$, and $R_8$ is methyl. In some embodiments is a compound of Formula II wherein X is —CH=CH—, $R_1$ is —C(=O)$OR_8$, and $R_8$ is ethyl. In some embodiments is a compound of Formula II wherein X is —CH=CH—, $R_1$ is —C(=O)$OR_8$, and $R_8$ is $C_1$-$C_6$heteroalkyl. In some embodiments is a compound of Formula II wherein X is —CH=CH—, $R_1$ is —C(=O)$OR_8$, and $R_8$ is —$C_1$-$C_6$alkyl-aryl. In some embodiments is a compound of Formula II wherein X is —CH=CH—, $R_1$ is —C(=O)$OR_8$, and $R_8$ is aryl. In some embodiments is a compound of Formula II wherein X is —CH=CH—, $R_1$ is —C(=O)$OR_8$, and $R_8$ is heteroaryl.

In some embodiments is a compound of Formula II wherein X is —CH=CH—, $L_1$ is a bond, $C_1$-$C_6$alkyl, or $C_1$-$C_6$heteroalkyl wherein $C_1$-$C_6$alkyl and $C_1$-$C_6$heteroalkyl are optionally substituted with at least one $R_7$, and $L_2$ is $C_1$-$C_6$alkyl, or $C_1$-$C_6$heteroalkyl. In a further embodiment is a compound of Formula II wherein X is —CH=CH—, $L_1$ is a bond, and $L_2$ is a $C_1$-$C_6$alkyl. In a further embodiment is a compound of Formula II wherein X is —CH=CH—, $L_1$ is $C_1$-$C_6$alkyl optionally substituted with at least one $R_7$, and $L_2$ is a $C_1$-$C_6$alkyl. In further embodiments is a compound of Formula II wherein X is —CH=CH—, $L_1$ is $C_1$-$C_6$heteroalkyl optionally substituted with at least one $R_7$, and $L_2$ is $C_1$-$C_6$alkyl. In further embodiments is a compound of Formula II wherein X is —CH=CH—, $L_1$ is a bond, and $L_2$ is $C_1$-$C_6$heteroalkyl. In further embodiments is a compound of Formula II wherein X is —CH=CH—, $L_1$ is $C_1$-$C_6$alkyl optionally substituted with at least one $R_7$, and $L_2$ is $C_1$-$C_6$heteroalkyl. In further embodiments is a compound of Formula II wherein X is —CH=CH—, $L_1$ is $C_1$-$C_6$heteroalkyl optionally substituted with at least one $R_7$, and $L_2$ is $C_1$-$C_6$heteroalkyl. In a further embodiment of the aforementioned embodiments is a compound of Formula II wherein each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments of the aforementioned embodiments is a compound of Formula II wherein each $R_7$ is $C_1$-$C_6$alkyl. In some embodiments of the aforementioned embodiments is a compound of Formula II wherein each $R_7$ is —$C_1$-$C_6$alkyl-aryl. In some embodiments of the aforementioned embodiments is a compound of Formula II wherein each $R_7$ is optionally substituted aryl.

In some embodiments is a compound of Formula II wherein X is —CH=CH— and $R_4$ is aryl or heteroaryl; wherein aryl and heteroaryl are substituted with at least one $R_{11}$. In some embodiments is a compound of Formula II wherein $R_4$ is aryl substituted with one $R_{11}$. In some embodiments is a compound of Formula II wherein $R_4$ is aryl substituted with two $R_{11}$. In some embodiments is a compound of Formula II wherein $R_4$ is aryl substituted with three $R_{11}$. In further embodiments is a compound of Formula II wherein $R_4$ is phenyl substituted with one $R_{11}$. In further embodiments is a compound of Formula II wherein $R_4$ is phenyl substituted with two $R_{11}$. In further embodiments is a compound of Formula II wherein $R_4$ is phenyl substituted with three $R_{11}$. In some embodiments is a compound of Formula II wherein $R_4$ is heteroaryl substituted with one $R_{11}$. In some embodiments is a compound of Formula II wherein $R_4$ is heteroaryl substituted with two $R_{11}$. In some embodiments is a compound of Formula II wherein $R_4$ is heteroaryl substituted with three $R_{11}$.

In some embodiments is a compound of Formula II wherein X is —CH=CH—, $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, —$NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula II wherein X is —CH=CH—, $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, —$NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments is a compound of Formula II wherein $R_{11}$ is —$OR_{10}$. In further embodiments is a compound of Formula II wherein $R_{11}$ is —$N(R_{10})_2$. In further embodiments is a compound of Formula II wherein $R_{11}$ is —CN. In further embodiments is a compound of Formula II wherein $R_{11}$ is —C(=O)$R_{10}$. In further embodiments is a compound of Formula II wherein $R_{11}$ is —C(=O)$OR_{10}$. In further embodiments is a compound of Formula II wherein $R_{11}$ is —C(=O)$N(R_{10})_2$. In further embodiments is a compound of Formula II wherein $R_{11}$ is —$NR_{10}$C(=O)$R_{10}$. In further embodiments is a compound of Formula II wherein $R_{11}$ is —$NR_{10}SO_2R_{10}$. In further embodiments is a compound of Formula II wherein $R_{11}$ is —$SOR_{10}$. In further embodiments is a compound of Formula II wherein $R_{11}$ is —$SO_2R_{10}$. In further embodiments is a compound of Formula II wherein $R_{11}$ is —$SO_2N(R_{10})_2$. In further embodiments is a compound of Formula II wherein $R_{11}$ is —C(=O)$OCH_2SCH_3$. In further embodiments is a compound of Formula II wherein $R_{11}$ is $C_1$-$C_6$alkyl. In further embodiments is a compound of Formula II wherein $R_{11}$ is optionally substituted $C_3$-$C_8$cycloalkyl. In further embodiments is a compound of Formula II wherein $R_{11}$ is $C_1$-$C_6$haloalkyl. In further embodiments is a compound of Formula II wherein $R_{11}$ is $C_1$-$C_6$heteroalkyl. In further embodiments is a compound of Formula II wherein $R_{11}$ is —$C_1$-$C_6$alkyl-aryl. In further embodiments is a compound of Formula II wherein $R_{11}$ is optionally substituted aryl. In further embodiments is a compound of Formula II wherein $R_{11}$ is optionally substituted heteroaryl. In yet further embodiments is a compound of Formula II wherein each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments is a compound of Formula II wherein $R_{10}$ is hydrogen. In some embodiments is a compound of Formula II wherein $R_{10}$ is $C_1$-$C_6$alkyl. In some embodiments is a compound of Formula II wherein $R_{10}$ is $C_1$-$C_6$heteroalkyl. In some embodiments is a compound of Formula II wherein $R_{10}$ is —$C_1$-$C_6$alkyl-aryl. In some embodiments is a compound of Formula II wherein $R_{10}$ is aryl. In some embodiments is a compound of Formula II wherein $R_{10}$ is heteroaryl.

In another embodiment is a compound of Formula II wherein X is —CH=CH—, $R_1$ is C(=O)$OR_8$, $R_8$ is $C_1$-$C_6$alkyl, and $L_1$ is a bond. In another embodiment is a compound of Formula II wherein X is —CH=CH—, $R_1$ is C(=O)$OR_8$, $R_8$ is $C_1$-$C_6$alkyl, $L_1$ is a bond, $L_2$ is a $C_1$-$C_6$alkyl and $R_2$ is hydrogen. In another embodiment is a compound of Formula II wherein X is —CH=CH—, $R_1$ is C(=O)$OR_8$, $R_8$ is $C_1$-$C_6$alkyl, $L_1$ is a bond, $L_2$ is a $C_1$-$C_6$alkyl and $R_2$ is $C_3$-$C_8$cyclolkyl. In another embodiment is a compound of Formula II wherein X is —CH=CH—, $R_1$ is C(=O)$OR_8$, $R_8$ is $C_1$-$C_6$alkyl, $L_1$ is a bond, $L_2$ is $C_1$-$C_6$alkyl and $R_2$ is $C_1$-$C_6$heteroalkyl. In another embodiment is a compound of Formula II wherein X is —CH=CH—, $R_1$ is C(=O)$OR_8$, $R_8$ is $C_1$-$C_6$alkyl, $L_1$ is a bond, $L_2$ is $C_1$-$C_6$alkyl and $R_2$ is optionally substituted heterocycloalkyl. In a further embodiment of the aforementioned embodiments is a compound of Formula II wherein $R_4$ is phenyl substituted with one $R_{11}$. In a further embodiment of the aforementioned embodiments is a compound of Formula II wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula II wherein $R_4$ is phenyl substituted with one $R_{11}$, $R_{11}$ is —$SO_2R_{10}$ and $R_{10}$ is $CH_3$.

In another embodiment is a compound of Formula II wherein X is —CH=CH—, $R_1$ is C(=O)$OR_8$, $R_8$ is $C_1$-$C_6$alkyl, and $L_1$ is $C_1$-$C_6$alkyl. In another embodiment is a compound of Formula II wherein X is —CH=CH—, $R_1$ is C(=O)$OR_8$, $R_8$ is $C_1$-$C_6$alkyl, $L_1$ is $C_1$-$C_6$alkyl, $L_2$ is a $C_1$-$C_6$alkyl and $R_2$ is hydrogen. In another embodiment is a compound of Formula II wherein X is —CH=CH—, $R_1$ is C(=O)$OR_8$, $R_8$ is $C_1$-$C_6$alkyl, $L_1$ is $C_1$-$C_6$alkyl, $L_2$ is a $C_1$-$C_6$alkyl and $R_2$ is $C_3$-$C_8$cyclolkyl. In another embodiment is a compound of Formula II wherein X is —CH=CH—, $R_1$ is C(=O)$OR_8$, $R_8$ is $C_1$-$C_6$alkyl, $L_1$ is $C_1$-$C_6$alkyl, $L_2$ is $C_1$-$C_6$alkyl and $R_2$ is $C_1$-$C_6$heteroalkyl. In another embodiment is a compound of Formula II wherein X is —CH=CH—, $R_1$ is C(=O)$OR_8$, $R_8$ is $C_1$-$C_6$alkyl, $L_1$ is $C_1$-$C_6$alkyl, $L_2$ is $C_1$-$C_6$alkyl and $R_2$ is optionally substituted heterocycloalkyl. In a further embodiment of the aforementioned embodiments is a compound of Formula II wherein $R_4$ is phenyl substituted with one $R_{11}$. In a further embodiment of the aforementioned embodiments is a compound of Formula II wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula II wherein $R_4$ is phenyl substituted with one $R_{11}$, $R_{11}$ is —$SO_2R_{10}$ and $R_{10}$ is $CH_3$.

In another embodiment of the aforementioned embodiments is a compound of Formula II wherein $R_3$ is hydrogen, halogen, $C_1$-$C_6$alkyl, or $C_1$-$C_6$haloalkyl. In some embodiments of the aforementioned embodiments is a compound of Formula II wherein $R_3$ is hydrogen. In some embodiments of the aforementioned embodiments is a compound of Formula II wherein $R_3$ is halogen. In some embodiments of the aforementioned embodiments is a compound of Formula II wherein $R_3$ is $C_1$-$C_6$alkyl. In some embodiments of the aforementioned embodiments is a compound of Formula II wherein $R_3$ is $C_1$-$C_6$haloalkyl.

In some embodiments is a compound of Formula II, wherein X is —CH=CH—; and $L_1$ is a bond. In some embodiments is a compound of Formula II, wherein X is —CH=CH—; $R_1$ is a —C(=O)$OR_8$; and $R_8$ is hydrogen or $C_1$-$C_6$alkyl. In some embodiments is a compound of Formula II, wherein X is —CH=CH—; and $R_8$ is hydrogen, methyl, or ethyl. In some embodiments is a compound of Formula II, wherein X is —CH=CH—; and $L_2$ is $C_1$-$C_6$alkyl. In some embodiments is a compound of Formula II, wherein X is —CH=CH—; and -$L_2$-$R_2$ is isobutyl. In some embodiments is a compound of Formula II, wherein X is —CH=CH—; and $R_2$ is hydrogen.

In some embodiments is a compound of Formula II, wherein X is —CH=CH—; and $R_4$ is phenyl substituted with at least one $R_{11}$. In some embodiments is a compound of Formula II, wherein X is —CH=CH—; and at least one $R_{11}$ is —$NR_{10}SO_2R_{10}$, —$SOR_{10}$, —$SO_2R_{10}$, or —$SO_2N(R_{10})_2$. In some embodiments is a compound of Formula II, wherein X is —CH=CH—; and at least one $R_{11}$ is —$SO_2R_{10}$. In some embodiments is a compound of Formula II, wherein X is —CH=CH—; and each $R_{10}$ is independently $C_1$-$C_6$ alkyl. In some embodiments is a compound of Formula II, wherein X is —CH=CH—; and each $R_{10}$ is methyl. In some embodiments is a compound of Formula II, wherein X is —CH=CH—; and $R_4$ is phenyl substituted with one $R_{11}$, wherein $R_{11}$ is —$SO_2R_{10}$ and $R_{10}$ is $C_1$-$C_6$alkyl; or $R_4$ is phenyl substituted with two $R_{11}$, and one $R_{11}$ is —$SO_2R_{10}$ and one $R_{11}$ is optionally substituted $C_1$-$C_6$alkyl. In some embodiments is a compound of Formula II, wherein X is —CH=CH—; and $R_4$ is phenyl substituted with one $R_{11}$, wherein $R_{11}$ is —$SO_2R_{10}$ and $R_{10}$ is $C_1$-$C_6$alkyl. In some embodiments is a compound of Formula II, wherein X is —CH=CH—; and $R_4$ is phenyl substituted with one $R_{11}$, wherein $R_{11}$ is —$SO_2R_{10}$ and $R_{10}$ is methyl. In some embodiments is a compound of Formula II, wherein X is —CH=CH—; and $R_4$ is phenyl substituted with two $R_{11}$, wherein one $R_{11}$ is —$SO_2CH_3$ and one $R_{11}$ is —$CH_2OH$. In some embodiments is a compound of Formula II, wherein X is —CH=CH—; and "optionally substituted" means optionally substituted by 1, 2, 3, or 4 substituents independently selected from halo, cyano, $C_1$-$C_4$ alkyl, $C_2$-$C_4$ alkenyl, hydoxy, $C_1$-$C_4$ alkoxy, $C_1$-$C_4$ haloalkyl, $C_1$-$C_4$ haloalkoxy, amino, $C_1$-$C_4$ alkylamino, and di($C_1$-$C_4$ alkyl) amino.

In some embodiments is a compound of Formula II, wherein X is —CH=CH—; and n is 0. In some embodiments is a compound of Formula II, wherein X is —CH=CH—; and $R_3$ is hydrogen.

In some embodiments, the compound is a compound of Formula (IIA):

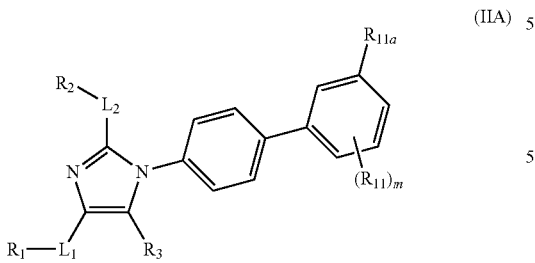

wherein:
m is 0 or 1; and
$R_{11a}$ is —$NR_{10}SO_2R_{10}$, —$SOR_{10}$, —$SO_2R_{10}$, or —$SO_2N(R_{10})_2$;
or a pharmaceutically acceptable salt thereof.

In some embodiments, the compound is a compound of Formula (IIB):

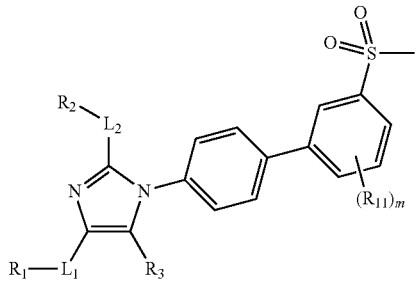

wherein m is 0 or 1;
or a pharmaceutically acceptable salt thereof.

In some embodiments is a compound of Formula II, wherein:
X is —CH=CH—;
$R_1$ is a —C(=O)$OR_8$; and $R_8$ is $C_1$-$C_6$alkyl;
$L_2$ is $C_1$-$C_6$alkyl;
$R_2$ is hydrogen;
$R_4$ is phenyl substituted with at least one $R_{11}$;
each $R_{11}$ is independently $C_1$-$C_6$ alkyl, —$NR_{10}SO_2R_{10}$, —$SOR_{10}$, —$SO_2R_{10}$, or —$SO_2N(R_{10})_2$; wherein said $C_1$-$C_6$ alkyl is optionally substituted by 1 hydroxy; provided that at least one $R_{11}$ is —$NR_{10}SO_2R_{10}$, —$SOR_{10}$, —$SO_2R_{10}$, or —$SO_2N(R_{10})_2$;
each $R_{10}$ is independently $C_1$-$C_6$ alkyl;
n is 0; and
$R_3$ is hydrogen.

In some embodiments is a compound of Formula II, wherein:
X is —CH=CH—;
$R_1$ is a —C(=O)$OR_8$; and $R_8$ is $C_1$-$C_6$alkyl;
$L_2$ is $C_1$-$C_6$alkyl;
$R_2$ is hydrogen;
$R_4$ is phenyl substituted with at least one $R_{11}$;
each $R_{11}$ is independently $C_1$-$C_6$ alkyl or —$SO_2R_{10}$;
wherein said $C_1$-$C_6$ alkyl is optionally substituted by 1 hydroxy;
provided that at least one $R_{11}$ is —$SO_2R_{10}$;
each $R_{10}$ is independently $C_1$-$C_6$ alkyl;
n is 0; and
$R_3$ is hydrogen.

In some embodiments, the compound is selected from:

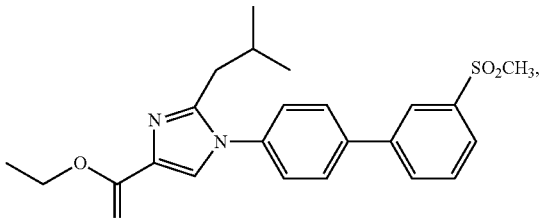

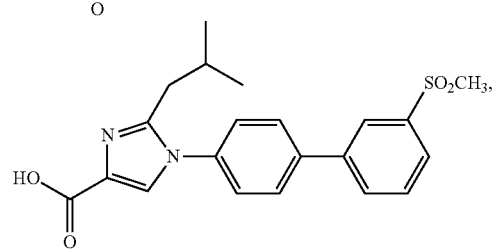

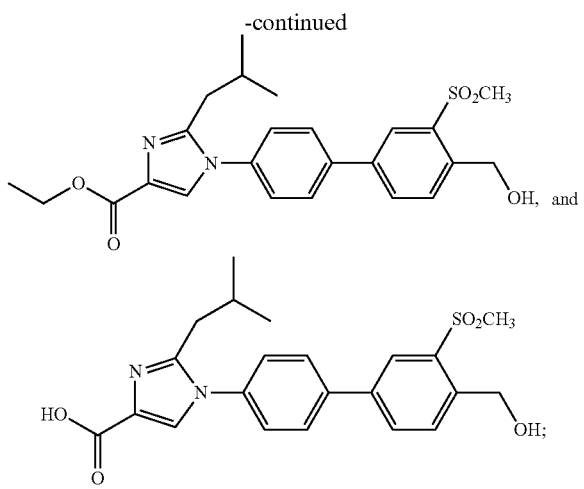

or a pharmaceutically acceptable salt thereof.

In another aspect is a compound of Formula (III):

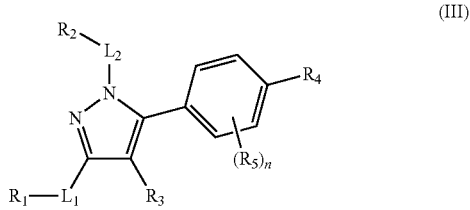

wherein:
$L_1$ is a bond, $C_1$-$C_6$alkyl, or $C_1$-$C_6$heteroalkyl; wherein $C_1$-$C_6$alkyl and $C_1$-$C_6$heteroalkyl are optionally substituted with at least one $R_7$;

$L_2$ is a $C_1$-$C_6$alkyl, or $C_1$-$C_6$heteroalkyl;

$R_1$ is —C(=O)OR$_8$;

$R_2$ is hydrogen, —OR$_9$, —N(R$_9$)$_2$, —C(=O)R$_9$, —C(=O)N(R$_9$)$_2$, —C(=N—OH)R$_9$, —C(=S)N(R$_9$)$_2$, $C_1$-$C_6$alkyl, $C_3$-$C_8$cycloalkyl, $C_1$-$C_6$haloalkyl, $C_1$-$C_6$heteroalkyl, or optionally substituted heterocycloalkyl;

$R_3$ is hydrogen, halogen, $C_1$-$C_6$alkyl, or $C_1$-$C_6$haloalkyl;

$R_4$ is aryl or heteroaryl; wherein aryl and heteroaryl are substituted with at least one $R_{11}$;

each $R_5$ is independently halogen, $C_1$-$C_6$alkyl, or $C_1$-$C_6$haloalkyl;

each $R_7$ is independently $C_1$-$C_6$alkyl, $C_3$-$C_8$cycloalkyl, $C_1$-$C_6$haloalkyl, $C_1$-$C_6$heteroalkyl, —C$_1$-$C_6$alkyl-aryl, optionally substituted aryl, or optionally substituted heteroaryl;

each $R_8$, each $R_9$, and each $R_{10}$ are each independently hydrogen, $C_1$-$C_6$alkyl, $C_1$-$C_6$heteroalkyl, —C$_1$-$C_6$alkyl-aryl, aryl, or heteroaryl;

each $R_{11}$ is independently halogen, nitro, —OR$_{10}$, —N(R$_{10}$)$_2$, —CN, —C(=O)R$_{10}$, —C(=O)OR$_{10}$, —C(=O)N(R$_{10}$)$_2$, —NR$_{10}$C(=O)R$_{10}$, —NR$_{10}$SO$_2$R$_{10}$, —SOR$_{10}$, —SO$_2$R$_{10}$, —SO$_2$N(R$_{10}$)$_2$, —C(=O)OCH$_2$SCH$_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —C$_1$-$C_6$alkyl-aryl, optionally substituted aryl, or optionally substituted heteroaryl; and n is 0-4; or a pharmaceutically acceptable salt, pharmaceutically acceptable solvate, or pharmaceutically acceptable prodrug thereof.

In some embodiments is a compound of Formula III wherein $L_2$ is $C_1$-$C_6$alkyl. In yet a further embodiment is a compound of Formula III wherein $R_2$ is hydrogen, —OR$_9$, —N(R$_9$)$_2$, —C(=O)R$_9$, —C(=O)N(R$_9$)$_2$, —C(=N—OH) R$_9$, —C(=S)N(R$_9$)$_2$, $C_1$-$C_6$alkyl, $C_3$-$C_8$cycloalkyl, $C_1$-$C_6$haloalkyl, $C_1$-$C_6$heteroalkyl, or optionally substituted heterocycloalkyl. In some embodiments is a compound of Formula III wherein $R_2$ is —OR$_9$. In some embodiments is a compound of Formula III wherein $R_2$ is —N(R$_9$)$_2$. In some embodiments is a compound of Formula III wherein $R_2$ is —C(=O)R$_9$. In some embodiments is a compound of Formula III wherein $R_2$ is —C(=O)N(R$_9$)$_2$. In some embodiments is a compound of Formula III wherein $R_2$ is —C(=N—OH)R$_9$. In some embodiments is a compound of Formula III wherein $R_2$ is —C(=S)N(R$_9$)$_2$. In some embodiments is a compound of Formula III wherein $R_2$ is $C_1$-$C_6$alkyl. In some embodiments is a compound of Formula III wherein $R_2$ is $C_3$-$C_8$cycloalkyl. In some embodiments is a compound of Formula III wherein $R_2$ is $C_1$-$C_6$haloalkyl. In some embodiments is a compound of Formula III wherein $R_2$ is $C_1$-$C_6$heteroalkyl. In some embodiments is a compound of Formula III wherein $R_2$ is optionally substituted $C_2$-$C_7$heterocycloalkyl. In further embodiments is a compound of Formula III wherein $R_9$ is hydrogen, $C_1$-$C_6$alkyl, $C_1$-$C_6$heteroalkyl, —C$_1$-$C_6$alkyl-aryl, aryl, or heteroaryl. In some embodiments is a compound of Formula III wherein $R_9$ is hydrogen. In some embodiments is a compound of Formula III wherein $R_9$ is $C_1$-$C_6$alkyl. In some embodiments is a compound of Formula III wherein $R_9$ is methyl. In some embodiments, $R_9$ is ethyl. In some embodiments is a compound of Formula III wherein $R_9$ is $C_1$-$C_6$heteroalkyl. In some embodiments is a compound of Formula III wherein $R_9$ is —C$_1$-$C_6$alkyl-aryl. In some embodiments is a compound of Formula III wherein $R_9$ is aryl. In some embodiments is a compound of Formula III wherein $R_9$ is heteroaryl.

In some embodiments is a compound of Formula III wherein $R_1$ is —C(=O)OR$_8$, and $R_8$ is hydrogen, $C_1$-$C_6$alkyl, $C_1$-$C_6$heteroalkyl, —C$_1$-$C_6$alkyl-aryl, aryl, or heteroaryl. In some embodiments is a compound of Formula III wherein $R_1$ is —C(=O)OR$_8$, and $R_8$ is hydrogen. In some embodiments is a compound of Formula III wherein $R_1$ is —C(=O)OR$_8$, and $R_8$ is $C_1$-$C_6$alkyl. In some embodiments is a compound of Formula III wherein $R_1$ is —C(=O) OR$_8$, and $R_8$ is methyl. In some embodiments is a compound of Formula III wherein $R_1$ is —C(=O)OR$_8$, and $R_8$ is ethyl. In some embodiments is a compound of Formula III wherein $R_1$ is —C(=O)OR$_8$, and $R_8$ is $C_1$-$C_6$heteroalkyl. In some embodiments is a compound of Formula III wherein $R_1$ is —C(=O)OR$_8$, and $R_8$ is —C$_1$-$C_6$alkyl-aryl. In some embodiments is a compound of Formula III wherein $R_1$ is —C(=O)OR$_8$, and $R_8$ is aryl. In some embodiments is a compound of Formula III wherein $R_1$ is —C(=O)OR$_8$, and $R_8$ is heteroaryl.

In some embodiments is a compound of Formula III wherein $L_1$ is a bond, $C_1$-$C_6$alkyl, or $C_1$-$C_6$heteroalkyl wherein $C_1$-$C_6$alkyl and $C_1$-$C_6$heteroalkyl are optionally substituted with at least one $R_7$, and $L_2$ is $C_1$-$C_6$alkyl, or $C_1$-$C_6$heteroalkyl. In a further embodiment is a compound of Formula III wherein $L_1$ is a bond, and $L_2$ is a $C_1$-$C_6$alkyl. In a further embodiment is a compound of Formula III wherein $L_1$ is $C_1$-$C_6$alkyl optionally substituted with at least one $R_7$, and $L_2$ is a $C_1$-$C_6$alkyl. In further embodiments is a compound of Formula III wherein $L_1$ is $C_1$-$C_6$heteroalkyl optionally substituted with at least one $R_7$, and $L_2$ is $C_1$-$C_6$alkyl. In further embodiments is a compound of Formula III wherein $L_1$ is a bond, and $L_2$ is $C_1$-$C_6$heteroalkyl. In further embodiments is a compound of Formula III wherein $L_1$ is $C_1$-$C_6$alkyl optionally substituted with at least one $R_7$, and $L_2$ is $C_1$-$C_6$heteroalkyl. In further embodiments is a compound of Formula III wherein $L_1$ is $C_1$-$C_6$heteroalkyl optionally substituted with at least one $R_7$, and $L_2$ is $C_1$-$C_6$heteroalkyl. In a further embodiment of the aforementioned embodiments is a compound of Formula III wherein each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments of the aforementioned embodiments is a compound of Formula III wherein each $R_7$ is $C_1$-$C_6$alkyl. In some embodiments of the aforementioned embodiments is a compound of Formula III wherein each $R_7$ is —$C_1$-$C_6$alkyl-aryl. In some embodiments of the aforementioned embodiments is a compound of Formula III wherein each $R_7$ is optionally substituted aryl.

In some embodiments is a compound of Formula III wherein $R_4$ is aryl or heteroaryl; wherein aryl and heteroaryl are substituted with at least one $R_{11}$. In some embodiments is a compound of Formula III wherein $R_4$ is aryl substituted with one $R_{11}$. In some embodiments is a compound of Formula III wherein $R_4$ is aryl substituted with two $R_{11}$. In some embodiments is a compound of Formula III wherein $R_4$ is aryl substituted with three $R_{11}$. In further embodiments is a compound of Formula III wherein $R_4$ is phenyl substituted with one $R_{11}$. In further embodiments is a compound of Formula III wherein $R_4$ is phenyl substituted with two $R_{11}$. In further embodiments is a compound of Formula III wherein $R_4$ is phenyl substituted with three $R_{11}$. In some embodiments is a compound of Formula III wherein $R_4$ is heteroaryl substituted with one $R_{11}$. In some embodiments is a compound of Formula III wherein $R_4$ is heteroaryl substituted with two $R_{11}$. In some embodiments is a compound of Formula III wherein $R_4$ is heteroaryl substituted with three $R_{11}$.

In some embodiments is a compound of Formula III wherein $R_4$ is phenyl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, —$NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In some embodiments is a compound of Formula III wherein $R_4$ is heteroaryl substituted with at least one $R_{11}$, and each $R_{11}$ is independently —$OR_{10}$, —$N(R_{10})_2$, —CN, —C(=O)$R_{10}$, —C(=O)$OR_{10}$, —C(=O)$N(R_{10})_2$, —$NR_{10}$C(=O)$R_{10}$, $NR_{10}SO_2R_{10}$, —$SOR_{10}$, —$SO_2R_{10}$, —$SO_2N(R_{10})_2$, —C(=O)$OCH_2SCH_3$, $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl. In further embodiments is a compound of Formula III wherein $R_{11}$ is —$OR_{10}$. In further embodiments is a compound of Formula III wherein $R_{11}$ is —$N(R_{10})_2$. In further embodiments is a compound of Formula III wherein $R_{11}$ is —CN. In further embodiments is a compound of Formula III wherein $R_{11}$ is —C(=O)$R_{10}$. In further embodiments is a compound of Formula III wherein $R_{11}$ is —C(=O)$OR_{10}$. In further embodiments is a compound of Formula III wherein $R_{11}$ is —C(=O)$N(R_{10})_2$. In further embodiments is a compound of Formula III wherein $R_{11}$ is —$NR_{10}$C(=O)$R_{10}$. In further embodiments is a compound of Formula III wherein $R_{11}$ is $NR_{10}SO_2R_{10}$. In further embodiments is a compound of Formula III wherein $R_{11}$ is —$SOR_{10}$. In further embodiments is a compound of Formula III wherein $R_{11}$ is —$SO_2R_{10}$. In further embodiments is a compound of Formula III wherein $R_{11}$ is —$SO_2N(R_{10})_2$. In further embodiments is a compound of Formula III wherein $R_{11}$ is —C(=O)$OCH_2SCH_3$. In further embodiments is a compound of Formula III wherein $R_{11}$ is $C_1$-$C_6$alkyl. In further embodiments is a compound of Formula III wherein $R_{11}$ is optionally substituted $C_3$-$C_8$cycloalkyl. In further embodiments is a compound of Formula III wherein $R_{11}$ is $C_1$-$C_6$haloalkyl. In further embodiments is a compound of Formula III wherein $R_{11}$ is $C_1$-$C_6$heteroalkyl. In further embodiments is a compound of Formula III wherein $R_{11}$ is —$C_1$-$C_6$alkyl-aryl. In further embodiments is a compound of Formula III wherein $R_{11}$ is optionally substituted aryl. In further embodiments is a compound of Formula III wherein $R_{11}$ is optionally substituted heteroaryl. In yet further embodiments is a compound of Formula III wherein each $R_{10}$ is independently hydrogen, $C_1$-$C_6$alkyl, $C_1$-$C_6$heteroalkyl, —$C_1$-$C_6$alkyl-aryl, aryl, or heteroaryl. In some embodiments is a compound of Formula III wherein $R_{10}$ is hydrogen. In some embodiments is a compound of Formula III wherein $R_{10}$ is $C_1$-$C_6$alkyl. In some embodiments is a compound of Formula III wherein $R_{10}$ is $C_1$-$C_6$heteroalkyl. In some embodiments is a compound of Formula III wherein $R_{10}$ is —$C_1$-$C_6$alkyl-aryl. In some embodiments is a compound of Formula III wherein $R_{10}$ is aryl. In some embodiments is a compound of Formula III wherein $R_{10}$ is heteroaryl.

In another embodiment is a compound of Formula III wherein $R_1$ is C(=O)$OR_8$, $R_8$ is $C_1$-$C_6$alkyl, and $L_1$ is a bond. In another embodiment is a compound of Formula III wherein $R_1$ is C(=O)$OR_8$, $R_8$ is $C_1$-$C_6$alkyl, $L_1$ is a bond, $L_2$ is a $C_1$-$C_6$alkyl and $R_2$ is hydrogen. In another embodiment is a compound of Formula III wherein $R_1$ is C(=O)$OR_8$, $R_8$ is $C_1$-$C_6$alkyl, $L_1$ is a bond, $L_2$ is a $C_1$-$C_6$alkyl and $R_2$ is $C_3$-$C_8$cyclolkyl. In another embodiment is a compound of Formula III wherein $R_1$ is C(=O)$OR_8$, $R_8$ is $C_1$-$C_6$alkyl, $L_1$ is a bond, $L_2$ is $C_1$-$C_6$alkyl and $R_2$ is $C_1$-$C_6$heteroalkyl. In another embodiment is a compound of Formula III wherein $R_1$ is C(=O)$OR_8$, $R_8$ is $C_1$-$C_6$alkyl, $L_1$ is a bond, $L_2$ is $C_1$-$C_6$alkyl and $R_2$ is optionally substituted heterocycloalkyl. In a further embodiment of the aforementioned embodiments is a compound of Formula III wherein $R_4$ is phenyl substituted with one $R_{11}$. In a further embodiment of the aforementioned embodiments is a compound of Formula III wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula III wherein $R_4$ is phenyl substituted with one $R_{11}$, $R_{11}$ is —$SO_2R_{10}$ and $R_{10}$ is $CH_3$.

In another embodiment is a compound of Formula III wherein $R_1$ is C(=O)$OR_8$, $R_8$ is $C_1$-$C_6$alkyl, and $L_1$ is $C_1$-$C_6$alkyl. In another embodiment is a compound of Formula III wherein $R_1$ is C(=O)$OR_8$, $R_8$ is $C_1$-$C_6$alkyl, $L_1$ is $C_1$-$C_6$alkyl, $L_2$ is a $C_1$-$C_6$alkyl and $R_2$ is hydrogen. In another embodiment is a compound of Formula III wherein $R_1$ is C(=O)$OR_8$, $R_8$ is $C_1$-$C_6$alkyl, $L_1$ is $C_1$-$C_6$alkyl, $L_2$ is a $C_1$-$C_6$alkyl and $R_2$ is $C_3$-$C_8$cyclolkyl. In another embodiment is a compound of Formula III wherein $R_1$ is C(=O)$OR_8$, $R_8$ is $C_1$-$C_6$alkyl, $L_1$ is $C_1$-$C_6$alkyl, $L_2$ is $C_1$-$C_6$alkyl and $R_2$ is $C_1$-$C_6$heteroalkyl. In another embodiment is a compound of Formula III wherein $R_1$ is C(=O)$OR_8$, $R_8$ is $C_1$-$C_6$alkyl, $L_1$ is $C_1$-$C_6$alkyl, $L_2$ is $C_1$-$C_6$alkyl and $R_2$ is optionally substituted heterocycloalkyl. In a further embodiment of the aforementioned embodiments is a compound of Formula III wherein $R_4$ is phenyl substituted with one $R_{11}$. In a further embodiment of the aforementioned embodiments is a compound of Formula III wherein $R_4$ is phenyl substituted with one $R_{11}$, $R_{11}$ is —$SO_2R_{10}$ and $R_{10}$ is $C_1$-$C_6$alkyl. In yet a further embodiment of the aforementioned embodiments is a compound of Formula III wherein $R_4$ is phenyl substituted with one $R_{11}$, $R_{11}$ is —$SO_2R_{10}$ and $R_{10}$ is $CH_3$.

In another embodiment of the aforementioned embodiments is a compound of Formula III wherein $R_3$ is hydrogen, halogen, $C_1$-$C_6$alkyl, or $C_1$-$C_6$haloalkyl. In some embodiments of the aforementioned embodiments is a compound of Formula III wherein $R_3$ is hydrogen. In some embodiments of the aforementioned embodiments is a compound of Formula III wherein $R_3$ is halogen. In some embodiments of the aforementioned embodiments is a compound of Formula III wherein $R_3$ is $C_1$-$C_6$alkyl. In some embodiments of the aforementioned embodiments is a compound of Formula III wherein $R_3$ is $C_1$-$C_6$haloalkyl.

In some embodiments is a compound of Formula III, wherein $L_2$ is a $C_1$-$C_6$alkyl and $R_2$ is hydrogen. In some embodiments is a compound of Formula III, wherein -$L_2$-$R_2$ is isobutyl. In some embodiments is a compound of Formula III, wherein $L_1$ is a bond. In some embodiments is a compound of Formula III, wherein $R_1$ is —C(=O)O$R_8$, and $R_8$ is hydrogen. In some embodiments is a compound of Formula III, wherein $R_1$ is —C(=O)O$R_8$, and $R_8$ is $C_1$-$C_6$alkyl. In some embodiments is a compound of Formula III, wherein $R_1$ is —C(=O)O$R_8$, and $R_8$ is ethyl. In some embodiments is a compound of Formula III, wherein $R_1$ is C(=O)O$R_8$, $R_8$ is $C_1$-$C_6$alkyl, $L_1$ is a bond, $L_2$ is a $C_1$-$C_6$alkyl, and $R_2$ is hydrogen. In some embodiments is a compound of Formula III, n is 0.

In some embodiments is a compound of Formula III, wherein $R_4$ is phenyl substituted with at least one $R_{11}$. In some embodiments is a compound of Formula III, wherein at least one $R_{11}$ is —$NR_{10}SO_2R_{10}$, —$SOR_{10}$, —$SO_2R_{10}$, or —$SO_2N(R_{10})_2$. In some embodiments is a compound of Formula III, wherein at least one $R_{11}$ is —$SO_2R_{10}$. In some embodiments is a compound of Formula III, wherein each $R_{10}$ is independently $C_1$-$C_6$ alkyl. In some embodiments is a compound of Formula III, wherein each $R_{10}$ is methyl. In some embodiments is a compound of Formula III, wherein $R_4$ is phenyl substituted with one $R_{11}$, wherein $R_{11}$ is —$SO_2R_{10}$ and $R_{10}$ is $C_1$-$C_6$alkyl; or $R_4$ is phenyl substituted with two $R_{11}$, and one $R_{11}$ is —$SO_2R_{10}$ and one $R_{11}$ is optionally substituted $C_1$-$C_6$alkyl. In some embodiments is a compound of Formula III, wherein $R_4$ is phenyl substituted with one $R_{11}$, wherein $R_{11}$ is —$SO_2R_{10}$ and $R_{10}$ is $C_1$-$C_6$alkyl. In some embodiments is a compound of Formula III, wherein $R_4$ is phenyl substituted with one $R_{11}$, wherein $R_{11}$ is —$SO_2R_{10}$ and $R_{10}$ is methyl. In some embodiments is a compound of Formula III, wherein $R_4$ is phenyl substituted with two $R_{11}$, wherein one $R_{11}$ is —$SO_2CH_3$ and one $R_{11}$ is —$CH_2OH$.

In some embodiments is a compound of Formula III, wherein "optionally substituted" means substituted by 1, 2, 3, or 4 substituents independently selected from halo, cyano, $C_1$-$C_4$ alkyl, $C_2$-$C_4$ alkenyl, hydoxy, $C_1$-$C_4$ alkoxy, $C_1$-$C_4$ haloalkyl, $C_1$-$C_4$ haloalkoxy, amino, $C_1$-$C_4$ alkylamino, and di($C_1$-$C_4$ alkyl)amino.

In some embodiments, the compound is a compound of Formula (IIIA):

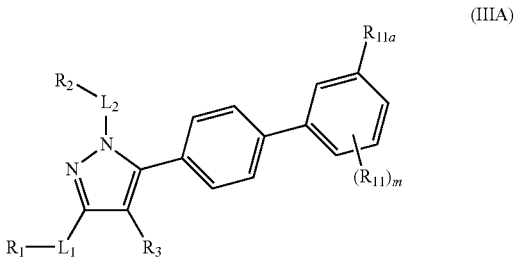

wherein:
m is 0 or 1; and
$R_{11a}$ is —$NR_{10}SO_2R_{10}$, —$SOR_{10}$, —$SO_2R_{10}$, or —$SO_2N(R_{10})_2$;
or a pharmaceutically acceptable salt thereof.

In some embodiments, the compound is a compound of Formula (IIIB):

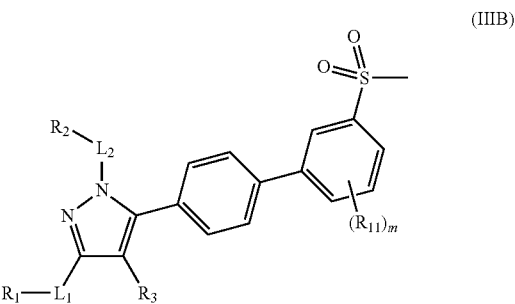

wherein m is 0 or 1;
or a pharmaceutically acceptable salt thereof.

In some embodiments is a compound of Formula III, wherein:
$L_1$ is a bond;
$R_1$ is —C(=O)O$R_8$;
$R_8$ is hydrogen or $C_1$-$C_6$alkyl.
$L_2$ is a $C_1$-$C_6$alkyl;
$R_2$ is H;
$R_4$ is phenyl substituted with at least one $R_{11}$;
each $R_{11}$ is independently $C_1$-$C_6$ alkyl, —$NR_{10}SO_2R_{10}$, —$SOR_{10}$, —$SO_2R_{10}$, or —$SO_2N(R_{10})_2$; wherein said $C_1$-$C_6$ alkyl is optionally substituted by 1 hydroxy;
provided that at least one $R_{11}$ is —$NR_{10}SO_2R_{10}$, —$SOR_{10}$, —$SO_2R_{10}$, or —$SO_2N(R_{10})_2$;
each $R_{10}$ is independently $C_1$-$C_6$ alkyl;
n is 0; and
$R_3$ is hydrogen.

In some embodiments is a compound of Formula III, wherein:
$L_1$ is a bond;
$R_1$ is —C(=O)O$R_8$;
$R_8$ is hydrogen or $C_1$-$C_6$alkyl.
$L_2$ is a $C_1$-$C_6$alkyl;
$R_2$ is H;
$R_4$ is phenyl substituted with at least one $R_{11}$;
each $R_{11}$ is independently $C_1$-$C_6$ alkyl, —$NR_{10}SO_2R_{10}$, —$SOR_{10}$, —$SO_2R_{10}$, or —$SO_2N(R_{10})_2$; wherein said $C_1$-$C_6$ alkyl is optionally substituted by 1 hydroxy;
provided that at least one $R_{11}$ is —$SO_2N(R_{10})_2$;
each $R_{10}$ is independently $C_1$-$C_6$ alkyl;
n is 0; and
$R_3$ is hydrogen.

In some embodiments, the compound is selected from:

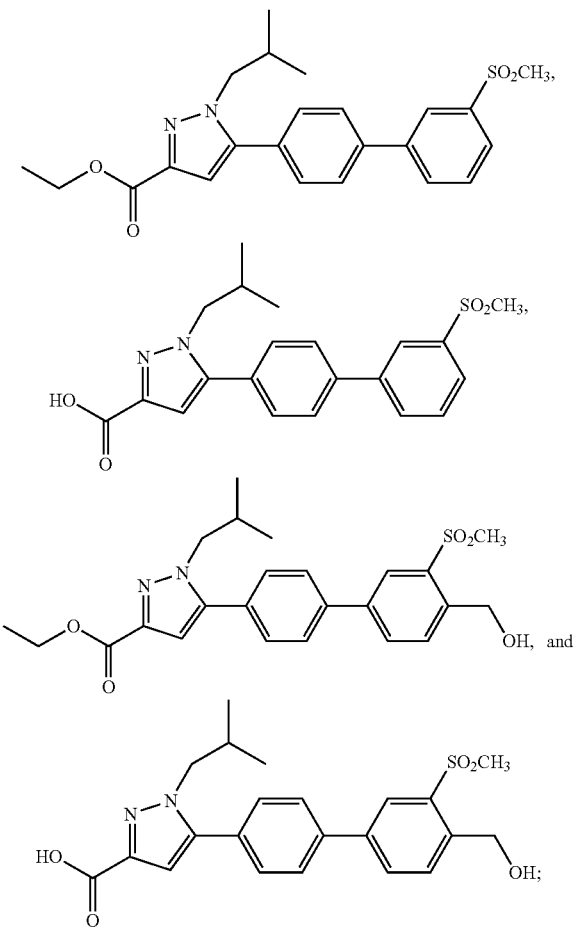

or a pharmaceutically acceptable salt thereof.

In another aspect is a compound of Formula (IV):

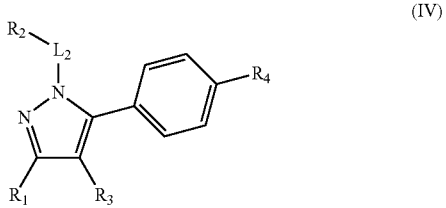

(IV)

wherein:
$R_1$ is $C_1$-$C_6$ alkyl or $C_2$-$C_6$ alkenyl, wherein said $C_1$-$C_6$ alkyl is optionally substituted by 1, 2, 3, or 4 substituents independently selected from hydoxy, $C_1$-$C_4$ alkoxy, and $C_1$-$C_4$ haloalkoxy;
$L_2$ is a $C_1$-$C_6$ alkyl;
$R_2$ is C(=O)O$R_9$;
$R_3$ is hydrogen or $C_1$-$C_6$alkyl;
$R_4$ is phenyl substituted with at least one $R_{11}$;
each $R_9$ is independently hydrogen or $C_1$-$C_6$alkyl;
each $R_{10}$ is independently hydrogen or $C_1$-$C_6$alkyl; and
each $R_{11}$ is independently halogen, nitro, —O$R_{10}$, —N($R_{10}$)$_2$, —CN, —C(=O)$R_{10}$, —C(=O)O$R_{10}$, —C(=O)N($R_{10}$)$_2$, —N$R_{10}$C(=O)$R_{10}$, —N$R_{10}$SO$_2$$R_{10}$, —SO$R_{10}$, —SO$_2$$R_{10}$, —SO$_2$N($R_{10}$)$_2$, —C(=O)OCH$_2$SCH$_3$, $C_1$-$C_6$alkyl, or $C_1$-$C_6$ haloalkyl, wherein said $C_1$-$C_6$ alkyl is optionally substituted by 1, 2, 3, or 4 substituents independently selected from cyano, hydoxy, $C_1$-$C_4$ alkoxy, $C_1$-$C_4$ haloalkoxy, amino, $C_1$-$C_4$ alkylamino, and di($C_1$-$C_4$ alkyl)amino;
provided that at least one $R_{11}$ is —N$R_{10}$C(=O)$R_{10}$, —N$R_{10}$SO$_2$$R_{10}$, —SO$R_{10}$, —SO$_2$$R_{10}$, or —SO$_2$N($R_{10}$)$_2$;
or a pharmaceutically acceptable salt thereof.

In some embodiments is a compound of Formula IV, wherein $R_1$ is $C_2$-$C_4$ alkenyl or $C_1$-$C_3$ alkyl, wherein said $C_1$-$C_3$ alkyl is optionally substituted by 1 hydroxy. In some embodiments is a compound of Formula IV, wherein $R_1$ is —C(=CH$_2$)CH$_3$, isopropyl, or —C(CH$_3$)$_2$OH. In some embodiments is a compound of Formula IV, wherein $L_2$ is —CH$_2$—. In some embodiments is a compound of Formula IV, wherein -$L_2$-$R_2$ is —CH$_2$C(=O)O$R_9$, wherein $R_9$ is $C_1$-$C_6$ alkyl. In some embodiments is a compound of Formula IV, wherein -$L_2$-$R_2$ is —CH$_2$C(=O)O$R_9$, wherein $R_9$ is hydrogen, methyl, or ethyl. In some embodiments is a compound of Formula IV, wherein -$L_2$-$R_2$ is —CH$_2$C(=O)OH. In some embodiments is a compound of Formula IV, wherein -$L_2$-$R_2$ is —CH$_2$C(=O)O-ethyl. In some embodiments is a compound of Formula IV, wherein $R_3$ is hydrogen.

In some embodiments is a compound of Formula IV, $R_4$ is phenyl substituted with at least one $R_{11}$. In some embodiments is a compound of Formula IV, wherein at least one $R_{11}$ is —N$R_{10}$SO$_2$$R_{10}$, —SO$R_{10}$, —SO$_2$$R_{10}$, or —SO$_2$N($R_{10}$)$_2$. In some embodiments is a compound of Formula IV, wherein at least one $R_{11}$ is —SO$_2$$R_{10}$. In some embodiments is a compound of Formula IV, wherein each $R_{10}$ is independently $C_1$-$C_6$ alkyl. In some embodiments is a compound of Formula IV, wherein each $R_{10}$ is methyl. In some embodiments is a compound of Formula IV, wherein $R_4$ is phenyl substituted with one $R_{11}$, wherein $R_{11}$ is —SO$_2$$R_{10}$ and $R_{10}$ is $C_1$-$C_6$alkyl; or $R_4$ is phenyl substituted with two $R_{11}$, and one $R_{11}$ is —SO$_2$$R_{10}$ and one $R_{11}$ is optionally substituted $C_1$-$C_6$alkyl. In some embodiments is a compound of Formula IV, wherein $R_4$ is phenyl substituted with one $R_{11}$, wherein $R_{11}$ is —SO$_2$$R_{10}$ and $R_{10}$ is $C_1$-$C_6$alkyl. In some embodiments is a compound of Formula IV, wherein $R_4$ is phenyl substituted with one $R_{11}$, wherein $R_{11}$ is —SO$_2$$R_{10}$ and $R_{10}$ is methyl. In some embodiments is a compound of Formula IV, wherein $R_4$ is phenyl substituted with two $R_{11}$, wherein one $R_{11}$ is —SO$_2$CH$_3$ and one $R_{11}$ is —CH$_2$OH.

In some embodiments, the compound is a compound of Formula (IVA):

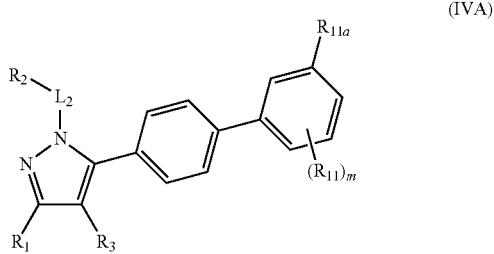

(IVA)

wherein:
m is 0 or 1; and
$R_{11a}$ is —N$R_{10}$SO$_2$$R_{10}$, —SO$R_{10}$, —SO$_2$$R_{10}$, or —SO$_2$N($R_{10}$)$_2$;
or a pharmaceutically acceptable salt thereof.

In some embodiments, the compound is a compound of Formula (IVB):

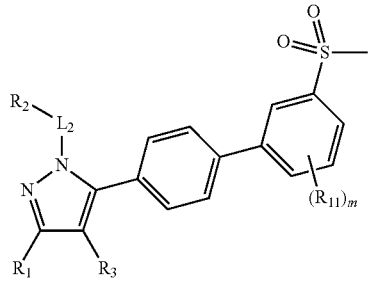

(IVB)

wherein m is 0 or 1;
or a pharmaceutically acceptable salt thereof.

In some embodiments is a compound of Formula IV, wherein:
$R_1$ is $C_2$-$C_4$ alkenyl or $C_1$-$C_3$ alkyl, wherein said $C_1$-$C_3$ alkyl is optionally substituted by 1 hydroxy;
-$L_2$-$R_2$ is —$CH_2$C(=O)O$R_9$;
$R_9$ is $C_1$-$C_6$ alkyl;
$R_4$ is phenyl substituted with at least one $R_{11}$;
each $R_{11}$ is independently $C_1$-$C_6$ alkyl, —$NR_{10}SO_2R_{10}$, —$SOR_{10}$, —$SO_2R_{10}$, or —$SO_2N(R_{10})_2$; wherein said $C_1$-$C_6$ alkyl is optionally substituted by 1 hydroxy;
provided that at least one $R_{11}$ is —$NR_{10}SO_2R_{10}$, —$SOR_{10}$, —$SO_2R_{10}$, or —$SO_2N(R_{10})_2$;
each $R_{10}$ is independently $C_1$-$C_6$ alkyl; and
$R_3$ is hydrogen.

In some embodiments is a compound of Formula IV, wherein:
$R_1$ is $C_2$-$C_4$ alkenyl or $C_1$-$C_3$alkyl, wherein said $C_1$-$C_3$ alkyl is optionally substituted by 1 hydroxy;
-$L_2$-$R_2$ is —$CH_2$C(=O)O$R_9$;
$R_9$ is $C_1$-$C_6$ alkyl;
$R_4$ is phenyl substituted with at least one $R_{11}$;
each $R_{11}$ is independently $C_1$-$C_6$ alkyl, —$NR_{10}SO_2R_{10}$, —$SOR_{10}$, —$SO_2R_{10}$, or —$SO_2N(R_{10})_2$; wherein said $C_1$-$C_6$ alkyl is optionally substituted by 1 hydroxy;
provided that at least one $R_{11}$ is —$SO_2N(R_{10})_2$;
each $R_{10}$ is independently $C_1$-$C_6$ alkyl; and
$R_3$ is hydrogen.

In some embodiments, the compound is selected from:

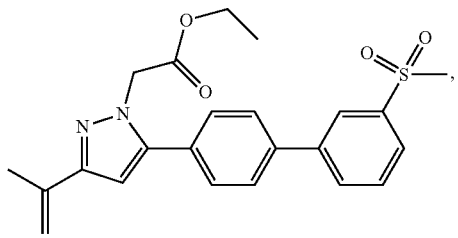

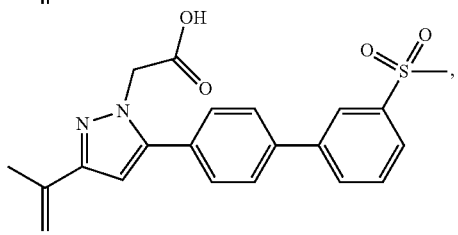

-continued

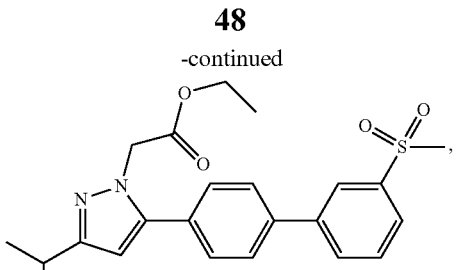

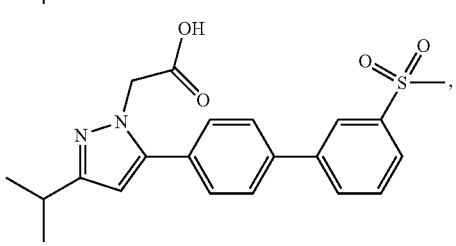

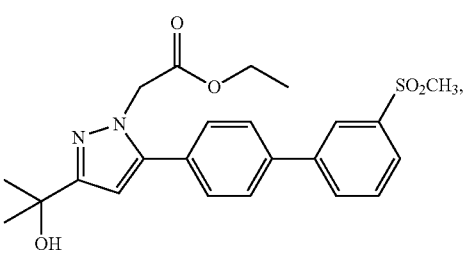

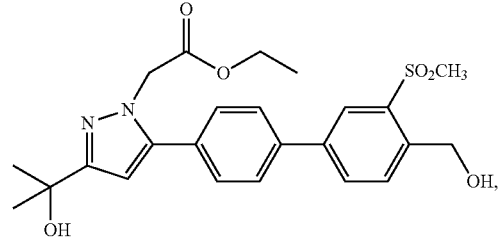

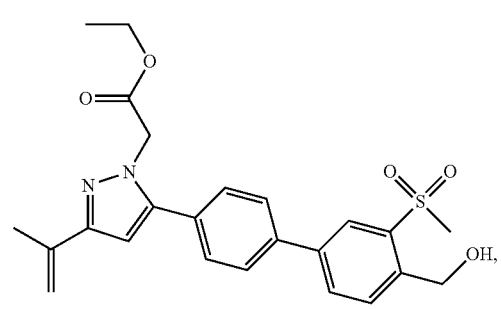

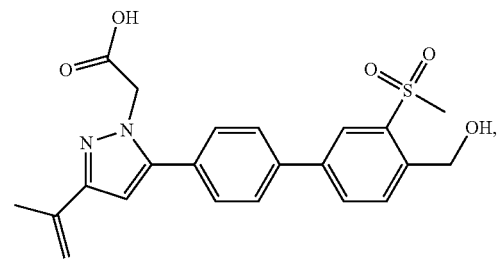

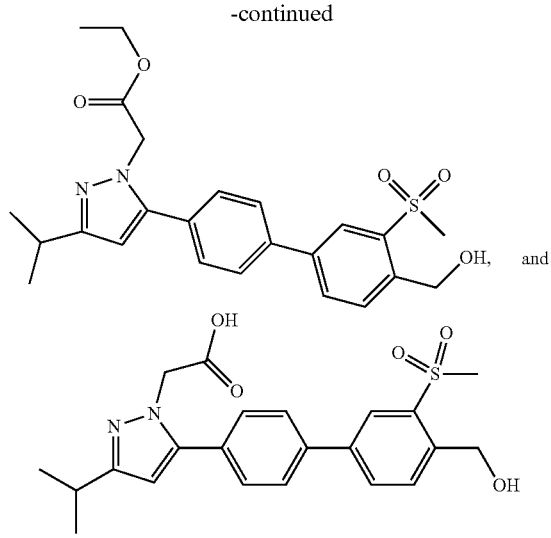
or a pharmaceutically acceptable salt thereof.
Any combination of the groups described above for the various variables is contemplated herein. Throughout the specification, groups and substituents thereof can be chosen by one skilled in the field to provide stable moieties and compounds.
In some embodiments is a compound selected from:
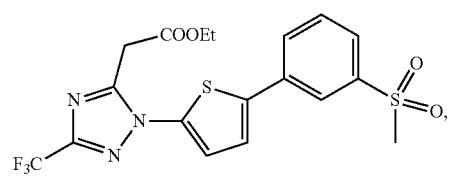
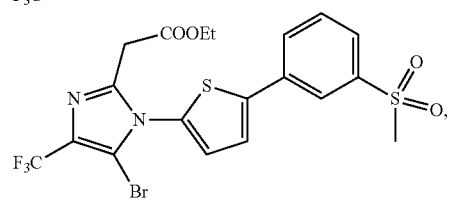
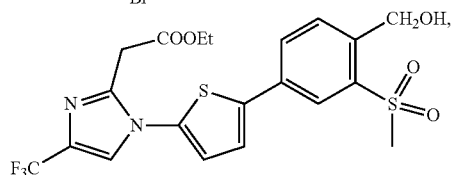
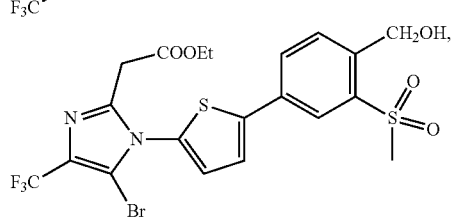
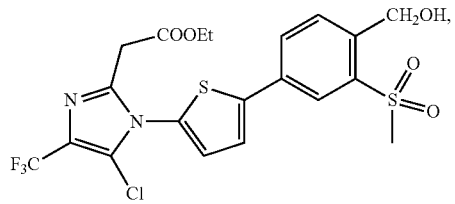
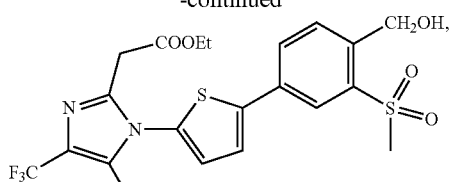
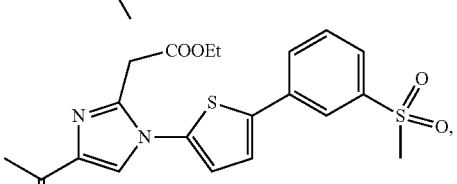
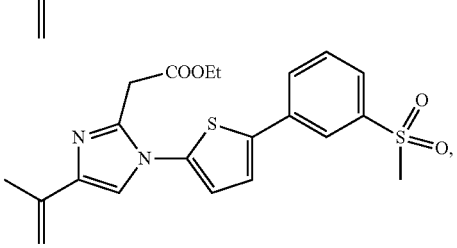
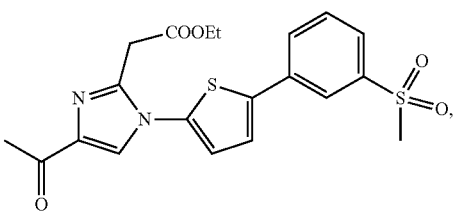
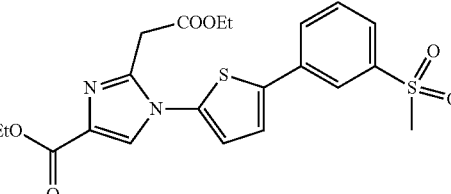
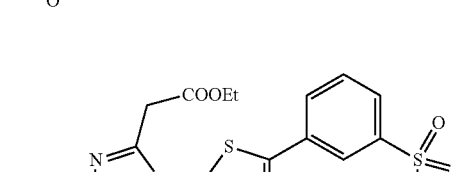
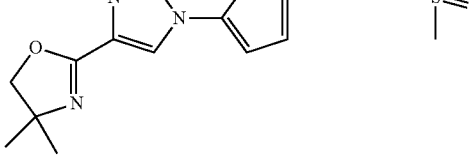
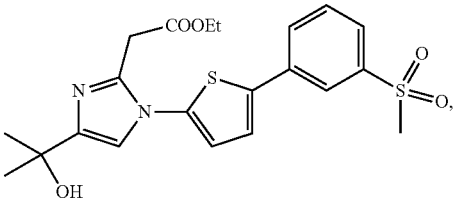

-continued

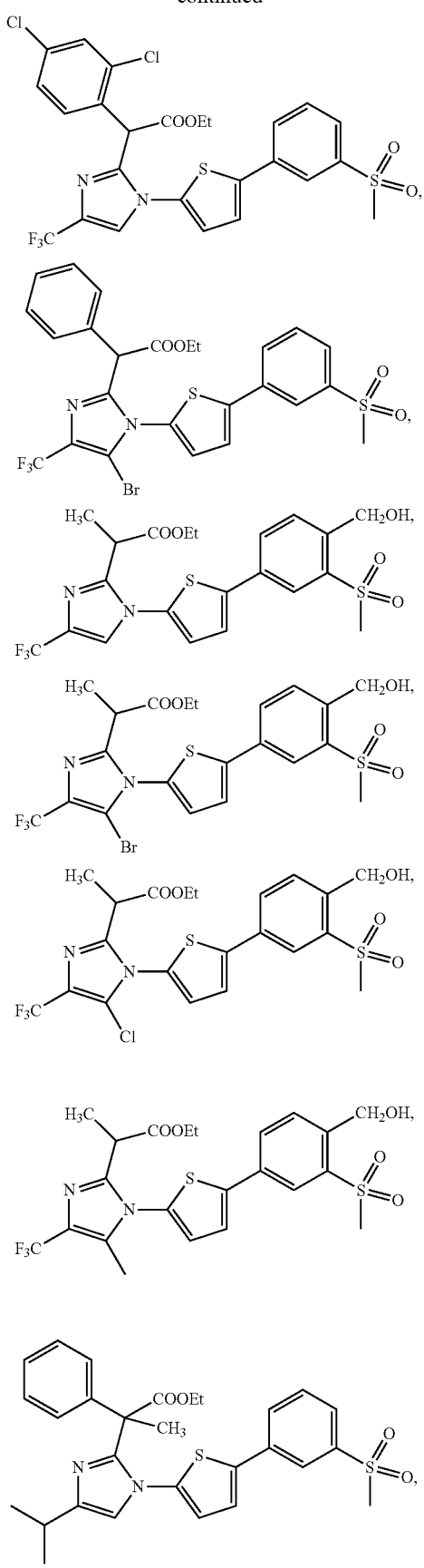

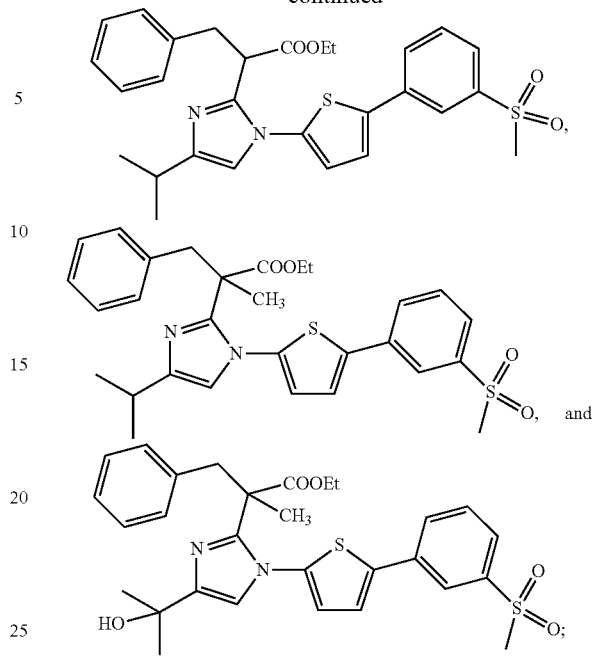

or a pharmaceutically acceptable salt, pharmaceutically acceptable solvate, or pharmaceutically acceptable prodrug thereof.

Additional LXR Modulators

Also disclosed herein are LXR modulators which have been structurally modified to incorporate a carboxylic ester functional group to produce an LXR soft-drug. The carboxylic ester LXR modulators described herein retain LXR activity. However, the corresponding carboxylic acids of the ester derivatives lack LXR activity as the LXR binding pocket that binds the active esters does not prefer a polar/charged species such as the carboxylic acids. Thus, the carboxylic esters described herein provide an optimal delivery for a topically administered LXR modulator. The carboxylic esters are potent LXR modulators which induce the expression and/or protein levels of LXRs in skin cells. However, upon hydrolysis, the corresponding carboxylic acids are devoid of LXR activity. Thus, the carboxylic esters will have little or no systemic exposure as they are readily hydrolyzed upon entering the systemic circulation (Scheme A).

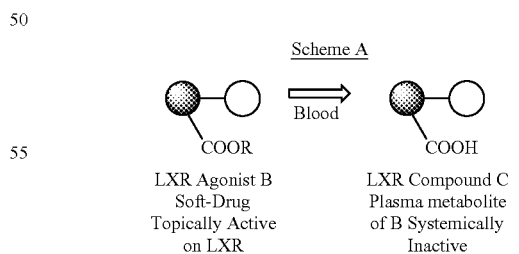

Scheme B depicts a general procedure for the identification of topically administered LXR modulators. Following the identification of systemically administered LXR modulator compounds, a region within the LXR modulator molecule is identified whereby a carboxylic ester functional group is attached to the molecule while maintaining LXR activity. The corresponding carboxylic acid is then synthesized and tested in various LXR assays to establish the loss of LXR activity for the carboxylic acid.

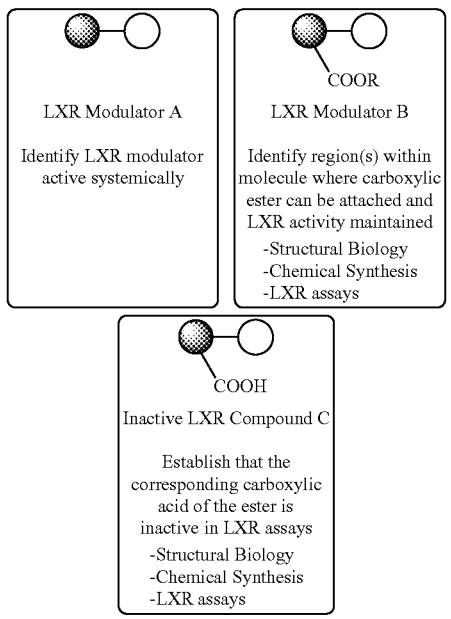

The procedure outlined in Scheme B is illustrated by, but not limited to, the following examples:

LXR modulators described in WO 2005/113499 are structurally modified to attach to the compound a carboxylic ester functional group. The carboxylic ester is LXR active while the corresponding carboxylic acid is LXR inactive (Scheme C). The compounds, and methods for their synthesis, disclosed in WO 2005/113499 are incorporated herein by reference.

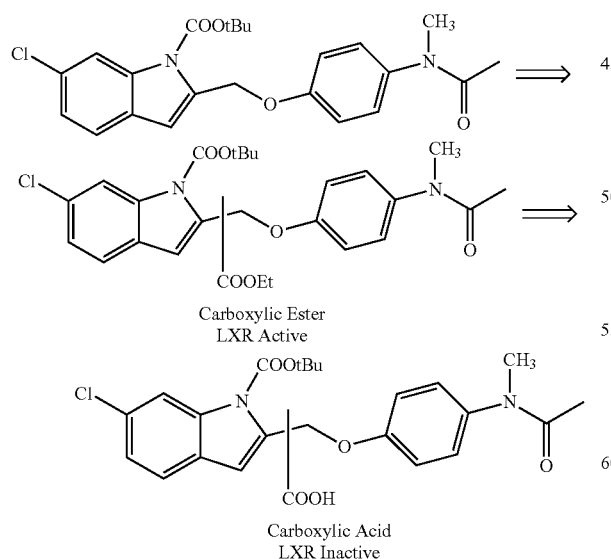

LXR modulators described in WO 2006/109633 are structurally modified to attach to the compound a carboxylic ester functional group. The carboxylic ester is LXR active while the corresponding carboxylic acid is LXR inactive (Scheme D). The compounds, and methods for their synthesis, disclosed in WO 2006/109633 are incorporated herein by reference.

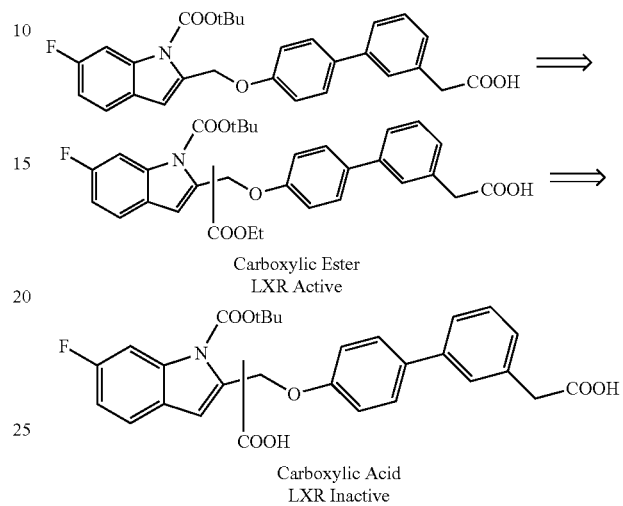

LXR modulators described in WO 2006/003923 are structurally modified to attach to the compound a carboxylic ester functional group. The carboxylic ester is LXR active while the corresponding carboxylic acid is LXR inactive (Scheme E). The compounds, and methods for their synthesis, disclosed in WO 2006/003923 are incorporated herein by reference.

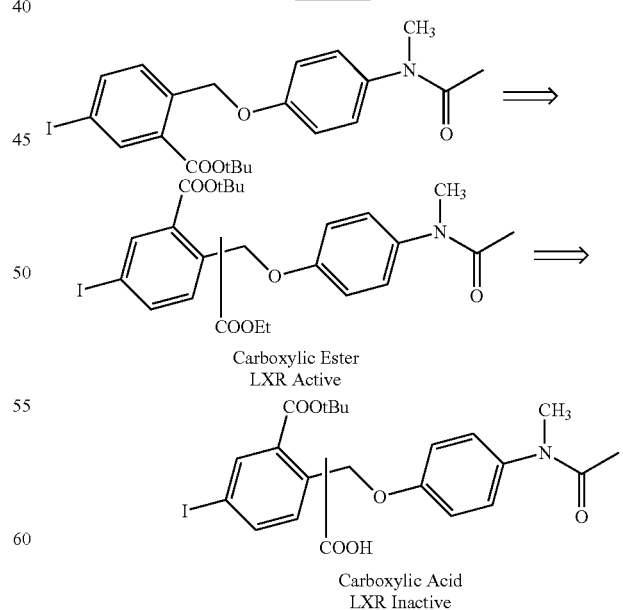

LXR modulators described in WO 2009/086138 are structurally modified to attach to the compound a carboxylic ester functional group. The carboxylic ester is LXR active while the corresponding carboxylic acid is LXR inactive (Scheme F). The compounds, and methods for their synthesis, disclosed in WO 2009/086138 are incorporated herein by reference.

Scheme F

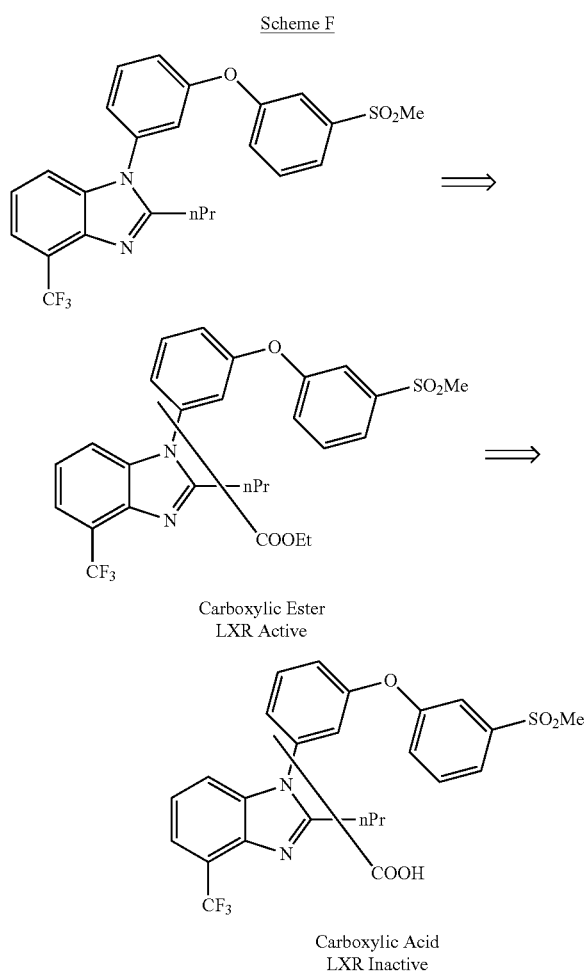

Carboxylic Ester
LXR Active

Carboxylic Acid
LXR Inactive

LXR modulators described in WO 2009/086123 are structurally modified to attach to the compound a carboxylic ester functional group. The carboxylic ester is LXR active while the corresponding carboxylic acid is LXR inactive (Scheme G). The compounds, and methods for their synthesis, disclosed in WO 2009/086123 are incorporated herein by reference.

Scheme G

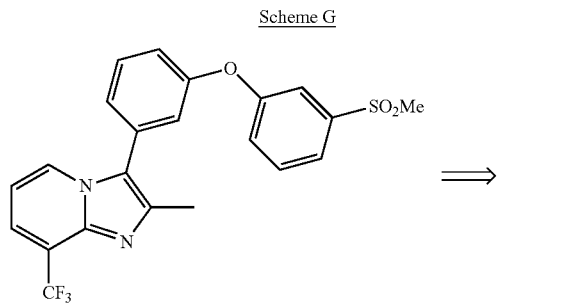

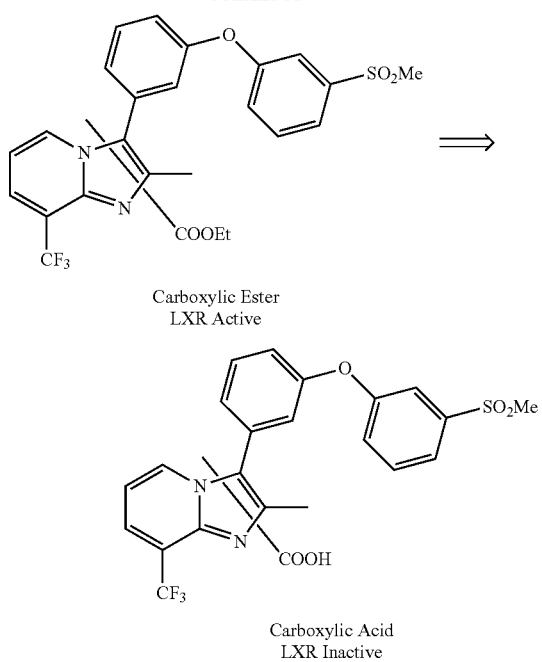

Carboxylic Ester
LXR Active

Carboxylic Acid
LXR Inactive

LXR modulators described in WO 2009/150109 are structurally modified to attach to the compound a carboxylic ester functional group. The carboxylic ester is LXR active while the corresponding carboxylic acid is LXR inactive (Scheme H). The compounds, and methods for their synthesis, disclosed in WO 2009/150109 are incorporated herein by reference.

Scheme H

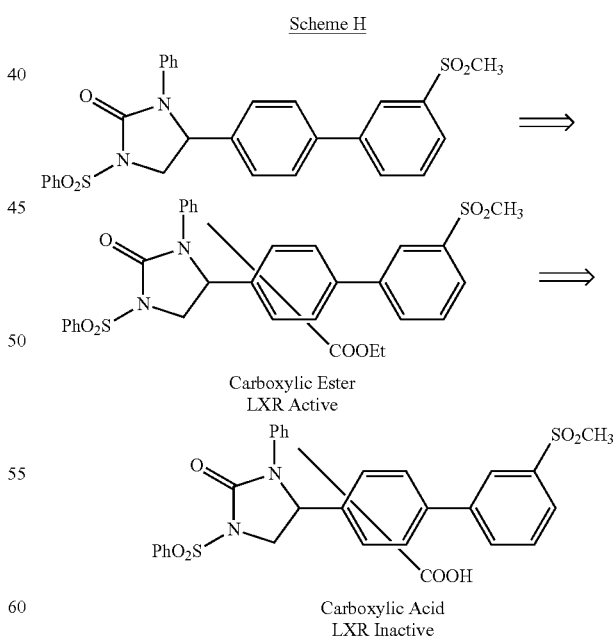

Carboxylic Ester
LXR Active

Carboxylic Acid
LXR Inactive

LXR modulators described in WO 2009/021868 are structurally modified to attach to the compound a carboxylic ester functional group. The carboxylic ester is LXR active while the corresponding carboxylic acid is LXR inactive (Scheme I). The compounds, and methods for their synthesis, disclosed in WO 2009/021868 are incorporated herein by reference.

Scheme I

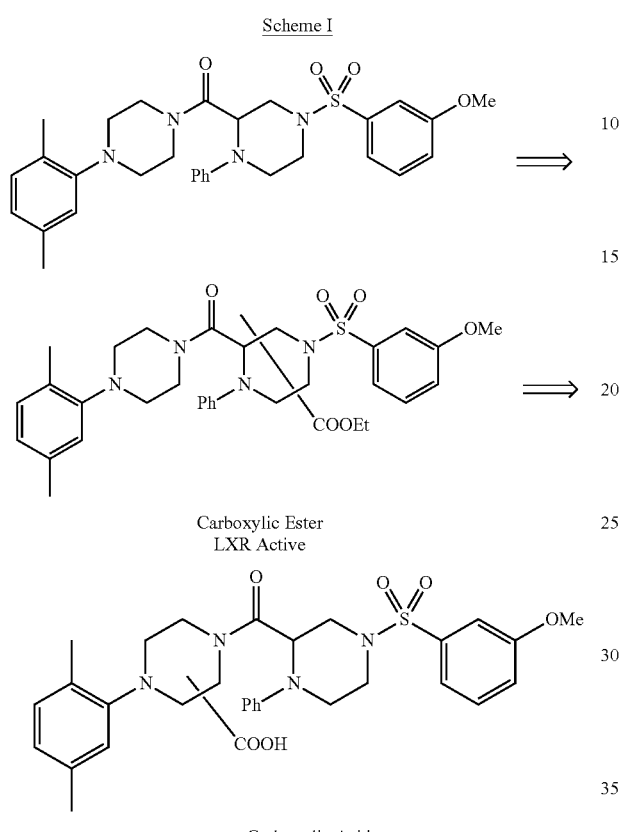

Carboxylic Ester
LXR Active

Carboxylic Acid
LXR Inactive

LXR modulators described in WO 2004/058717 are structurally modified to attach to the compound a carboxylic ester functional group. The carboxylic ester is LXR active while the corresponding carboxylic acid is LXR inactive (Scheme J). The compounds, and methods for their synthesis, disclosed in WO 2004/058717 are incorporated herein by reference.

Scheme J

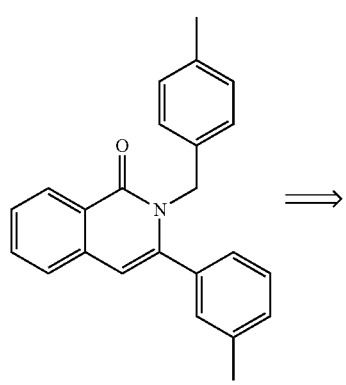

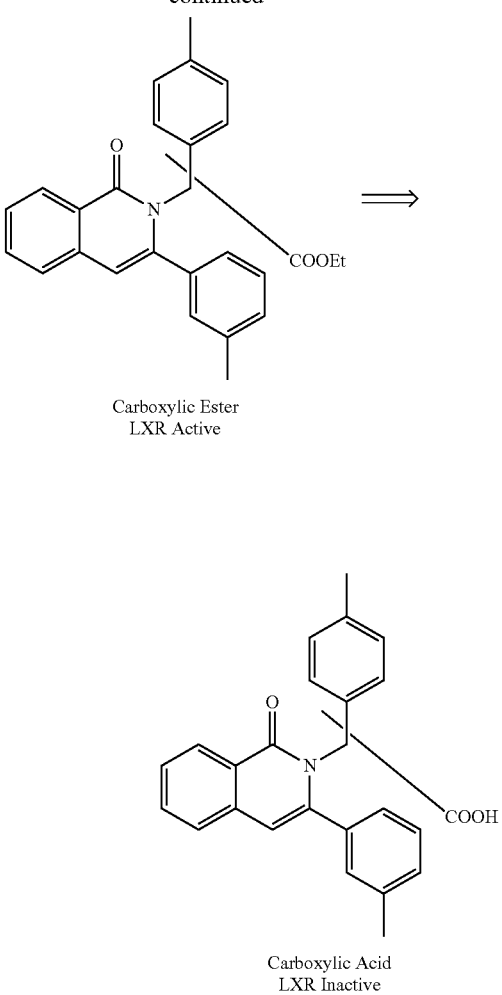

Carboxylic Ester
LXR Active

Carboxylic Acid
LXR Inactive

LXR modulators described in WO 2010/138598 are structurally modified to attach to the compound a carboxylic ester functional group. The carboxylic ester is LXR active while the corresponding carboxylic acid is LXR inactive (Scheme K). The compounds, and methods for their synthesis, disclosed in WO 2010/138598 are incorporated herein by reference.

Scheme K

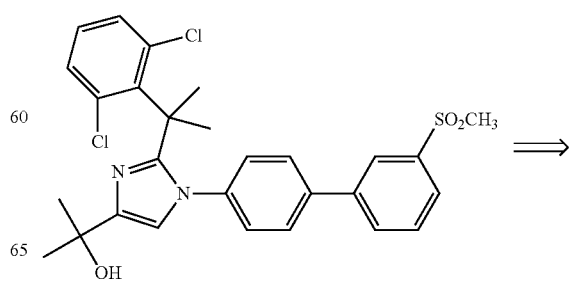

-continued

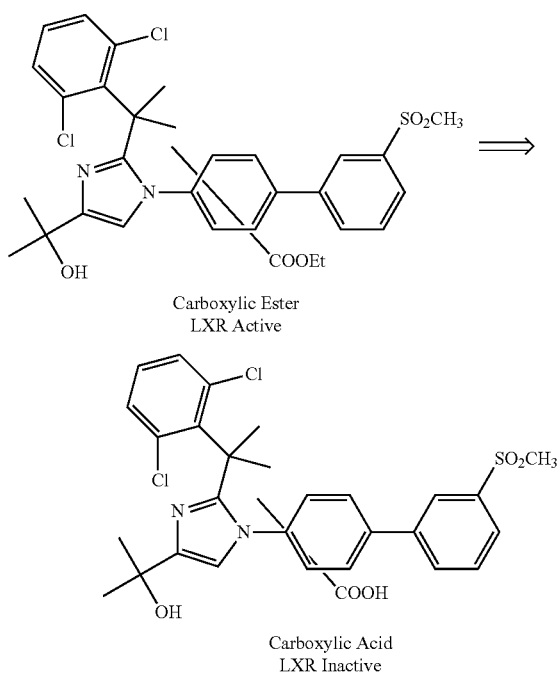

Carboxylic Ester
LXR Active

Carboxylic Acid
LXR Inactive

LXR modulators described in WO 2010/059627 are structurally modified to attach to the compound a carboxylic ester functional group. The carboxylic ester is LXR active while the corresponding carboxylic acid is LXR inactive (Scheme L). The compounds, and methods for their synthesis, disclosed in WO 2010/059627 are incorporated herein by reference.

Scheme L

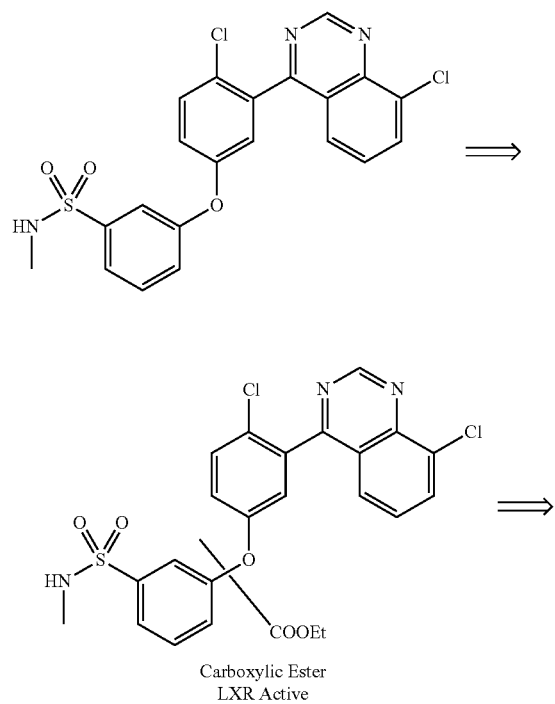

Carboxylic Ester
LXR Active

-continued

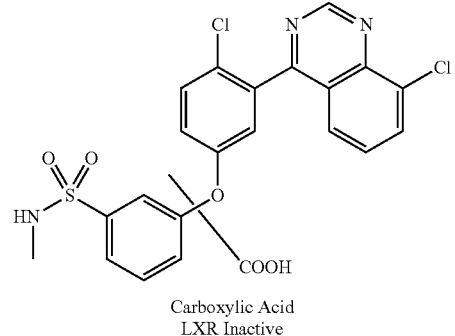

Carboxylic Acid
LXR Inactive

LXR modulators described in WO 2010/054229 are structurally modified to attach to the compound a carboxylic ester functional group. The carboxylic ester is LXR active while the corresponding carboxylic acid is LXR inactive (Scheme M). The compounds, and methods for their synthesis, disclosed in WO 2010/054229 are incorporated herein by reference.

Scheme M

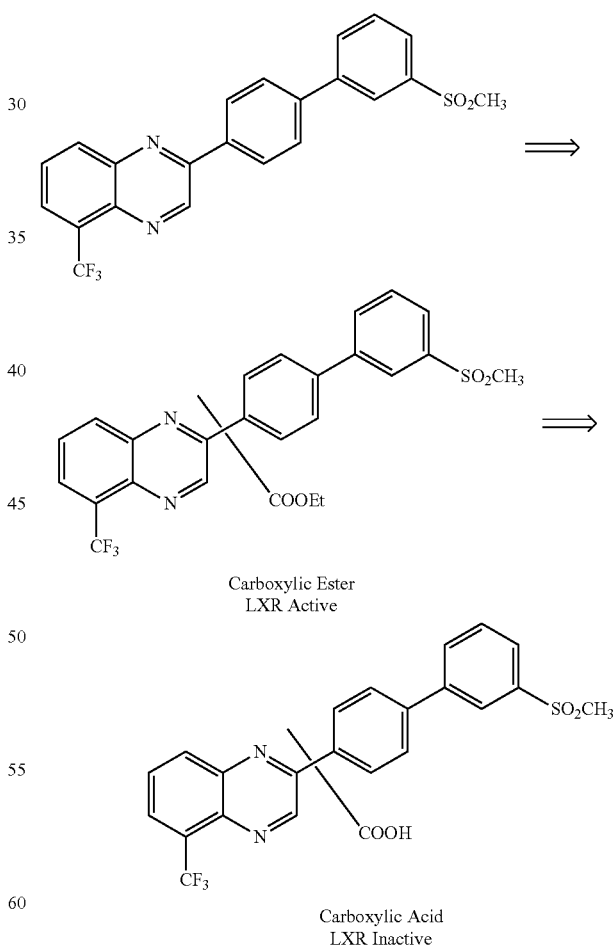

Carboxylic Ester
LXR Active

Carboxylic Acid
LXR Inactive

LXR modulators described in WO 2009/020683 are structurally modified to attach to the compound a carboxylic ester functional group. The carboxylic ester is LXR active while the corresponding carboxylic acid is LXR inactive (Scheme N). The compounds, and methods for their synthesis, disclosed in WO 2009/020683 are incorporated herein by reference.

Scheme N

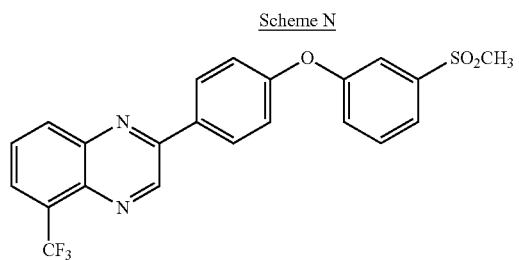

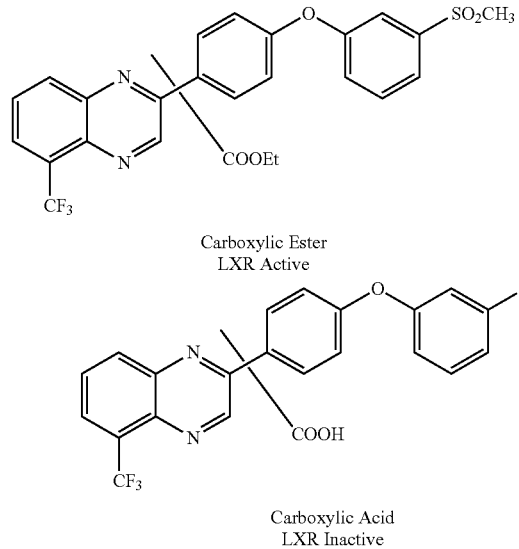

Carboxylic Ester
LXR Active

Carboxylic Acid
LXR Inactive

LXR modulators described in WO 2008/049047 are structurally modified to attach to the compound a carboxylic ester functional group. The carboxylic ester is LXR active while the corresponding carboxylic acid is LXR inactive (Scheme O). The compounds, and methods for their synthesis, disclosed in WO 2008/049047 are incorporated herein by reference.

Scheme O

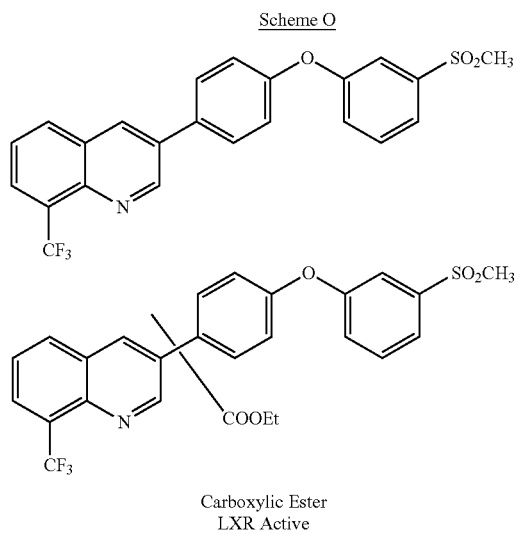

Carboxylic Ester
LXR Active

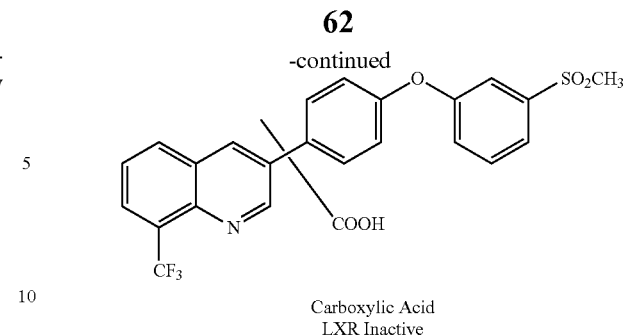

Carboxylic Acid
LXR Inactive

LXR modulators described in WO 2007/092065 are structurally modified to attach to the compound a carboxylic ester functional group. The carboxylic ester is LXR active while the corresponding carboxylic acid is LXR inactive (Scheme P). The compounds, and methods for their synthesis, disclosed in WO 2007/092065 are incorporated herein by reference.

Scheme P

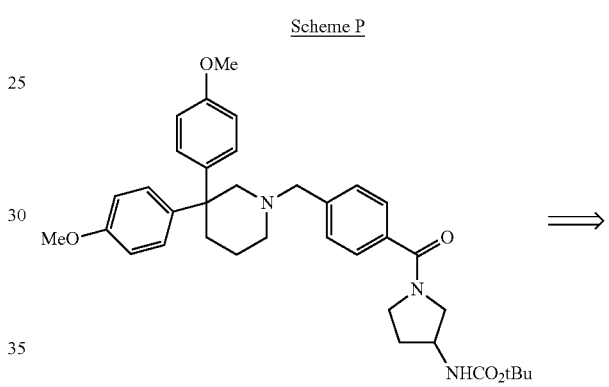

Carboxylic Ester
LXR Active

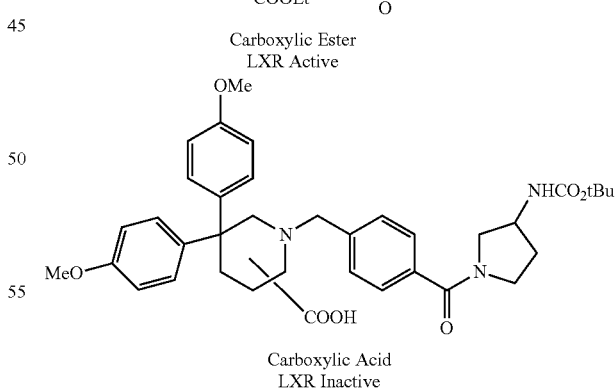

Carboxylic Acid
LXR Inactive

LXR modulators described in WO 2007/002559 are structurally modified to attach to the compound a carboxylic ester functional group. The carboxylic ester is LXR active while the corresponding carboxylic acid is LXR inactive (Scheme Q). The compounds, and methods for their synthesis, disclosed in WO 2007/002559 are incorporated herein by reference.

Scheme Q

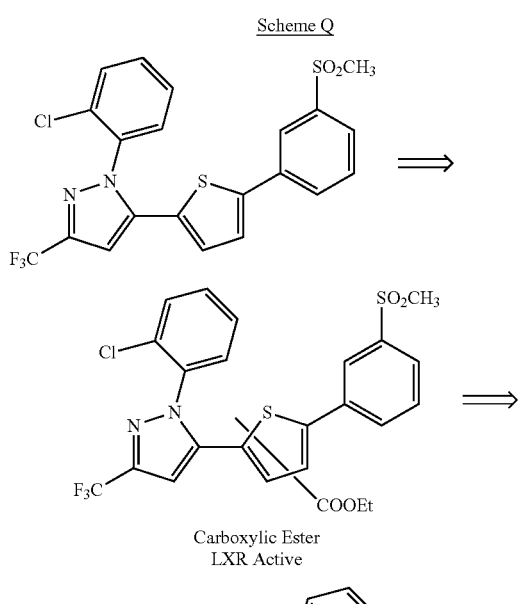

Carboxylic Ester
LXR Active

Carboxylic Acid
LXR Inactive

LXR modulators described in WO 2007/002563 are structurally modified to attach to the compound a carboxylic ester functional group. The carboxylic ester is LXR active while the corresponding carboxylic acid is LXR inactive (Scheme R). The compounds, and methods for their synthesis, disclosed in WO 2007/002563 are incorporated herein by reference.

Scheme R

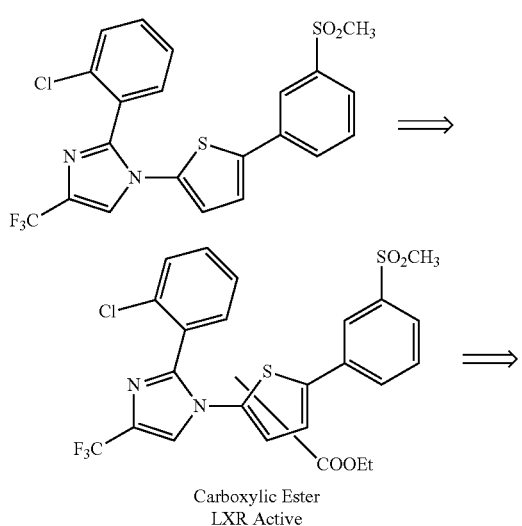

Carboxylic Ester
LXR Active

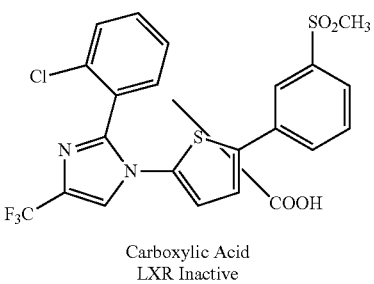

Carboxylic Acid
LXR Inactive

LXR modulators described in US 2006/0030612 are structurally modified to attach to the compound a carboxylic ester functional group. The carboxylic ester is LXR active while the corresponding carboxylic acid is LXR inactive (Scheme S). The compounds, and methods for their synthesis, disclosed in US 2006/0030612 are incorporated herein by reference.

Scheme S

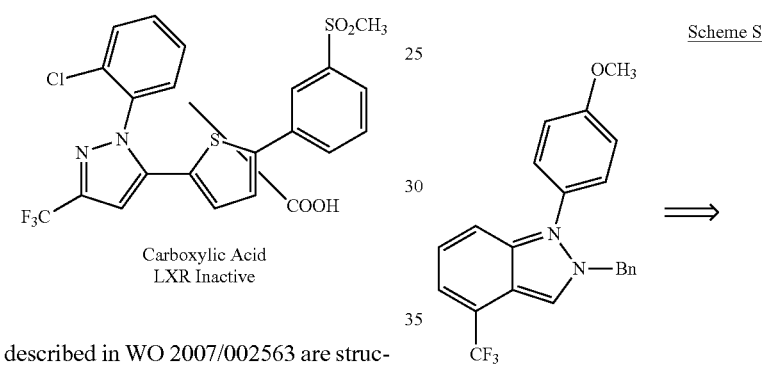

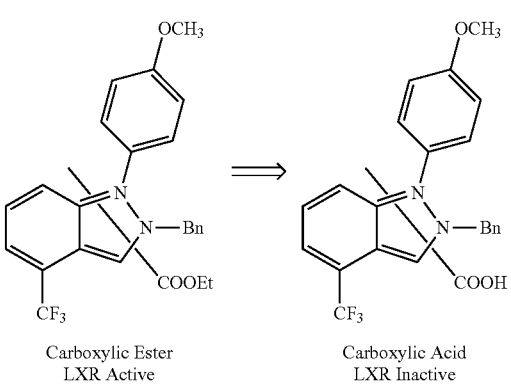

Carboxylic Ester
LXR Active

Carboxylic Acid
LXR Inactive

LXR modulators described in US 2006/0261319 are structurally modified to attach to the compound a carboxylic ester functional group. The carboxylic ester is LXR active while the corresponding carboxylic acid is LXR inactive (Scheme T). The compounds, and methods for their synthesis, disclosed in US 2006/0261319 are incorporated herein by reference.

Scheme T

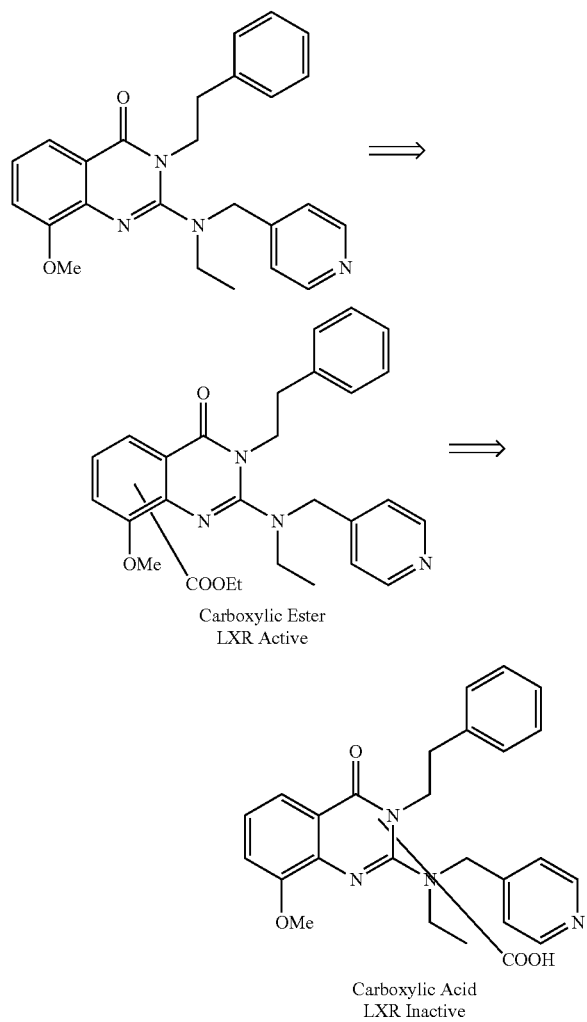

LXR modulators described in WO 2002024632 are structurally modified to attach to the compound a carboxylic ester functional group. The carboxylic ester is LXR active while the corresponding carboxylic acid is LXR inactive (Scheme U). The compounds, and methods for their synthesis, disclosed in WO 2002024632 are incorporated herein by reference.

Scheme U

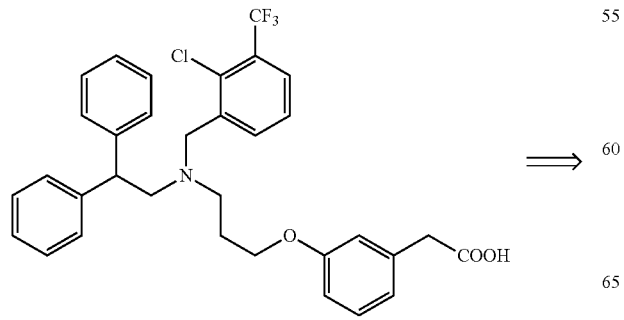

LXR modulators described in WO 2003099769 are structurally modified to attach to the compound a carboxylic ester functional group. The carboxylic ester is LXR active while the corresponding carboxylic acid is LXR inactive (Scheme V). The compounds, and methods for their synthesis, disclosed in WO 2003099769 are incorporated herein by reference.

Scheme V

-continued

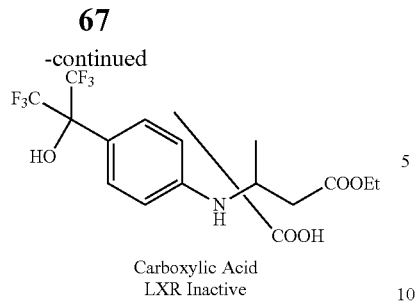

Carboxylic Acid
LXR Inactive

LXR modulators described in WO 2003099775 are structurally modified to attach to the compound a carboxylic ester functional group. The carboxylic ester is LXR active while the corresponding carboxylic acid is LXR inactive (Scheme W). The compounds, and methods for their synthesis, disclosed in WO 2003099775 are incorporated herein by reference.

Scheme W

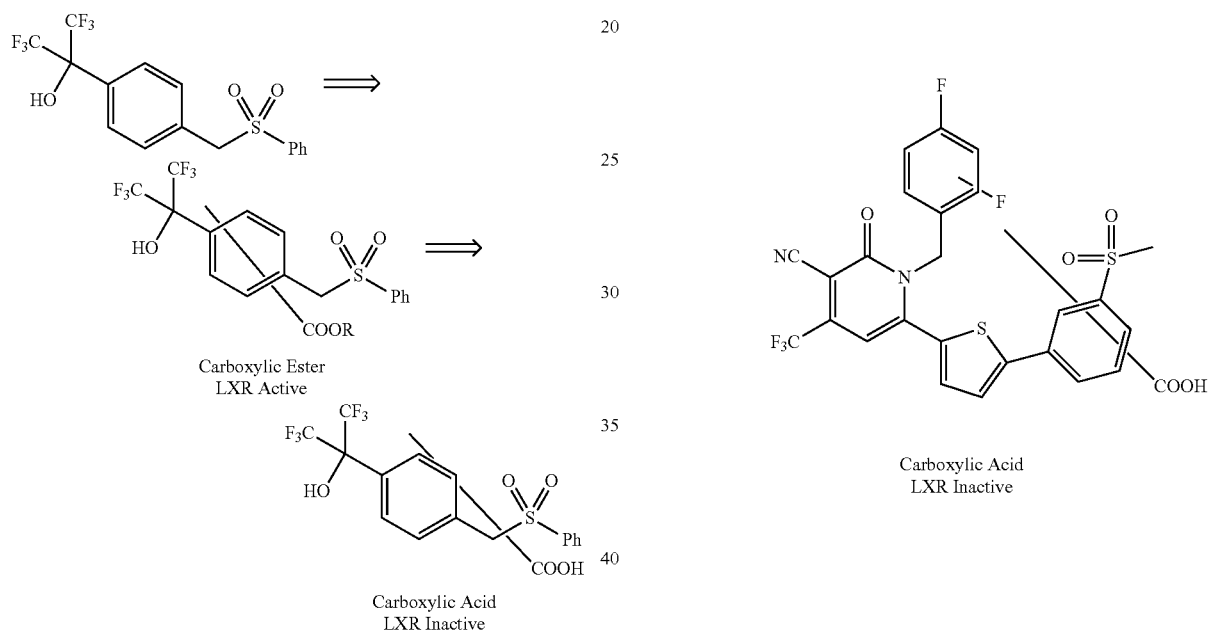

Carboxylic Ester
LXR Active

Carboxylic Acid
LXR Inactive

LXR modulators described in US 20050080111 are structurally modified to attach to the compound a carboxylic ester functional group. The carboxylic ester is LXR active while the corresponding carboxylic acid is LXR inactive (Scheme X). The compounds, and methods for their synthesis, disclosed in US 20050080111 are incorporated herein by reference.

Scheme X

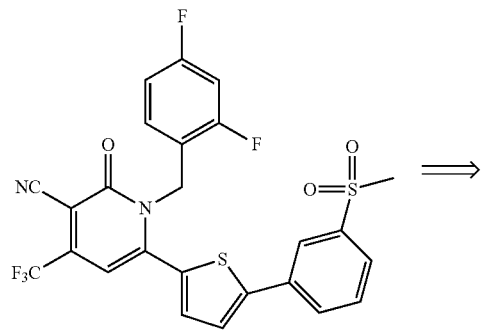

-continued

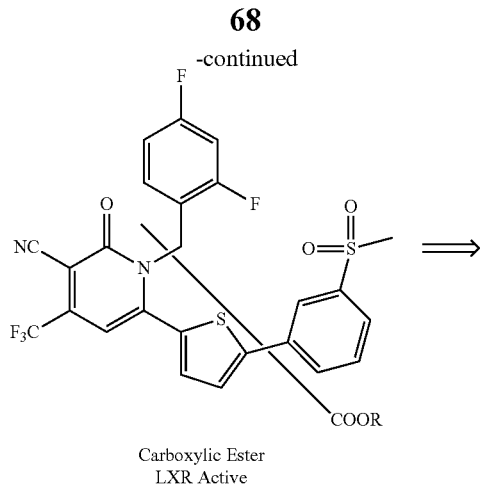

Carboxylic Ester
LXR Active

Carboxylic Acid
LXR Inactive

LXR modulators described in WO 2005023782 are structurally modified to attach to the compound a carboxylic ester functional group. The carboxylic ester is LXR active while the corresponding carboxylic acid is LXR inactive (Scheme Y). The compounds, and methods for their synthesis, disclosed in WO 2005023782 are incorporated herein by reference.

Scheme Y

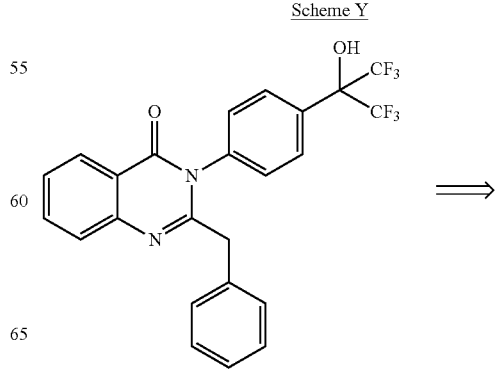

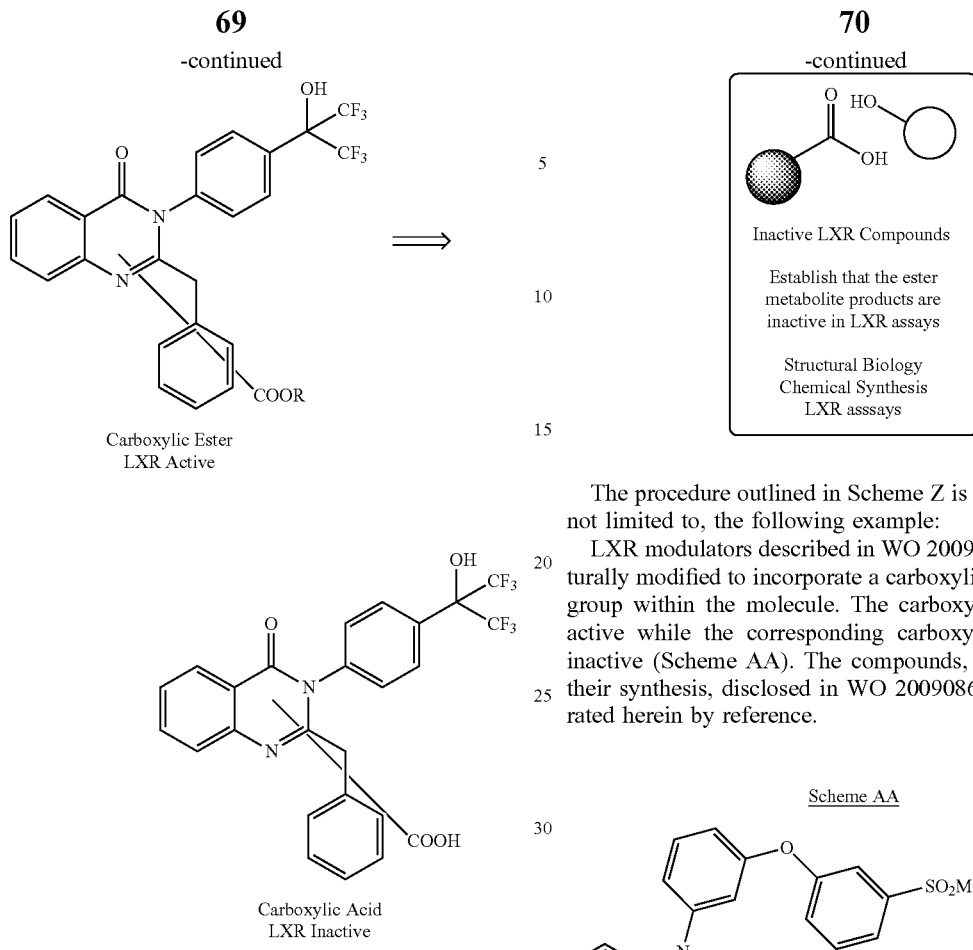

Scheme Z depicts another procedure for the identification of topically administered LXR modulators. Following the identification of systemically administered LXR modulator compounds, a region within the LXR modulator molecule is identified whereby a carboxylic ester functional group is incorporated within the molecule while maintaining LXR activity. The corresponding carboxylic ester hydrolysis products are then synthesized and tested in various LXR assays to establish the loss of LXR activity for these compounds.

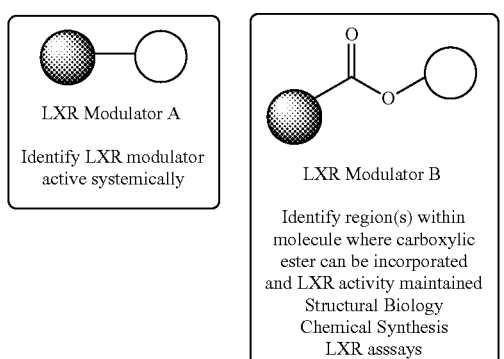

The procedure outlined in Scheme Z is illustrated by, but not limited to, the following example:

LXR modulators described in WO 2009086138 are structurally modified to incorporate a carboxylic ester functional group within the molecule. The carboxylic ester is LXR active while the corresponding carboxylic acid is LXR inactive (Scheme AA). The compounds, and methods for their synthesis, disclosed in WO 2009086138 are incorporated herein by reference.

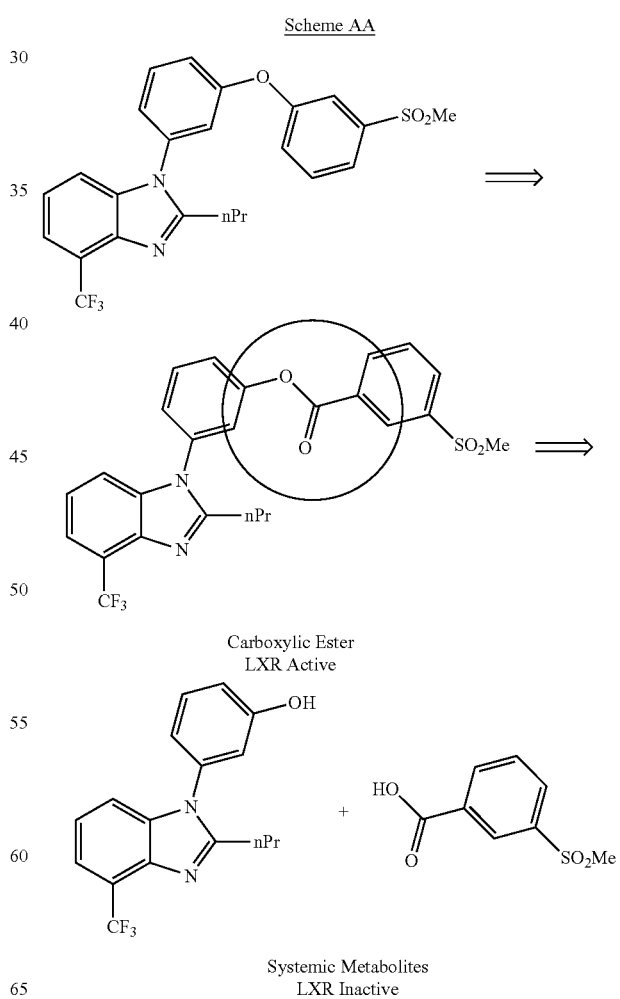

In some embodiments described herein is a pharmaceutical composition of any one of the carboxylic esters disclosed above wherein the carboxylic ester is formulated for topical administration.

In some embodiments, the therapeutic agent(s) (e.g. compound of Formula I, IA, IB, II, IIA, IIB, III, IIIA, IIIB, IV, IVA, and IVB) is present in the pharmaceutical composition as a pharmaceutically acceptable salt. In some embodiments, any compound described above is suitable for any method or composition described herein.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of Formula I, IA, IB, II, IIA, IIB, III, IIIA, IIIB, IV, IVA, and IVB is used as a single enantiomer. In some embodiments, a compound of Formula I, IA, IB, II, IIA, IIB, III, IIIA, IIIB, IV, IVA, and IVB is used as a racemic mixture.

The methods and formulations described herein include the use of N-oxides (if appropriate), crystalline forms (also known as polymorphs), or pharmaceutically acceptable salts of compounds having the structures presented herein, as well as active metabolites of these compounds having the same type of activity. In some situations, compounds may exist as tautomers. All tautomers are included within the scope of the compounds presented herein. In specific embodiments, the compounds described herein, or salts thereof, exist in solvated forms with pharmaceutically acceptable solvents such as water, ethanol, and the like. In other embodiments, the compounds described herein, or salts thereof, exist in unsolvated form.

In some embodiments, the compounds of Formula I, IA, IB, II, IIA, IIB, III, IIIA, IIIB, IV, IVA, and IVB described herein, or salts thereof, include solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol.

In some embodiments, sites on the compounds of Formula I, IA, IB, II, IIA, IIB, III, IIIA, IIIB, IV, IVA, and IVB disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds of Formula I, IA, IB, II, IIA, IIB, III, IIIA, IIIB, IV, IVA, and IVB disclosed herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements.

In some embodiments, compounds described herein, such as compounds of Formula I, IA, IB, II, IIA, IIB, III, IIIA, IIIB, IV, IVA, and IVB, are in various forms, including but not limited to, amorphous forms, milled forms and nanoparticulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein.

A general synthetic scheme for the preparation of the compounds described herein is depicted in Scheme 1.

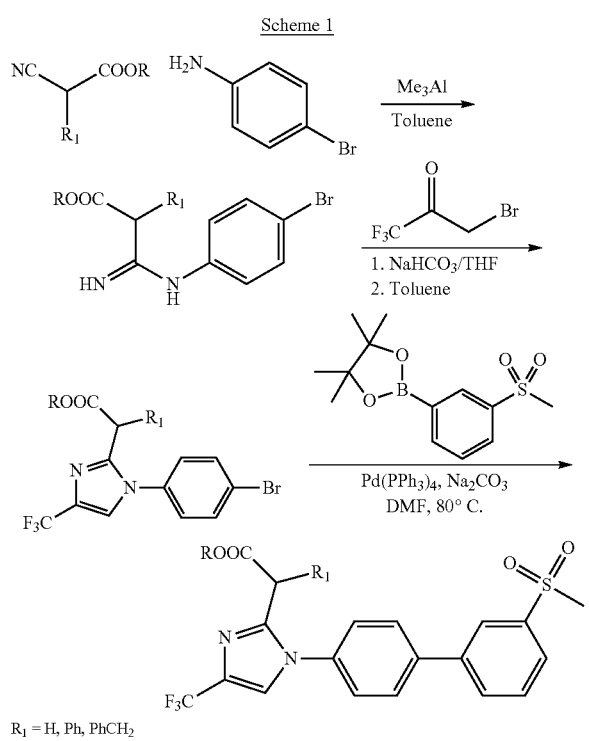

R$_1$ = H, Ph, PhCH$_2$

Formation of Covalent Linkages by Reaction of an Electrophile with a Nucleophile The compounds described herein can be modified using various electrophiles and/or nucleophiles to form new functional groups or substituents. Table IA entitled "Examples of Covalent Linkages and Precursors Thereof" lists selected non-limiting examples of covalent linkages and precursor functional groups which yield the covalent linkages. Table IA may be used as guidance toward the variety of electrophiles and nucleophiles combinations available that provide covalent linkages. Precursor functional groups are shown as electrophilic groups and nucleophilic groups.

TABLE IA

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |

TABLE IA-continued

Examples of Covalent Linkages and Precursors Thereof

| Covalent Linkage Product | Electrophile | Nucleophile |
|---|---|---|
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Alkyl amines | sulfonate esters | amines/anilines |
| hioethers | sulfonate esters | Thiols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

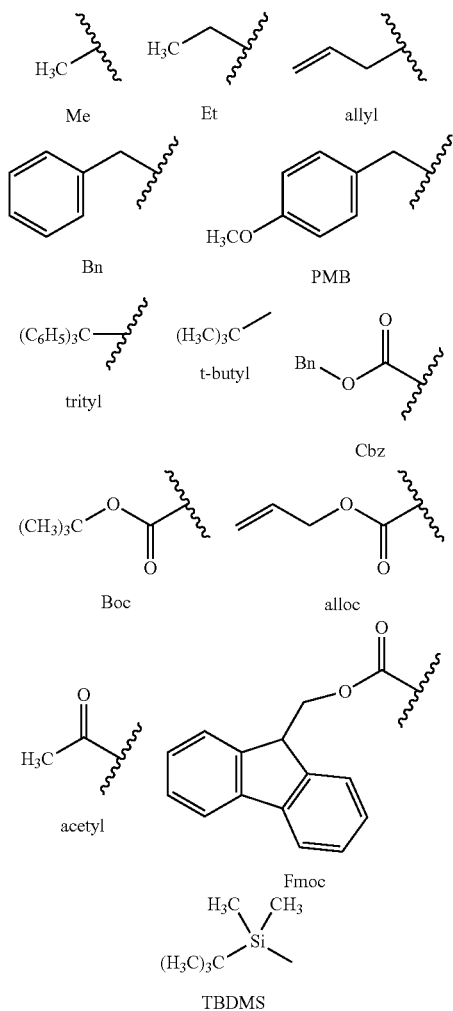

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4$^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic. In some embodiments, "alkyl" is branched or straight-chain alkyl.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which two atoms of the alkyl group form a double bond that is not part of an aromatic group. Non-limiting examples of an alkenyl group include —CH=$CH_2$, —C($CH_3$)=$CH_2$, —CH=$CHCH_3$, —CH=C($CH_3$)$_2$ and —C($CH_3$)=$CHCH_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group). In some embodiments, "alkenyl" is branched or straight-chain alkenyl.

The term "alkynyl" refers to a type of alkyl group in which two atoms of the alkyl group form a triple bond. Non-limiting examples of an alkynyl group include —C≡CH, —C≡$CCH_3$, —C≡$CCH_2CH_3$ and —C≡$CCH_2CH_2CH_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —$NH_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —$CO_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

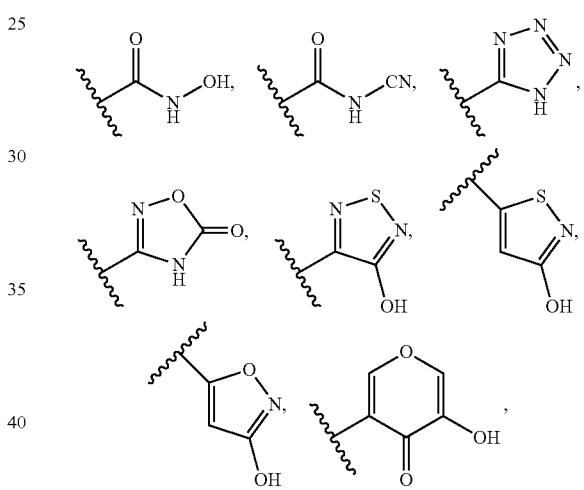

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

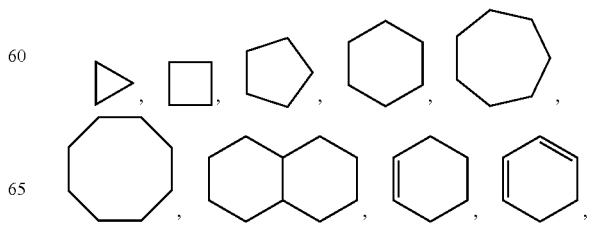

-continued

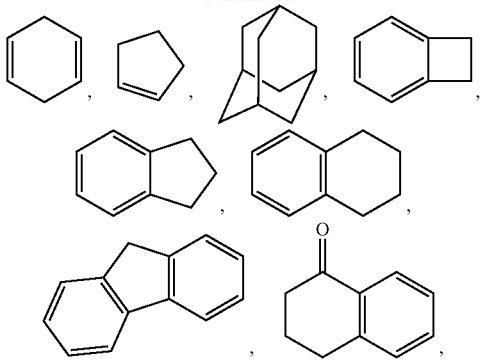

and the like.

The terms "heteroaryl" or, alternatively, "hetero aromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

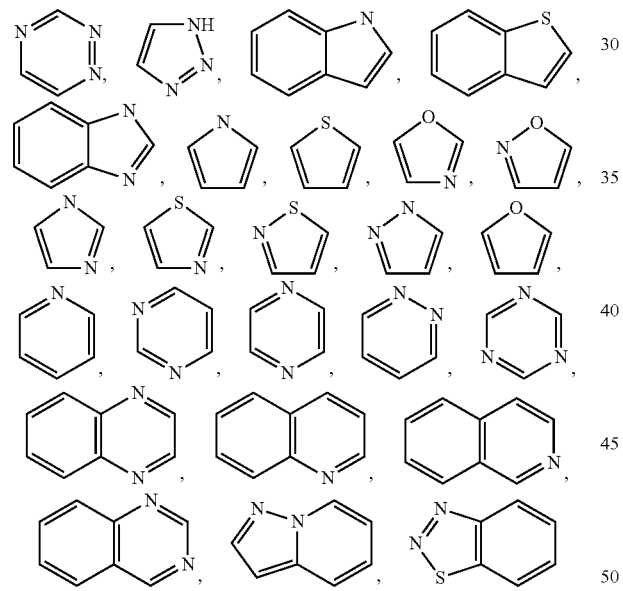

and the like.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. Illustrative examples of heterocycloalkyl groups, also referred to as non-aromatic heterocycles, include:

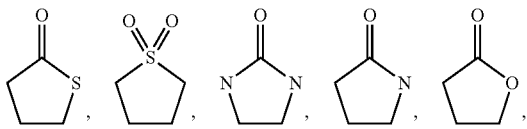

-continued

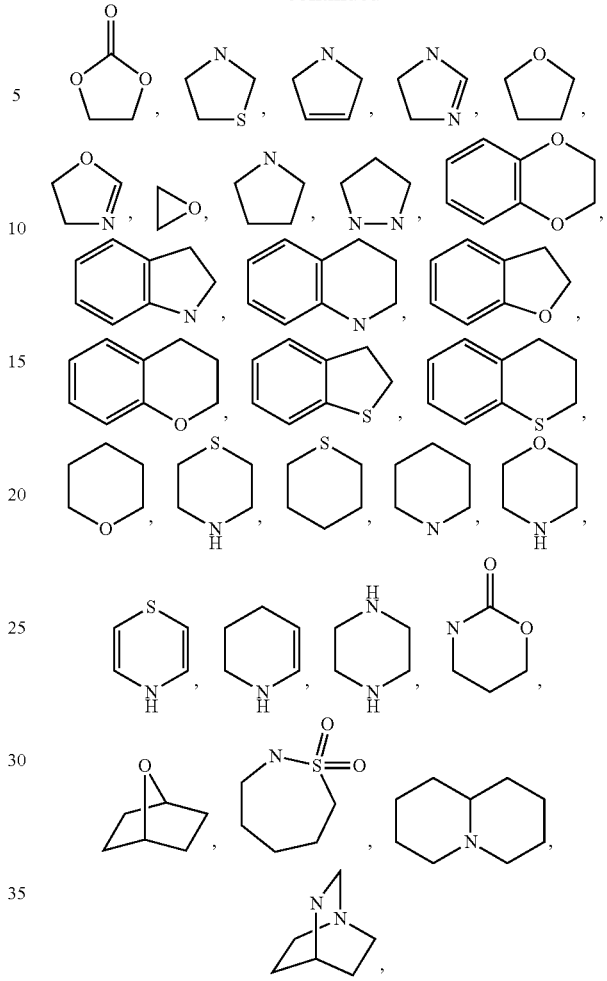

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may be the same or they may be different. Non-limiting examples of haloalkyls include —$CH_2C_1$, —$CF_3$, —$CHF_2$, —$CH_2CF_3$, —$CF_2CF_3$, —$CF(CH_3)_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —$CH_2$—NH—$OCH_3$, —$CH_2$—O—Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2$H, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents may be $La_s$, wherein each LS is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each R$^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

In some embodiments, "optionally substituted" means substituted by 1, 2, 3, or 4 substituents independently selected from halo, cyano, $C_1$-$C_4$ alkyl, $C_2$-$C_4$ alkenyl, hydoxy, $C_1$-$C_4$ alkoxy, $C_1$-$C_4$ haloalkyl, $C_1$-$C_4$ haloalkoxy, amino, $C_1$-$C_4$ alkylamino, and di($C_1$-$C_4$ alkyl)amino.

The methods and formulations described herein include the use of crystalline forms (also known as polymorphs), or pharmaceutically acceptable salts of compounds having the structure of Formulas I, IA, IB, II, IIA, IIB, III, IIIA, IIIB, IV, IVA, and IVB, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Methods of Treatment and Prevention

In one embodiment, provided herein are methods for stimulation of LXR activity in a cell by contacting the cell with an LXR modulator. Examples of such LXR modulators are described above. Other LXR modulators that can be used to stimulate the LXR activity are identified using screening assays that select for such compounds, as described in detail herein.

Prophylactic Methods

In one aspect, provided herein are methods for preventing skin aging in a subject by administering to the subject an LXR modulator. Administration of a prophylactic LXR modulator can occur prior to the manifestation of skin aging symptoms, such that skin aging is prevented or, alternatively, delayed in its progression.

Therapeutic Methods

In another aspect, provided herein are methods of modulating LXR activity for the treatment of skin aging. Accordingly, in an exemplary embodiment, provided herein are methods which involve contacting a cell with an LXR modulator that induces TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, and/or decorin expression and/or inhibits TNFα, MMP1, MMP3, and/or IL-8 expression. These methods are performed in vitro (e.g., by culturing the cell with an LXR modulator) or, alternatively, in vivo (e.g., by administering an LXR modulator to a subject). As such, the present methods are directed to treating a subject affected by skin aging that would benefit from induction of TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, and/or decorin expression and/or inhibition of TNFα, MMP1, MMP3, and/or IL-8 expression.

LXR modulators induce the expression of differential genes in keratinocytes. In human keratinocytes, LXR modulators induce the keratinocyte early differentiation marker involucrin (IVL) as well as late differentiation markers loricrin (LOR), filaggrin (FLG), and transglutaminase 1 (TGM1). The LXR modulator may induce the expression of these genes directly or indirectly.

LXR modulators increase expression of genes involved in fatty acid synthesis and lipid transport in the skin. The LXR ligand induced the expression of genes involved in fatty acid synthesis, namely SREBF1, SREBF2, FASN, and SCD, andgenes involved in cholesterol and phospholipid transport namely APOE, APOD, ABCG1, ABCA1, ABCA12, ABCA2, and ABCA13. LXR modulators increase the expression of LASS4 and SMPD2 in skin.

Pharmaceutical Compositions and Methods of Administration of LXR Modulators

LXR modulators are administered to subjects in a biologically compatible form suitable for topical administration to treat or prevent skin aging. By "biologically compatible form suitable for topical administration" is meant a form of the LXR modulator to be administered in which any toxic effects are outweighed by the therapeutic effects of the modulator. The term "subject" is intended to include living organisms in which an immune response can be elicited, for example, mammals. Administration of LXR modulators as described herein can be in any pharmacological form including a therapeutically effective amount of an LXR modulator alone or in combination with a pharmaceutically acceptable carrier.

The therapeutic or pharmaceutical compositions described herein can be administered by any other suitable route known in the art including, for example, oral, intravenous, subcutaneous, intramuscular, or transdermal, or administration to cells in ex vivo treatment protocols. Administration can be either rapid as by injection or over a period of time as by slow infusion or administration of slow release formulation. For treating or preventing skin aging, administration of the therapeutic or pharmaceutical compositions described herein can be performed, for example, by topical administration.

Topical administration of an LXR modulator may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin. The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

A therapeutically effective amount of an LXR modulator may vary according to factors such as the skin aging state, age, sex, and weight of the individual, and the ability of the LXR modulator to elicit a desired response in the individual. Dosage regime may be adjusted to provide the optimum cosmetic, response. For example, several divided doses may be administered daily, or the dose may be proportionally reduced as indicated by the exigencies of the skin aging.

LXR modulators can also be linked or conjugated with agents that provide desirable pharmaceutical or pharmacodynamic properties. For example, LXR modulators can be stably linked to a polymer such as polyethylene glycol to obtain desirable properties of solubility, stability, half-life, and other pharmaceutically advantageous properties (see, e.g., Davis et al., Enzyme Eng. 4:169-73 (1978); Burnham N L, Am. J. Hosp. Pharm. 51:210-18 (1994)).

LXR modulators can be in a composition which aids in delivery into the cytosol of a cell. For example, an LXR modulator may be conjugated with a carrier moiety such as a liposome that is capable of delivering the modulator into the cytosol of a cell. Such methods are well known in the art (see, e.g., Amselem S et al., Chem. Phys. Lipids 64:219-37 (1993)).

LXR modulators can be employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the LXR modulator, use thereof in the cosmetic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

In one embodiment, the anti-skin aging compositions disclosed herein can further comprise a retinoic acid receptor (RAR) ligand. Useful RAR ligands include, for example, all-trans retinoic acid (tretinoin) and/or synthetic retinoic acid receptor ligands. Tretinoin is sold under such trademarks as Atragen®, Avita®, Renova®, Retin-A®, Vesanoid®, and Vitinoin®. Exemplary synthetic retinoic acid receptor ligands include tazarotene (Avage®; ethyl 6-[2-(4,4-dimethylthiochroman-6-yl)ethynyl]pyridine-3-carboxylate) and Differin® (adapalene; 6-[3-(1-adamantyl)-4-methoxyphenyl]-2-naphthoic acid; CD271).

Topical compositions can be prepared by combining the anti-skin aging composition with conventional pharmaceutically acceptable diluents and carriers commonly used in topical dry, liquid, cream, and aerosol formulations. Ointment and creams can, for example, be formulated with an aqueous or oily base with the addition of suitable thickening and/or gelling agents. An exemplary base is water. Thickening agents which can be used according to the nature of the base include aluminum stearate, cetostearyl alcohol, propylene glycol, polyethylene glycols, hydrogenated lanolin, and the like. Lotions can be formulated with an aqueous base and will, in general, also include one or more of the following: stabilizing agents, emulsifying agents, dispersing agents, suspending agents, thickening agents, coloring agents, perfumes, and the like. Powders can be formed with the aid of any suitable powder base, for example, talc, lactose, starch, and the like. Drops can be formulated with an aqueous base or non-aqueous base, and can also include one or more dispersing agents, suspending agents, solubilizing agents, and the like.

In one embodiment, the topical composition may, for example, take the form of hydrogel based on polyacrylic acid or polyacrylamide; as an ointment, for example with polyethyleneglycol (PEG) as the carrier, like the standard ointment DAB 8 (50% PEG 300, 50% PEG 1500); or as an emulsion, especially a microemulsion based on water-in-oil or oil-in-water, optionally with added liposomes. Suitable permeation accelerators (entraining agents) include sulphoxide derivatives such as dimethylsulphoxide (DMSO) or decylmethylsulphoxide (decyl-MSO) and transcutol (diethyleneglycolmonoethylether) or cyclodextrin; as well as pyrrolidones, for example 2-pyrrolidone, N-methyl-2-pyrrolidone, 2-pyrrolidone-5-carboxylic acid, or the biodegradable N-(2-hydroxyethyl)-2-pyrrolidone and the fatty acid esters thereof; urea derivatives such as dodecylurea, 1,3-didodecylurea, and 1,3-diphenylurea; terpenes, for example D-limonene, menthone, a-terpinol, carvol, limonene oxide, or 1,8-cineol.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

The carrier can also contain other pharmaceutically-acceptable excipients for modifying or maintaining the pH, osmolarity, viscosity, clarity, color, sterility, stability, rate of dissolution, or odor of the formulation. The anti-skin aging compositions can also further comprise antioxidants, sun screens, natural retinoids (e.g., retinol), and other additives commonly found in skin treatment compositions.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the LXR modulator and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the LXR modulator activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such LXR modulators can be determined by standard pharmaceutical procedures in cell cultures or experimental animals, for example, for determining the $LD_{50}$ (the dose lethal to 50% of the population) and the ED so (the dose therapeutically effective in 50% of the population). The dose ratio between toxic and therapeutic effects is the therapeutic index and it can be expressed as the ratio $LD_{50}/ED_{50}$. LXR modulators that exhibit large therapeutic indices are preferred. While LXR modulators that exhibit toxic side effects may be used, care should be taken to design a delivery system that targets such modulators to the site of affected tissue in order to minimize potential damage to uninfected cells and, thereby, reduce side effects.

The data obtained from the cell culture assays and animal studies can be used in formulating a range of dosage for use in humans. The dosage of such LXR modulators lies preferably within a range of circulating concentrations that include the $ED_{50}$ with little or no toxicity. The dosage may vary within this range depending upon the dosage form employed and the route of administration utilized. For any LXR modulator used in a method described herein, the therapeutically effective dose can be estimated initially from cell culture assays. A dose may be formulated in animal models to achieve a circulating plasma concentration range that includes the $IC_{50}$ (i.e., the concentration of LXR modulator that achieves a half-maximal inhibition of symptoms) as determined in cell culture. Such information can be used to more accurately determine useful doses in humans. Levels in plasma may be measured, for example, by high performance liquid chromatography.

Monitoring the influence of LXR modulators on the induction of TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, and/or decorin expression and/or inhibition of TNFα, MMP1, MMP3, and/or IL-8 expression is applied in clinical trials. For example, the effectiveness of an LXR modulator is monitored in clinical trials of subjects exhibiting increased TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, and/or decorin expression and/or decreased TNFα, MMP1, MMP3, and/or IL-8 expression. In such clinical trials, the expression of TIMP1, ASAH1, SPTLC1, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 is used as a "read out" or markers of the different skin aging phenotypes.

Thus, to study the effect of LXR modulators on skin aging, for example, in a clinical trial, cells are isolated and RNA prepared and analyzed for the levels of expression of TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8. The levels of gene expression (i.e., a gene expression pattern) is quantified, for example, by Northern blot analysis or RT-PCR, by measuring the amount of protein produced, or by measuring the levels of activity of TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8, all by methods well known to those of ordinary skill in the art. In this way, the gene expression pattern serves as a marker, indicative of the physiological response of the cells to the LXR modulator. Accordingly, this response state is determined before, and at various points during, treatment of the individual with the LXR modulator.

Also provided is a method for monitoring the effectiveness of treatment of a subject with an LXR modulator comprising the steps of (i) obtaining a pre-administration sample from a subject prior to administration of the LXR modulator; (ii) detecting the level of expression of TIMP1, ASAH1, $SPTLC_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8; (iii) obtaining one or more post-administration samples from the subject; (iv) detecting the level of expression of TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 in the post-administration samples; (v) comparing the level of expression of TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 in the pre-administration sample with the TIMP1, ABCA12, decorin, TNFα, MMP1, MMP3, and/or IL-8 expression in the post administration sample or samples; and (vi) altering the administration of the LXR modulator to the subject accordingly.

For example, increased administration of the LXR modulator may be desirable to increase TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, and/or decorin expression to higher levels than detected and/or reduce TNFα, MMP1, MMP3, and/or IL-8 expression to lower levels than detected, that is, to increase the effectiveness of the LXR modulator. Alternatively, decreased administration of the LXR modulator may be desirable to decrease TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, and/or decorin expression to lower levels than detected or activity and/or to increase TNFα, MMP1, MMP3, and/or IL-8 expression to higher levels than detected, that is, to decrease the effectiveness of the LXR modulator. According to such an embodiment, TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 expression may be used as an indicator of the effectiveness of an LXR modulator, even in the absence of an observable phenotypic response.

Furthermore, in the treatment of skin aging, compositions containing LXR modulators are administered exogenously, and it is desirable to achieve certain target levels of LXR modulator in sera, in any desired tissue compartment, and/or in the affected tissue. It is, therefore, advantageous to be able to monitor the levels of LXR modulator in a patient or in a biological sample including a tissue biopsy sample obtained from a patient and, in some cases, also monitoring the levels of TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 expression. Accordingly, also provided herein are methods for detecting the presence of LXR modulator in a sample from a patient using techniques described herein.

Screening Assays

In one embodiment, expression levels of cytokines and metalloproteases described herein are used to facilitate design and/or identification of compounds that treat skin aging through an LXR-based mechanism. Accordingly provided herein are methods (also referred to herein as "screening assays") for identifying modulators, i.e., LXR modulators, that have a stimulatory or inhibitory effect on, for example, TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 expression. Compounds thus identified are used as anti-skin aging compounds as described elsewhere herein.

An exemplary screening assay is a cell-based assay in which a cell that expresses LXR is contacted with a test compound, and the ability of the test compound to modulate TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 expression through an LXR-based mechanism. Determining the ability of the test compound to modulate TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8 expression is accomplished by monitoring, for example, DNA, mRNA, or protein levels, or by measuring the levels of activity of TIMP1, ASAH1, SPTLC$_1$, SMPD1, LASS2, TXNRD1, GPX3, GSR, CAT, ApoE, ABCA1, ABCA2, ABCA12, ABCA13, ABCG1, αSyn, decorin, TNFα, MMP1, MMP3, and/or IL-8. The cell, for example, is of mammalian origin, e.g., human.

Novel modulators identified by the above-described screening assays are used for treatments as described herein.

EXAMPLES

The following examples are offered for purposes of illustration, and are not intended to limit the scope of the claims provided herein. All literature citations in these examples and throughout this specification are incorporated herein by references for all legal purposes to be served thereby.

Examples 1 and 2: Synthesis of Ethyl 2-(1-(3'-(methylsulfonyl)-[1,1'-biphenyl]-4-yl)-4-(trifluoromethyl)-1H-imidazol-2-yl)acetate (Example 1) and 2-(1-(3'-(Methylsulfonyl)-[1,1'-biphenyl]-4-yl)-4-(trifluoromethyl)-1H-imidazol-2-yl)acetic acid (Example 2)

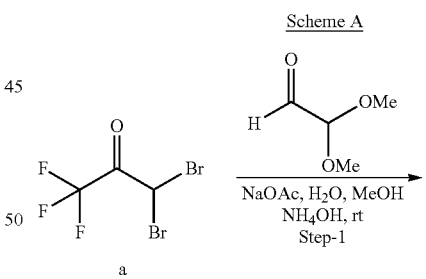

a

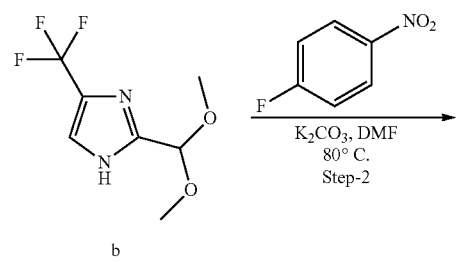

b

-continued

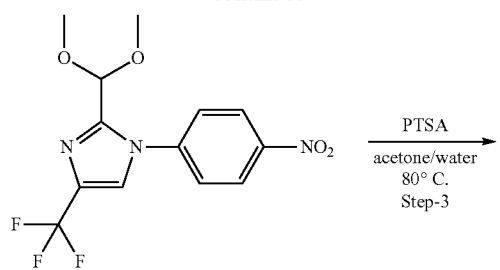

c

PTSA
acetone/water
80° C.
Step-3

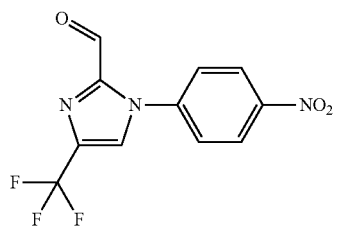

d

NaBH₄
MeOH, rt
Step-4

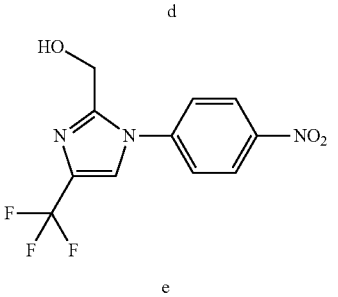

e

CBr₄, PPh₃
DCM, rt
Step-5

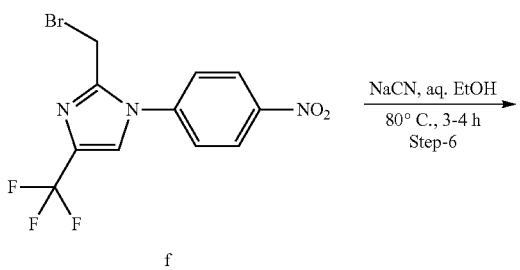

f

NaCN, aq. EtOH
80° C., 3-4 h
Step-6

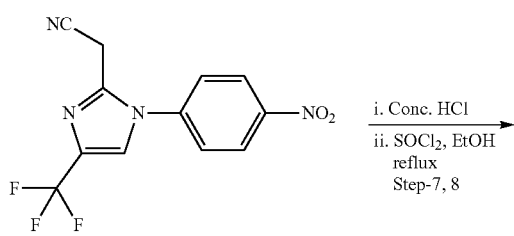

g i. Conc. HCl
ii. SOCl₂, EtOH
reflux
Step-7, 8

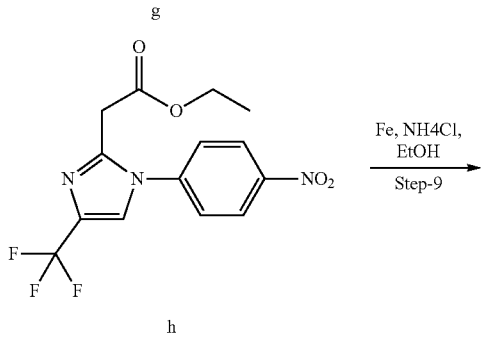

h

Fe, NH₄Cl,
EtOH
Step-9

-continued

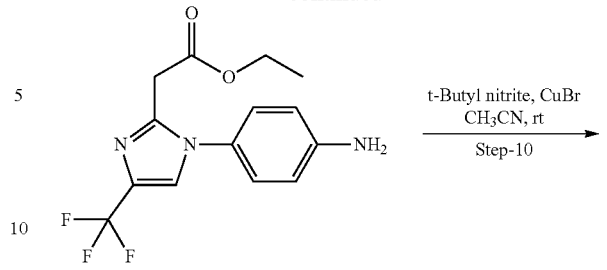

i t-Butyl nitrite, CuBr
CH₃CN, rt
Step-10

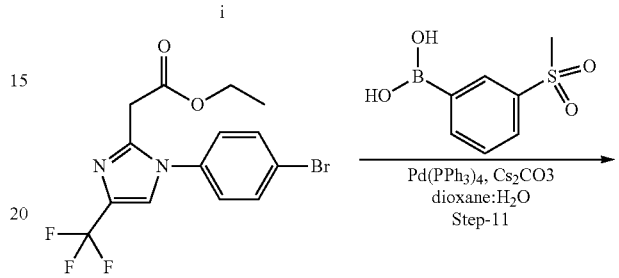

j

Pd(PPh₃)₄, Cs₂CO₃
dioxane:H₂O
Step-11

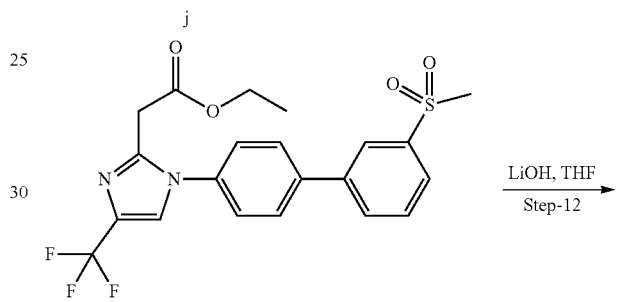

(1)

LiOH, THF
Step-12

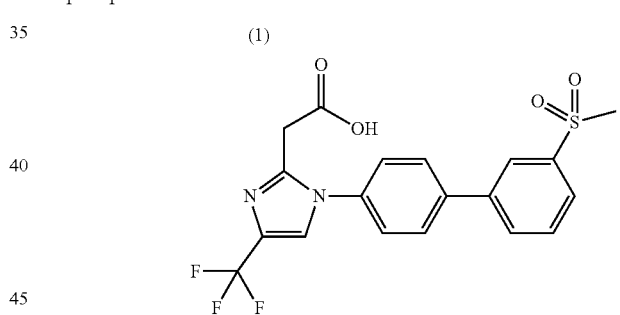

(2)

Step 1: 2-(Dimethoxymethyl)-4-(trifluoromethyl)-1H-imidazole (b)

Following Scheme A, to a stirred solution of compound a (10 g, 37.31 mmol) in water (50 mL), was added sodium acetate (6.12 g, 74.62 mmol), and the solution was stirred at 100° C. for 40 min. To this solution, 2,2-dimethoxyacetaldehyde (4.26 g, 41.04 mmol) in MeOH (20 mL) and NH₄OH (10 mL) were added at rt and the resulting reaction mixture was stirred at rt for 12 h. The progress of the reaction was monitored by TLC. Upon completion the reaction mixture was diluted with water and extracted with ethyl acetate. The combined organic layers were dried over anhydrous Na₂SO₄ and concentrated under reduced pressure resulting in a crude compound which was purified by column chromatography to afford the compound b (7 g, 89.7%).

Step 2: 2-(Dimethoxymethyl)-1-(4-nitrophenyl)-4-(trifluoromethyl)-1H-imidazole (c)

To a stirred solution of compound b (7 g, 33.33 mmol) and 1-fluoro-4-nitrobenzene (5.17 g, 36.66 mmol) in DMF (70 mL), was added $K_2CO_3$ (9.19 g, 66.66 mmol), and the resulting reaction mixture was stirred at 80° C. for 12 h. The progress of the reaction was monitored by TLC and LCMS. Upon completion the reaction mixture was diluted with water and extracted with ethyl acetate. The combined organic layers were dried over anhydrous $Na_2SO_4$ and concentrated under reduced pressure resulting in a crude compound which was purified by column chromatography to afford the compound c (7 g, 67.3%).

Step 3: 1-(4-Nitrophenyl)-4-(trifluoromethyl)-1H-imidazole-2-carbaldehyde (d)

To a stirred solution of compound c (4 g, 12.08 mmol) in acetone:water (40 mL: 5 mL) mixture, PTSA (1.15 g, 6.04 mmol) was added and the resulting reaction mixture was stirred at 80° C. for 4 h. The progress of the reaction was monitored by TLC and LCMS. Upon completion the reaction mixture was diluted with water and extracted with ethyl acetate. The combined organic layers were dried over anhydrous $Na_2SO_4$ and concentrated under reduced pressure resulting in a crude compound which was purified by column chromatography to afford the compound d (3 g, 87.2%).

Step 4: (1-(4-Nitrophenyl)-4-(trifluoromethyl)-1H-imidazol-2-yl) methanol (e)

To a stirred solution of compound d (3 g, 10.53 mmol) in MeOH (30 mL) at 0° C., $NaBH_4$ (0.8 g, 21.05 mmol) was added and the resulting reaction mixture was stirred at rt for 1 h. The progress of the reaction was monitored by TLC. Upon completion the reaction mixture was concentrated to dryness under reduced pressure. The residue obtained was diluted with water and extracted with ethyl acetate. The combined organic layers were dried over anhydrous $Na_2SO_4$ and concentrated under reduced pressure to afford the compound e (2.8 g, crude) which was used in the subsequent step without further purification.

Step 5: 2-(Bromomethyl)-1-(4-nitrophenyl)-4-(trifluoromethyl)-1H-imidazole (f)

To a stirred solution of compound e (2.8 g, 9.76 mmol) in DCM (30 mL) at 0° C., $CBr_4$ (4.84 g, 14.63 mmol) and $PPh_3$ (3.81 g, 14.63 mmol) were added and the resulting reaction mixture was stirred at rt for 12 h. The progress of the reaction was monitored by TLC. Upon completion the reaction mixture was diluted with water and extracted with DCM. The combined organic layers were dried over anhydrous $Na_2SO_4$ and concentrated under reduced pressure resulting in a crude compound which was purified by column chromatography to afford the compound f (2.5 g, 75.7%).

Step 6: 2-(1-(4-Nitrophenyl)-4-(trifluoromethyl)-1H-imidazol-2-yl) acetonitrile (g)

To a stirred solution of compound f (2.5 g, 7.16 mmol) in EtOH: $H_2O$ (20 mL:2.5 mL) at 0° C., NaCN (0.526 g, 10.75 mmol) was added and the resulting reaction mixture was stirred at 80° C. for 4 h. The progress of the reaction was monitored by TLC and LCMS. Upon completion the reaction mixture was concentrated to dryness under reduced pressure. The residue obtained was diluted with water and extracted with ethyl acetate. The combined organic layers were dried over anhydrous $Na_2SO_4$ and concentrated under reduced pressure resulting in a crude compound which was purified by column chromatography to afford the compound g (2 g, 87%).

Steps 7 and 8: Ethyl 2-(1-(4-nitrophenyl)-4-(trifluoromethyl)-1H-imidazol-2-yl) acetate (h)

A mixture of compound h (2 g, 6.75 mmol) and Conc HCl (5 mL) was heated at 80° C. for 3 h. The progress of the reaction was monitored by TLC. Upon completion the reaction mixture was concentrated to dryness under reduced pressure giving respective acid (2 g) which was used in the subsequent step without further purification.

To a stirred solution of above acid (2 g, 6.35 mmol) in EtOH (10 mL) at 0° C., $SOC_{12}$ (1.51 g, 12.69 mmol) was added. The reaction mixture was stirred at at 80° C. for 1 h. The progress of the reaction was monitored by TLC. Upon completion the reaction mixture was concentrated under reduced pressure. The residue obtained was basified with aqueous $NaHCO_3$ solution and extracted with ethyl acetate. The combined organic layers were dried over anhydrous $Na_2SO_4$ and concentrated under reduced pressure to afford the compound h (1.7 g, 81%) which was used in the subsequent step without further purification.

Step 9: Ethyl 2-(1-(4-aminophenyl)-4-(trifluoromethyl)-1H-imidazol-2-yl) acetate (i)

To stirred solution of compound h (0.5 g, 1.45 mmol) in ethanol (5 mL), ammonium chloride (0.5 g, 9.25 mmol) dissolved in water (5 mL) and iron powder (0.641 g, 11.66 mmol) were added under stirring. The resulting reaction mixture was stirred at 80° C. for 2 h. The progress of the reaction was monitored by TLC. Upon completion the reaction mixture was filtered and the residue washed well with hot ethanol. The filtrate was concentrated under reduced pressure. The residue obtained was basified with aqueous $NaHCO_3$ solution and extracted with ethyl acetate. The combined organic layers were dried over anhydrous $Na_2SO_4$ and concentrated under reduced pressure to afford the compound i (0.4 g, 88%) which was used in the subsequent step without further purification.

Step 10: Ethyl 2-(1-(4-bromophenyl)-4-(trifluoromethyl)-1H-imidazol-2-yl) acetate 0

To a stirred solution tert-butyl nitrile (0.173 g, 1.67 mmol) in ACN (2 mL) at 0° C., copper bromide (0.3 g, 1.34 mmol) was added and the solution was stirred at same temperature for 1 h. To this solution, compound i (0.35 g, 1.11 mmol) was added and the reaction mixture was stirred at 0° C. for 1 h. The progress of the reaction was monitored by TLC. Upon completion the reaction mixture was diluted with water and extracted with ethyl acetate. The combined organic layers were dried over anhydrous $Na_2SO_4$ and concentrated under reduced pressure resulting in a crude compound which was purified by column chromatography to afford the compound j (0.2 g, 48%).

Step 11: Ethyl 2-(1-(3'-(methylsulfonyl)-[1,1'-biphenyl]-4-yl)-4-(trifluoromethyl)-1H-imidazol-2-yl) acetate (Example 1)

To a stirred solution of compound j (0.2 g, 0.531 mmol) and (3-(methylsulfonyl)phenyl)boronic acid (0.111 g, 0.55 mmol) in dioxane/water mixture (4 mL+1 mL), Na₂CO₃ (0.14 g, 1.33 mmol) was added and the solution was purged with argon for 10 min. Then Pd (PPh₃)₄ (0.061 g, 0.053 mmol) was added and argon was purged again for 10 min. The reaction mass was heated at 80° C. for 3 h. The progress of the reaction was monitored by TLC. Upon completion the reaction mixture diluted with water and extracted with ethyl acetate. The combined organic layers were dried over Na₂SO₄ and concentrated under reduced pressure. The crude compound was purified by column chromatography to afford the desired compound Example 1 (0.15 g, 63%). LCMS: 453.10 (M+1)⁺; HPLC: 98.11% (@ 210 nm-400 nm) (Rt; 8.687; Method: YMC TRIART C-18 (150 mm×4.6 mm×3µ); ID:E-AC-2/13/COL/03, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, CDCl₃) δ 8.18 (t, J=1.8 Hz, 1H), 7.99 (dt, J=7.9, 1.4 Hz, 1H), 7.89 (dt, J=7.8, 1.5 Hz, 1H), 7.79-7.66 (m, 3H), 7.54-7.45 (m, 2H), 7.45-7.40 (m, 1H), 4.11 (q, J=7.1 Hz, 2H), 3.80 (s, 2H), 3.11 (s, 3H), 1.20 (t, J=7.1 Hz, 3H).

Step 12: 2-(1-(3'-(Methylsulfonyl)[1,1'-biphenyl]-4-yl)-4-(trifluoromethyl)-1H-imidazol-2-yl)acetic acid (Example 2)

To a stirred solution of Example 1 (0.1 g, 0.221 mmol) in THF (5 mL), LiOH (0.01 g, 0.442 mmol in 1 mL H₂O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with ethyl acetate. The combined organic layers were dried over Na₂SO₄ and concentrated under reduced pressure. The crude compound was purified by acetonitrile and diethyl ether washings give the desired compound Example 2 (0.06 g, 64%). LCMS: 425.10 (M+1)⁺; HPLC: 99.08% (@ 210 nm-400 nm) (Rt; 7.000; Method: YMC ODS-A (150 mm×4.6 mm×3µ); ID:E-AC-2/13/COL/01, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 8.23 (t, J=1.9 Hz, 1H), 8.15-8.06 (m, 2H), 8.00-7.92 (m, 3H), 7.82-7.67 (m, 3H), 3.70 (s, 2H), 3.32 (s, 3H).

Examples 3 and 4: Synthesis of Ethyl 2-(1-(4'-(hydroxymethyl)-3'-(methylsulfonyl)-[1,1'-biphenyl]-4-yl)-4-(trifluoromethyl)-1H-imidazol-2-yl)acetate (Example 3) and 2-(1-(4'-(Hydroxymethyl)-3'-(methylsulfonyl)[1,1'-biphenyl]-4-yl)-4-(trifluoromethyl)-1H-imidazol-2-yl)acetic acid (Example 4)

Examples 3 and 4 were made by a process similar to that in Scheme A, except forming the boronate E by the process shown in the scheme below

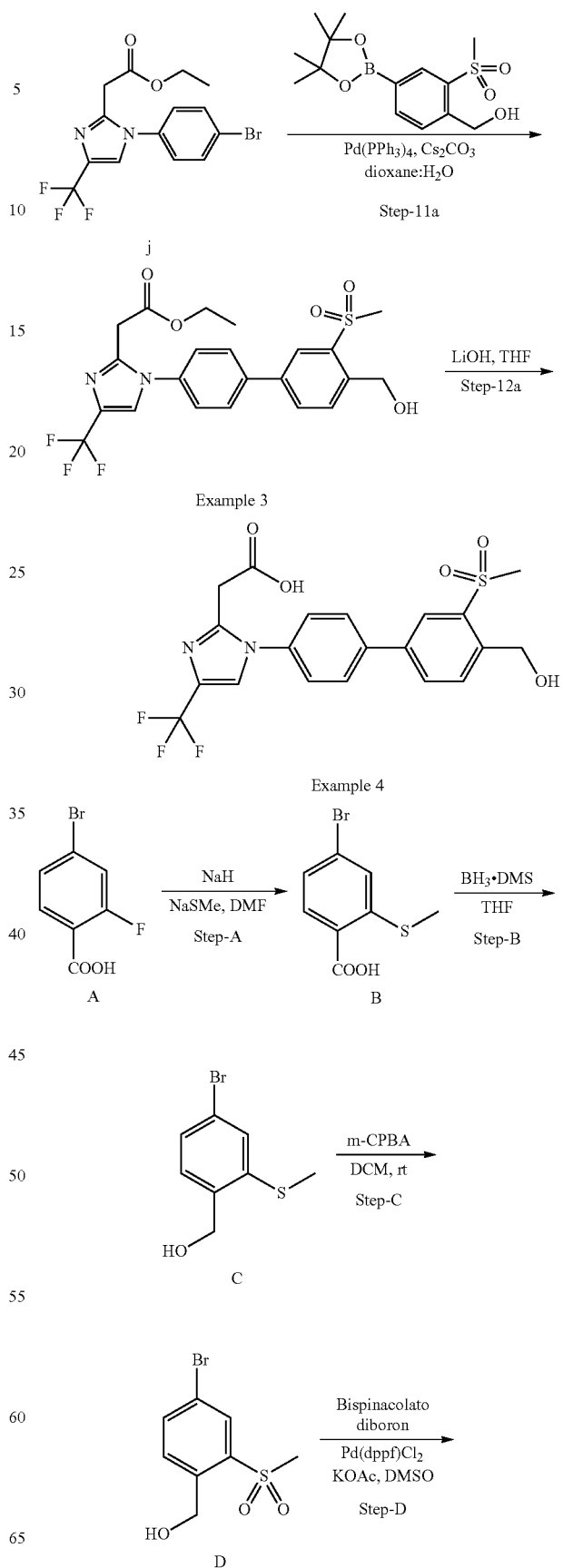

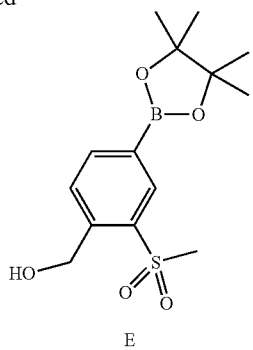

E

Synthesis of 4-Bromo-2-(methylthio) benzoic acid (B)

To a stirred solution of compound A (10 g, 45.66 mmol) in dry DMF (100 mL) at 0° C., NaH (60%, 2.74 g, 68.49 mmol) was added and the solution was stirred at 0° C. for 1 h. To this solution, sodium thiomethoxide (7.04 g, 100.4 mmol) was added at 0° C. and the resulting reaction mixture was stirred at rt for 16 h. The progress of the reaction was monitored by TLC and LCMS. Upon completion the reaction mixture was acidified with 1N HCl. The precipitated solid was collected by filtration and dried under reduced pressure to afford the title compound B (11 g, 98%)

Synthesis of (4-Bromo-2-(methylthio) phenyl) methanol (C)

To a stirred solution of compound B (5 g, 20.24 mmol) in dry THF (50 mL) at 0° C., BH$_3$-DMS (2 M, 20.2 mL, 40.48 mmol) was added and the reaction mixture was stirred at 80° C. for 6 h. The progress of the reaction was monitored by TLC. Upon completion the reaction mixture quenched with methanol and concentrated to dryness under reduced pressure. The residue obtained was diluted with water and extracted with ethyl acetate. The combined organic layers were dried over Na$_2$SO$_4$ and concentrated under reduced pressure to afford the compound C (5 g, crude) which was used in the subsequent step without further purification.

Synthesis of (4-Bromo-2-(methylsulfonyl) phenyl) methanol (D)

To a stirred solution of compound C (5 g, 21.45 mmol) in DCM (50 mL) at 0° C., m-CPBA (7.38 g, 42.90 mmol) was added and the resulting reaction mixture was stirred at rt for 16 h. The progress of the reaction was monitored by TLC. Upon completion the reaction mixture diluted with aqueous sat. NaHCO$_3$ solution and extracted with ethyl acetate. The combined organic layers were dried over Na$_2$SO$_4$ and concentrated under reduced pressure resulting in a crude compound which was purified by column chromatography to afford the compound D (5.6 g, 98%).

Synthesis of (2-(Methylsulfonyl)-4-(4,4,5,5-tetramethyl-1,3,2-dioxaborolan-2-yl)phenyl)methanol (E)

To a stirred solution of compound D (6 g, 22.64 mmol) and bis pinacolacto diborone (6.9 g, 27.16 mmol) in DMSO (60 mL), potassium acetate (5.55 g, 56.60 mmol) was added and the solution was purged with argon for 15 min. Then Pd(dppf)C$_{12}$:DCM (1.84 g, 2.26 mmol) was added and argon was purged again for 15 min. The reaction mass was heated at 90° C. for 16 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the desired compound E (4 g, 56.3%).

Step 11a: Ethyl 2-(1-(4'-(hydroxymethyl)-3'-(methylsulfonyl)-[1,1'-biphenyl]-4-yl)-4-(trifluoromethyl)-1H-imidazol-2-yl)acetate (Example 3)

To a stirred solution of compound j from step 10 of Example 1 (0.3 g, 0.797 mmol) and (2-(methylsulfonyl)-4-(4,4,5,5-tetramethyl-1,3,2-dioxaborolan-2-yl)phenyl)methanol (0.375 g, 1.19 mmol) in dioxane/water mixture (4 mL+1 mL), Na$_2$CO$_3$ (0.211 g, 1.99 mmol) was added and the solution was purged with argon for 10 min. Then Pd(PPh$_3$)$_4$ (0.092 g, 0.079 mmol) was added and argon was purged again for 10 min. The reaction mass was heated at 80° C. for 12 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the desired compound Example 3 (0.02 g, 6%). LCMS: 483.25 (M+1)$^+$; HPLC: 97.40% (@ 210 nm-400 nm) (Rt; 7.996; Method: YMC TRIART C-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 8.19-8.07 (m, 2H), 7.96-7.87 (m, 3H), 7.69-7.50 (m, 3H), 5.56 (t, J=5.5 Hz, 1H), 4.97 (d, J=5.5 Hz, 2H), 4.00-3.90 (m, 4H), 3.32 (d, J=12.7 Hz, 3H), 1.02 (t, J=7.1 Hz, 3H).

Step 12a: 2-(1-(4'-(Hydroxymethyl)-3'-(methylsulfonyl)[1,1'-biphenyl]-4-yl)-4-(trifluoromethyl)-1H-imidazol-2-yl)acetic acid (Example 4)

To a stirred solution of Example 3 (0.04 g, 0.082 mmol) in THF (2 mL), LiOH (0.004 g, 0.165 mmol in 0.5 mL H$_2$O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with ethyl acetate. The combined organic layers were dried over Na$_2$SO$_4$ and concentrated under reduced pressure resulting in a crude compound which was purified by acetonitrile and diethyl ether washings to afford the desired compound Example 4 (0.015 g, 41%). LCMS: 455.25 (M+1)$^+$; HPLC: 94.14% (@ 210 nm-400 nm) (Rt; 6.459; Method: YMC ODS (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 12.76 (s, 1H), 8.19-8.07 (m, 3H), 7.91 (dd, J=9.7, 8.1 Hz, 3H), 7.72-7.51 (m, 2H), 5.56 (s, 1H), 4.97 (s, 2H), 3.82 (s, 2H), 3.34 (s, 3H).

Examples 5 and 6: Synthesis of Ethyl 1-isobutyl-5-(3'-(methylsulfonyl)-[1,1'-biphenyl]-4-yl)-1H-pyrazole-3-carboxylate (Example 5) and 1-Isobutyl-5-(3'-(methylsulfonyl)-[1,1'-biphenyl]-4-yl)-1H-pyrazole-3-carboxylic acid (Example 6)

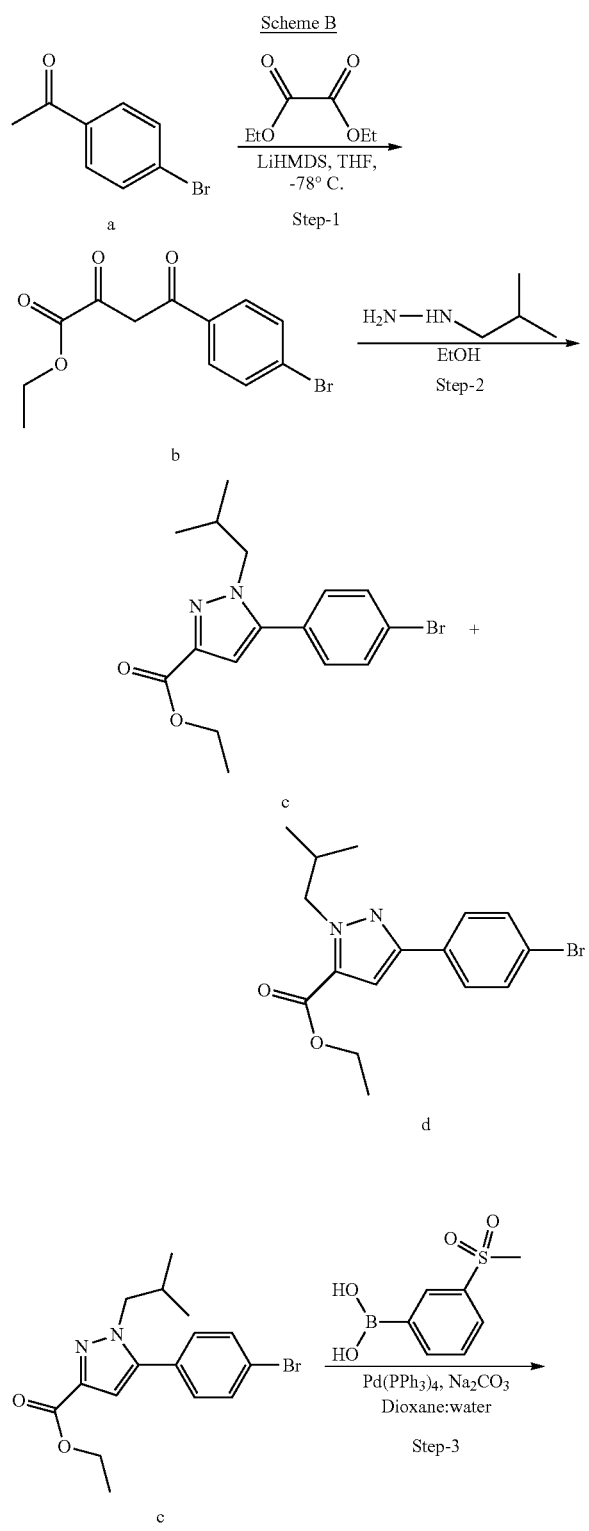

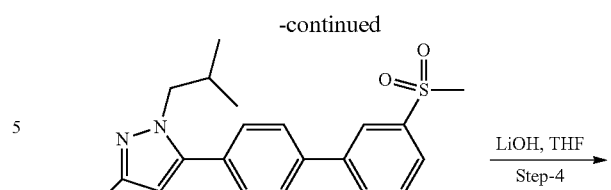

Example 5

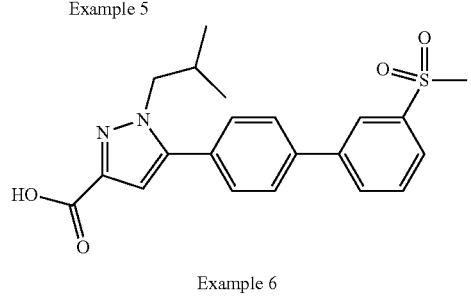

Example 6

Step 1: Ethyl 4-(4-bromophenyl)-2,4-dioxobutanoate (b)

Following Scheme B, to a stirred solution of 1-(4-bromophenyl)ethanone (5 g, 25.38 mmol) in dry THF (50 mL) at −78° C., LiHMDS (1 M, 28 mL, 27.91 mmol) was added and the solution was stirred at same temperature for 1 h. To this solution, diethyl oxalate (4.08 g, 27.91 mmol) in THF (10 mL) was added at −78° C. and the resulting reaction mixture was stirred at rt for 12 h. The progress of the reaction was monitored by TLC and LCMS. Upon completion the reaction mixture was quenched with aqueous sat. $NH_4Cl$ solution and extracted with ethyl acetate. The combined organic layers were dried over anhydrous $Na_2SO_4$ and concentrated under reduced pressure resulting in a crude compound which was purified by column chromatography to afford the compound b (2.5 g, 33.3%).

Step 2: Ethyl 5-(4-bromophenyl)-1-isobutyl-1H-pyrazole-3-carboxylate (c)

To a stirred solution of compound b (1 g, 3.35 mmol) in EtOH (20 mL), isobutyl hydrazine hydrochloride (0.45 g, 3.69 mmol) was added and the resulting reaction mixture was stirred at 80° C. for 3 h. The progress of the reaction was monitored by TLC. Upon completion the reaction mixture was concentrated to dryness under reduced pressure. The residue obtained was diluted with water and extracted with ethyl acetate. The combined organic layers were dried over anhydrous $Na_2SO_4$ and concentrated under reduced pressure to afford a crude compound which was purified by column chromatography to afford the compound c (0.7 g, 60%) which was confirmed by NOE experiment.

Step 3: Ethyl 1-isobutyl-5-(3'-(methylsulfonyl)[1,1'-biphenyl]-4-yl)-1H-pyrazole-3-carboxylate (Example 5)

To a stirred solution of compound c (0.7 g, 2.0 mmol) and (3-(methylsulfonyl)phenyl)boronic acid (0.42 g, 2.10 mmol) in dioxane/water mixture (8 mL+2 mL), $Na_2CO_3$ (0.530 g, 5.0 mmol) was added and the solution was purged with argon for 10 min. Then Pd (PPh₃)₄ (0.231 g, 0.2 mmol) was added and argon was purged again for 10 min. The reaction mass was heated at 80° C. for 6 h. The progress of the reaction was monitored by TLC. Upon completion the reaction mixture diluted with water and extracted with ethyl acetate. The combined organic layers were dried over Na₂SO₄ and concentrated under reduced pressure. The crude compound was purified by column chromatography to afford the desired compound Example 5 (0.5 g, 59%). LCMS: 427.15 (M+1)⁺; HPLC: 99.83% (@ 210 nm-400 nm) (Rt; 9.552; Method: YMC TRIARTC-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 8.24 (d, J=2.2 Hz, 1H), 8.13 (d, J=7.7 Hz, 1H), 7.94 (t, J=7.6 Hz, 3H), 7.78 (t, J=7.8 Hz, 1H), 7.67 (d, J=7.9 Hz, 2H), 6.91 (d, J=1.9 Hz, 1H), 4.30 (q, J=7.0 Hz, 2H), 4.09 (d, J=7.4 Hz, 2H), 3.33 (s, 3H), 2.05 (tq, J=12.4, 7.0 Hz, 1H), 1.31 (t, J=7.1 Hz, 3H), 0.72 (d, J=6.6 Hz, 6H).

Step 4: 1-Isobutyl-5-(3'-(methylsulfonyl)[1,1'-biphenyl]-4-yl)-1H-pyrazole-3-carboxylic acid (Example 6)

To a stirred solution of Example 5 (0.5 g, 1.17 mmol) in THF (5 mL), LiOH (0.056 g, 2.34 mmol in 2 mL H₂O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with 10% MeOH/DCM. The combined organic layers were dried over Na₂SO₄ and concentrated under reduced pressure. The crude compound was purified by acetonitrile and diethyl ether washings to afford the desired compound Example 6 (0.35 g, 75%). LCMS: 399.25 (M+1)⁺; HPLC: 98.86% (@ 210 nm-400 nm) (Rt; 7.756; Method: YMC TRIART C-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 12.73 (s, 1H), 8.24 (d, J=1.8 Hz, 1H), 8.12 (dt, J=8.0, 1.3 Hz, 1H), 7.94 (dd, J=10.1, 7.7 Hz, 3H), 7.78 (t, J=7.8 Hz, 1H), 7.70-7.63 (m, 2H), 6.86 (s, 1H), 4.08 (d, J=7.4 Hz, 2H), 3.32 (s, 3H), 2.07 (dp, J=13.8, 6.9 Hz, 1H), 0.73 (d, J=6.7 Hz, 6H).

Examples 7 and 8: Synthesis of Ethyl 5-(4'-(hydroxymethyl)-3'-(methylsulfonyl)[1,1'-biphenyl]-4-yl)-1-isobutyl-1H-pyrazole-3-carboxylate (Example 7) and 5-(4'-(Hydroxymethyl)-3'-(methylsulfonyl)-[1,1'-biphenyl]-4-yl)-1-isobutyl-1H-pyrazole-3-carboxylic acid (Example 8)

Examples 7 and 8 were made by a process analogous to Scheme B, but using the bornate shown in the scheme below.

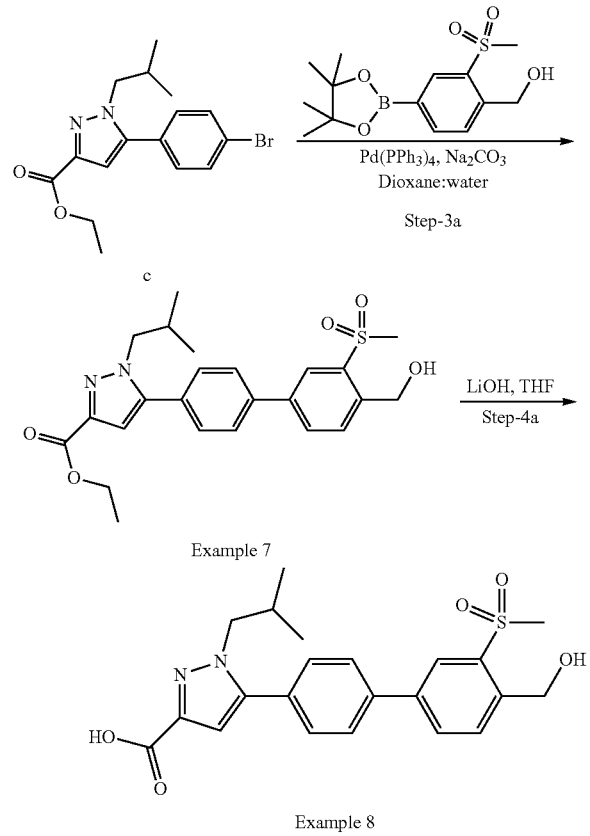

Step 3a: Ethyl 5-(4'-(hydroxymethyl)-3'-(methylsulfonyl)-[1,1'-biphenyl]-4-yl)-1-isobutyl-1H-pyrazole-3-carboxylate (Example 7)

To a stirred solution of compound c from step 2 of Example 5 (1 g, 2.85 mmol) and (2-(methylsulfonyl)-4-(4,4,5,5-tetramethyl-1,3,2-dioxaborolan-2-yl)phenyl)methanol (1.3 g, 4.28 mmol) in dioxane/water mixture (10 mL+4 mL), Na₂CO₃ (0.76 g, 7.14 mmol) was added and the solution was purged with argon for 10 min. Then Pd (PPh₃)₄ (0.33 g, 0.285 mmol) was added and argon was purged again for 10 min. The reaction mass was heated at 80° C. for 16 h. The progress of the reaction was monitored by TLC. Upon completion the reaction mixture diluted with water and extracted with ethyl acetate. The combined organic layers were dried over Na₂SO₄ and concentrated under reduced pressure. The crude compound was purified by column chromatography to afford the desired compound Example 7 (1 g, 77%). LCMS: 457.35 (M+1)⁺; HPLC: 98.29% (@ 210 nm-400 nm) (Rt; 8.802; Method: YMC TRIARTC-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 8.21-8.08 (m, 2H), 7.89 (dd, J=8.1, 4.6 Hz, 3H), 7.70-7.63 (m, 2H), 6.90 (s, 1H), 5.55 (t, J=5.6 Hz, 1H), 4.97 (d, J=5.6 Hz, 2H), 4.30 (q, J=7.1 Hz, 2H), 4.09 (d, J=7.4 Hz, 2H), 3.33 (s, 3H), 2.06 (dp, J=13.7, 6.7 Hz, 1H), 1.31 (t, J=7.1 Hz, 3H), 0.73 (d, J=6.7 Hz, 6H).

Step 4a: 5-(4'-(Hydroxymethyl)-3'-(methylsulfonyl)-[1,1'-biphenyl]-4-yl)-1-isobutyl-1H-pyrazole-3-carboxylic acid (Example 8)

To a stirred solution of Example 7 (0.3 g, 0.657 mmol) in THF (3 mL), LiOH (0.031 g, 1.32 mmol in 1 mL H₂O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with 10% MeOH/DCM. The combined organic layers were dried over Na₂SO₄ and concentrated under reduced pressure. The crude compound was purified by acetonitrile and diethyl ether washings to afford the desired compound Example 8 (0.25 g, 89%). LCMS: 429.30 (M+1)⁺; HPLC: 98.89% (@ 210 nm-400 nm) (Rt; 6.968; Method: YMC TRIART C-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 12.74 (s, 1H), 8.21-8.08 (m, 2H), 7.91-7.87 (m, 3H), 7.74-7.62 (m, 2H), 6.85 (s, 1H), 5.55 (t, J=5.6 Hz, 1H), 4.97 (d, J=5.5 Hz, 2H), 4.07 (d, J=7.4 Hz, 2H), 3.33 (s, 3H), 2.07 (hept, J=6.6 Hz, 1H), 0.73 (d, J=6.7 Hz, 6H).

Examples 9 and 10: Synthesis of Ethyl 2-isobutyl-1-(3'-(methylsulfonyl)-[1,1'-biphenyl]-4-yl)-1H-imidazole-4-carboxylate (Example 9) and 2-Isobutyl-1-(3'-(methylsulfonyl)-[1,1'-biphenyl]-4-yl)-1H-imidazole-4-carboxylic acid (Example 10)

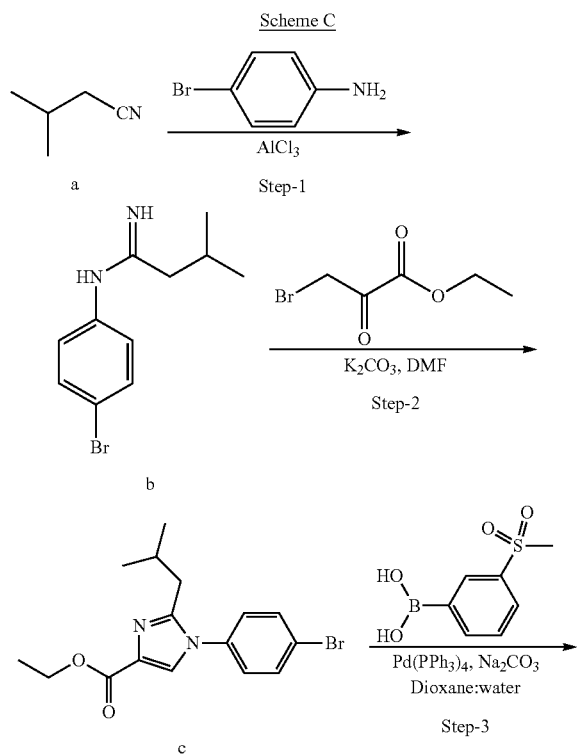

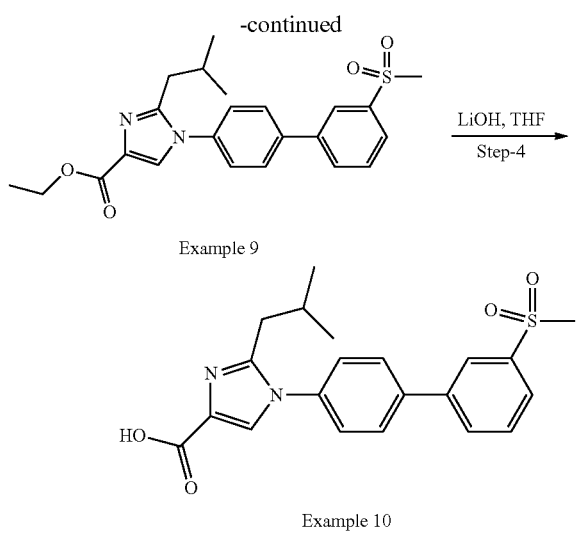

Example 9

Example 10

Step 1: N-(4-Bromophenyl)-3-methylbutanimidamide (b)

To a mixture of 4-bromoaniline (2.27 g, 13.25 mmol) and 3-methylbutanenitrile (1 g, 12.05 mmol) at 0° C., AlCl₃ (1.76 g, 13.25 mmol) was added portion wise. The resulting reaction mixture was stirred at 90° C. for 2 h. The progress of the reaction was monitored by TLC. Upon completion the reaction mixture was quenched with ice cold water and extracted with ethyl acetate. The combined organic layers were dried over anhydrous Na₂SO₄ and concentrated under reduced pressure resulting in a crude compound which was purified by column chromatography to afford the compound b (1.5 g, 49%).

Step 2: Ethyl 1-(4-bromophenyl)-2-isobutyl-1H-imidazole-4-carboxylate (c)

To a stirred solution of compound b (0.5 g, 1.96 mmol) in DMF(5 mL), ethyl 3-bromo-2-oxopropanoate (0.57 g, 2.94 mmol) and potassium carbonate (0.67 g, 4.9) were added and the resulting reaction mixture was stirred at 90° C. for 16 h. The progress of the reaction was monitored by TLC. Upon completion the reaction mixture was quenched with ice cold water and extracted with ethyl acetate. The combined organic layers were dried over anhydrous Na₂SO₄ and concentrated under reduced pressure resulting in a crude compound which was purified by column chromatography to afford the compound c (0.3 g, 44%).

Step 3: Ethyl 2-isobutyl-1-(3'-(methylsulfonyl)-[1,1'-biphenyl]-4-yl)-1H-imidazole-4-carboxylate (Example 9)

To a stirred solution of compound c (0.3 g, 0.854 mmol) and (3-(methylsulfonyl) phenyl) boronic acid (0.188 g, 0.940 mmol) in dioxane/water mixture (8 mL+2 mL), Na₂CO₃ (0.22 g, 2.13 mmol) was added and the solution was purged with argon for 10 min. Then Pd (PPh₃)₄ (0.098 g, 0.0854 mmol) was added and argon was purged again for 10 min. The reaction mass was heated at 100° C. for 3 h. The progress of the reaction was monitored by TLC. Upon completion the reaction mixture diluted with water and extracted with ethyl acetate. The combined organic layers were dried over Na₂SO₄ and concentrated under reduced pressure. The crude compound was purified by column chromatography to afford the desired compound Example 9 (0.26 g, 72.2%). LCMS: 427.25 (M+1)⁺; HPLC: 99.92% (@ 210 nm-400 nm) (Rt; 7.376; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 8.25 (d, J=1.9 Hz, 1H), 8.17-8.09 (m, 1H), 8.04-7.88 (m, 4H), 7.79 (t, J=7.8 Hz, 1H), 7.64 (d, J=8.3 Hz, 2H), 4.25 (q, J=7.1 Hz, 2H), 2.55 (d, J=7.2 Hz, 2H), 1.94 (dt, J=13.7, 6.8 Hz, 1H), 1.29 (t, J=7.1 Hz, 3H), 0.81 (d, J=6.6 Hz, 6H), 3H merged in solvent peak.

Step 4: 2-Isobutyl-1-(3'-(methylsulfonyl)-[1,1'-biphenyl]-4-yl)-1H-imidazole-4-carboxylic acid (Example 10)

To a stirred solution of Example 9 (0.06 g, 0.141 mmol) in THF (1 mL), LiOH (0.007 g, 0.281 mmol in 0.5 mL H₂O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with ethyl acetate. The combined organic layers were dried over Na₂SO₄ and concentrated under reduced pressure. The crude compound was purified by acetonitrile and diethyl ether washings to afford the desired compound Example 10 (0.035 g, 64%). LCMS: 399.00 (M+1)⁺; HPLC: 99.24% (@ 210 nm-400 nm) (Rt; 6.746; Method: YMC TRIART C-18 (150 mm×4.6 mm×3μ); ID:E-AC-2/13/COL/03, Mobile Phase: A; 0.05% TFA in water/B: 0.05% TFA in acetonitrile Inj. Vol: 10 μL, Col. Temp.: Ambient; Flow rate: 1.0 mL/min.; Gradient: 5% B to 95% B in 8 min, Hold till 9.5 min, 5% B in 13.0 min. hold till 15.0 min); ¹H NMR (400 MHz, DMSO-d6) δ 8.34-8.23 (m, 2H), 8.14 (dt, J=7.9, 1.4 Hz, 1H), 8.07-7.94 (m, 3H), 7.85-7.71 (m, 3H), 2.69 (d, J=7.4 Hz, 2H), 1.91 (p, J=6.8 Hz, 1H), 0.80 (d, J=6.6 Hz, 6H), 3H merged in solvent peak.

Examples 11 and 12: Synthesis of Ethyl 1-(4'-(hydroxymethyl)-3'-(methylsulfonyl)-[1,1'-biphenyl]-4-yl)-2-isobutyl-1H-imidazole-4-carboxylate (Example 11) and 1-(4'-(Hydroxymethyl)-3'-(methylsulfonyl)-[1,1'-biphenyl]-4-yl)-2-isobutyl-1H-imidazole-4-carboxylic acid (Example 12)

Examples 11 and 12 were made by a process analogous to that of Scheme C, except using the boronate in the scheme below.

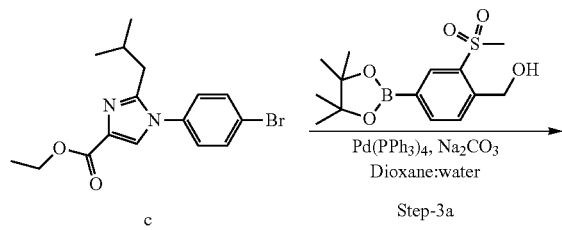

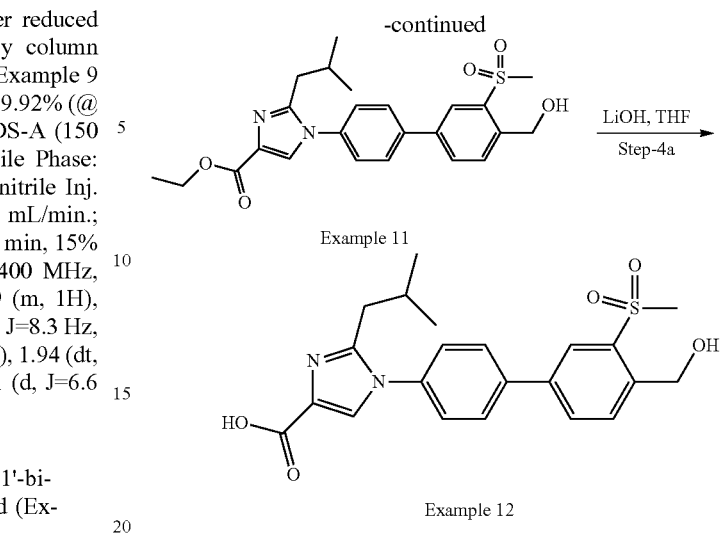

Example 11

Example 12

Step 3a: Ethyl 1-(4'-(hydroxymethyl)-3'-(methylsulfonyl)[1,1'-biphenyl]-4-yl)-2-isobutyl-1H-imidazole-4-carboxylate (Example 11)

To a stirred solution of compound c from step 2 of Example 9 (0.37 g, 1.05 mmol) and (2-(methylsulfonyl)-4-(4,4,5,5-tetramethyl-1,3,2-dioxaborolan-2-yl)phenyl) methanol (0.496 g, 1.58 mmol) in dioxane/water mixture (4 mL+1 mL), Na₂CO₃ (0.28 g, 2.64 mmol) was added and the solution was purged with argon for 10 min. Then Pd (PPh₃)₄ (0.121 g, 0.105 mmol) was added and argon was purged again for 10 min. The reaction mass was heated at 100° C. for 16 h. The progress of the reaction was monitored by TLC. Upon completion the reaction mixture diluted with water and extracted with ethyl acetate. The combined organic layers were dried over Na₂SO₄ and concentrated under reduced pressure. The crude compound was purified by column chromatography to afford the desired compound Example 11 (0.13 g, 27.1%). LCMS: 457.30 (M+1)⁺; HPLC: 99.07% (@ 210 nm-400 nm) (Rt; 6.833; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, CDCl₃) δ 8.32 (s, 1H), 7.91 (d, J=7.3 Hz, 1H), 7.79-7.66 (m, 4H), 7.41 (d, J=8.0 Hz, 2H), 5.03 (d, J=6.6 Hz, 2H), 4.41 (q, J=7.2 Hz, 2H), 3.25 (s, 3H), 2.99 (t, J=6.6 Hz, 1H), 2.61 (d, J=7.4 Hz, 2H), 2.07 (dt, J=14.0, 7.0 Hz, 1H), 1.40 (t, J=7.3 Hz, 3H), 0.84 (d, J=6.7 Hz, 6H).

Step 4a: 1-(4'-(Hydroxymethyl)-3'-(methylsulfonyl)-[1,1'-biphenyl]-4-yl)-2-isobutyl-1H-imidazole-4-carboxylic acid (Example 12)

To a stirred solution of Example 11 (0.13 g, 0.285 mmol) in THF (2 mL), LiOH (0.013 g, 0.570 mmol in 0.5 mL H₂O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with ethyl acetate. The combined organic layers were dried over Na₂SO₄ and concentrated under reduced pressure. The crude compound was purified by acetonitrile and diethyl ether washings to afford the desired compound Example 12 (0.02 g, 17%). LCMS: 429.25 (M+1)+; HPLC: 95.41% (@ 210 nm-400 nm) (Rt; 6.267; Method: YMC Triart Basic (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 8.22-8.09 (m, 2H), 7.96-7.86 (m, 4H), 7.66-7.58 (m, 2H), 5.57 (s, 1H), 4.97 (s, 2H), 3.34 (s, 3H), 2.54 (d, J=7.0 Hz, 2H), 2.03-1.88 (m, 1H), 0.82 (d, J=6.7 Hz, 6H).

Examples 13 and 14: Synthesis of Ethyl 2-(5-(3'-(methylsulfonyl)-[1,1'-biphenyl]-4-yl)-3-(prop-1-en-2-yl)-1H-pyrazol-1-yl)acetate (Example 13) and 2-(5-(3'-(Methylsulfonyl)-[1,1'-biphenyl]-4-yl)-3-(prop-1-en-2-yl)-1H-pyrazol-1-yl)acetic acid (Example 14)

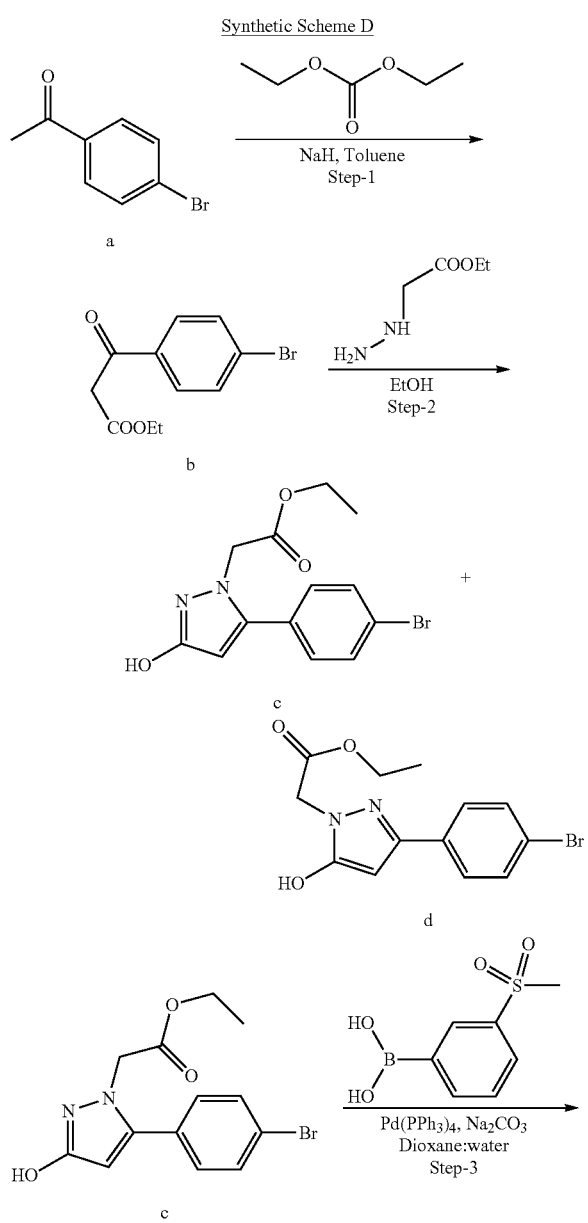

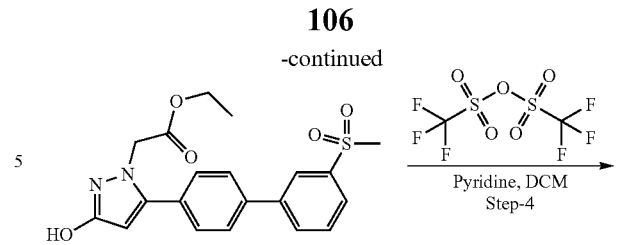

Step 1: Ethyl 3-(4-bromophenyl)-3-oxopropanoate (b)

To a stirred solution of NaH (60%, 4.2 g, 105.5 mmol) in toluene (100 mL) at 0° C., diethyl carbonate (8.9 g, 75.37 mmol) was added and the solution was stirred at rt for 2 h. To this solution, compound a (10 g, g, 50.25 mmol) was added at 110° C. and the resulting reaction mixture was stirred at 110° C. for 12 h. The progress of the reaction was monitored by TLC. Upon completion the reaction mixture was cooled to rt, diluted with 1N HCl and extracted with ethyl acetate. The combined organic layers were dried over anhydrous Na$_2$SO$_4$ and concentrated under reduced pressure resulting in a crude compound which was purified by column chromatography to afford the compound b (5 g, 37%).

Step 2: Ethyl 2-(5-(4-bromophenyl)-3-hydroxy-1H-pyrazol-1-yl) acetate (c)

To a stirred solution of compound b (2.5 g, 9.26 mmol) in EtOH (30 mL), ethyl 2-hydrazinoacetate hydrochoride (1.71 g, 11.11 mmol) and acetic acid (0.5 mL, 9.26 mmol) were added and the resulting reaction mixture was stirred at 80°

C. for 3 h. The progress of the reaction was monitored by TLC. Upon completion the reaction mixture was concentrated to dryness under reduced pressure. The residue obtained was diluted with water and extracted with ethyl acetate. The combined organic layers were dried over anhydrous Na₂SO₄ and concentrated under reduced pressure resulting in a crude compound which was purified by column chromatography to afford the compound c (1 g, 33%) confirmed by NOE.

Step 3: Ethyl 2-(3-hydroxy-5-(3'-(methylsulfonyl)-[1,1'-biphenyl]-4-yl)-1H-pyrazol-1-yl)acetate (e)

To a stirred solution of compound c (1 g, 3.08 mmol) and (3-(methylsulfonyl) phenyl) boronic acid (0.648 g, 3.24 mmol) in dioxane/water mixture (8 mL+2 mL), $Na_2CO_3$ (0.817 g, 7.71 mmol) was added and the solution was purged with argon for 10 min. Then Pd $(PPh_3)_4$ (0.356 g, 0.308 mmol) was added and argon was purged again for 10 min. The reaction mass was heated at 80° C. for 3 h. The progress of the reaction was monitored by TLC. Upon completion the reaction mixture diluted with water and extracted with ethyl acetate. The combined organic layers were dried over $Na_2SO_4$ and concentrated under reduced pressure. The crude compound was purified by column chromatography to afford the desired compound e (0.3 g, 25%).

Step 4: Ethyl 2-(5-(3'-(methylsulfonyl)-[1,1'-biphenyl]-4-yl)-3-(((trifluoromethyl)sulfonyl)oxy)-1H-pyrazol-1-yl)acetate (f)

To a stirred solution of compound e (0.3 g, 0.75 mmol) in DCM (5 mL) at 0° C., pyridine (0.118 g, 1.50 mmol) and trifluoromethanesulfonic anhydride (0.254 g, 0.9 mmol) were added and the resulting reaction mixture was stirred at rt for 3 h. The progress of the reaction was monitored by TLC. Upon completion the reaction mixture was diluted with water and extracted with DCM. The combined organic layers were dried over anhydrous $Na_2SO_4$ and concentrated under reduced pressure resulting in a crude compound which was purified by column chromatography to afford the compound f (0.2 g, 50.1%).

Step 5: Ethyl 2-(5-(3'-(methylsulfonyl)-[1,1'-biphenyl]-4-yl)-3-(prop-1-en-2-yl)-1H-pyrazol-1-yl)acetate (Example 13)

To a stirred solution of compound f (0.2 g, 0.375 mmol) and 4,4,5,5-tetramethyl-2-(prop-1-en-2-yl)-1,3,2-dioxaborolane (0.066 g, 0.394 mmol) in dioxane/water mixture (4 mL+1 mL), $Na_2CO_3$ (0.099 g, 0.939 mmol) was added and the solution was purged with argon for 10 min. Then Pd $(PPh_3)_4$ (0.043 g, 0.0375 mmol) was added and argon was purged again for 10 min. The reaction mass was heated at 80° C. for 3 h. The progress of the reaction was monitored by TLC. Upon completion the reaction mixture diluted with water and extracted with ethyl acetate. The combined organic layers were dried over $Na_2SO_4$ and concentrated under reduced pressure. The crude compound was purified by column chromatography to afford the desired compound Example 13 (0.02 g, 13%). LCMS: 425.20 (M+1)⁺; HPLC: 99.56% (@ 210 nm-400 nm) (Rt; 8.998; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 8.21 (t, J=1.8 Hz, 1H), 8.09 (dt, J=7.9, 1.4 Hz, 1H), 8.01-7.88 (m, 3H), 7.88-7.71 (m, 3H), 6.94 (s, 1H), 5.39-5.33 (m, 1H), 5.15 (d, J=7.7 Hz, 3H), 4.18 (q, J=7.1 Hz, 2H), 2.54 (d, J=11.6 Hz, 3H), 1.22 (t, J=7.1 Hz, 3H), 3H merged in solvent peak.

Step 6: 2-(5-(3'-(Methylsulfonyl)[1,1'-biphenyl]-4-yl)-3-(prop-1-en-2-yl)-1H-pyrazol-1-yl)acetic acid (Example 14)

To a stirred solution of Example 13 (0.05 g, 0.117 mmol) in THF (1 mL), LiOH (0.006 g, 0.235 mmol in 0.5 mL H₂O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with ethyl acetate. The combined organic layers were dried over Na₂SO₄ and concentrated under reduced pressure. The crude compound was purified by acetonitrile and diethyl ether washings to afford the desired compound Example 14 (0.03 g, 65.2%). LCMS: 397.15 (M+1)⁺; HPLC: 99.41% (@ 210 nm-400 nm) (Rt; 7.518; Method: YMC ODS-A (150 mm×4.6 mm×3μ); ID:E-AC-2/13/COL/01, Mobile Phase: A; 0.05% TFA in water/B: 0.05% TFA in acetonitrile Inj. Vol: 10 μL, Col. Temp.: Ambient; Flow rate: 1.0 mL/min.; Gradient: 15% B to 95% B in 8 min, Hold till 9.5 min, 15% B in 13.0 min. hold till 15.0 min); ¹H NMR (400 MHz, DMSO-d6) δ 8.21 (s, 1H), 8.09 (d, J=7.8 Hz, 1H), 7.93 (dd, J=12.3, 7.7 Hz, 3H), 7.87-7.71 (m, 3H), 6.91 (s, 1H), 5.35 (s, 1H), 5.18 (s, 1H), 4.98 (s, 2H), 3.17 (s, 3H), 2.09 (s, 3H).

Examples 15 and 16: Synthesis of Ethyl 2-(3-isopropyl-5-(3'-(methylsulfonyl)-[1,1'-biphenyl]-4-yl)-1H-pyrazol-1-yl)acetate (Example 15) and 2-(3-Isopropyl-5-(3'-(methylsulfonyl)-[1,1'-biphenyl]-4-yl)-1H-pyrazol-1-yl)acetic acid (Example 16)

Scheme E

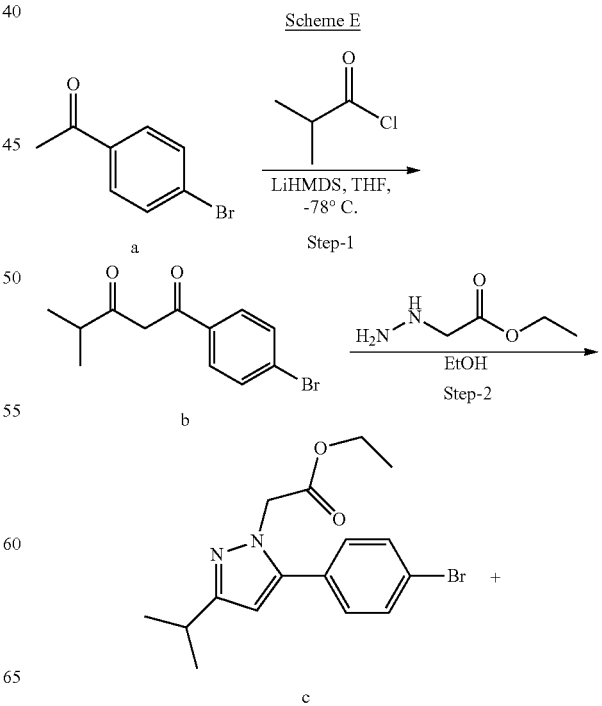

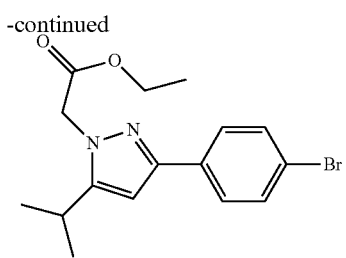
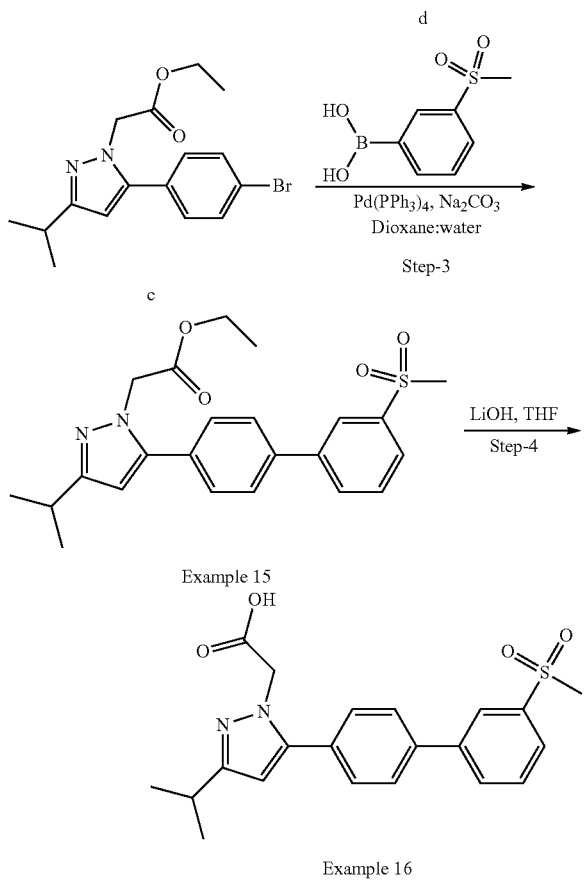

Step 1:
1-(4-Bromophenyl)-4-methylpentane-1,3-dione (b)

To a stirred solution of 1-(4-bromophenyl)ethanone (2 g, 10.05 mmol) in dry THF (20 mL) at −78° C., LiHMDS (1 M, 15 mL, 15.07 mmol) was added and the solution was stirred at same temperature for 1 h. To this solution, isobutyryl chloride (1.53 g, 15.07 mmol) in THF (10 mL) was added at −78° C. and the resulting reaction mixture was stirred at rt for 12 h. The progress of the reaction was monitored by TLC. Upon completion the reaction mixture was quenched with aqueous sat. NH$_4$Cl solution and extracted with ethyl acetate. The combined organic layers were dried over anhydrous Na$_2$SO$_4$ and concentrated under reduced pressure resulting in a crude compound which was purified by column chromatography to afford the compound b (2 g, 68%).

Step 2: Ethyl 2-(5-(4-bromophenyl)-3-isopropyl-1H-pyrazol-1-yl) acetate (c)

To a stirred solution of compound b (2 g, 7.46 mmol) in EtOH (20 mL), ethyl 2-hydrazinoacetate (1.26 g, 8.21 mmol) was added and the resulting reaction mixture was stirred at 80° C. for 3 h. The progress of the reaction was monitored by TLC. Upon completion the reaction mixture was concentrated to dryness under reduced pressure. The residue obtained was diluted with water and extracted with ethyl acetate. The combined organic layers were dried over anhydrous Na$_2$SO$_4$ and concentrated under reduced pressure resulting in a crude compound which was purified by column chromatography to afford the compound c (0.7 g, 27%) confirmed by NOE.

Step 3: Ethyl 2-(3-isopropyl-5-(3'-(methylsulfonyl)-[1,1'-biphenyl]-4-yl)-1H-pyrazol-1-yl)acetate (Example 15)

To a stirred solution of compound c (0.7 g, 1.99 mmol) and (3-(methylsulfonyl)phenyl)boronic acid (0.439 g, 2.19 mmol) in dioxane/water mixture (8 mL+2 mL), Na$_2$CO$_3$ (0.422 g, 3.98 mmol) was added and the solution was purged with argon for 10 min. Then Pd (PPh$_3$)$_4$ (0.23 g, 0.199 mmol) was added and argon was purged again for 10 min. The reaction mass was heated at 100° C. for 3 h. The progress of the reaction was monitored by TLC. Upon completion the reaction mixture diluted with water and extracted with ethyl acetate. The combined organic layers were dried over Na$_2$SO$_4$ and concentrated under reduced pressure. The crude compound was purified by column chromatography to afford the desired compound Example 15 (0.7 g, 83.3%). LCMS: 427.25 (M+1)$^+$; HPLC: 98.97% (@ 210 nm-400 nm) (Rt; 9.396; Method: YMC TRIARTC-18 (150 mm×4.6 mm×3µ); ID:E-AC-2/13/COL/03, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 8.24-8.19 (m, 1H), 8.10 (d, J=7.8 Hz, 1H), 7.91 (dd, J=20.9, 7.9 Hz, 3H), 7.77 (t, J=7.8 Hz, 1H), 7.58 (d, J=8.0 Hz, 2H), 6.37 (s, 1H), 4.99 (s, 2H), 4.10 (q, J=7.1 Hz, 2H), 3.31 (s, 3H), 2.91 (p, J=6.9 Hz, 1H), 1.27-1.09 (m, 9H).

Step 4: 2-(3-Isopropyl-5-(3'-(methylsulfonyl)-[1,1'-biphenyl]-4-yl)-1H-pyrazol-1-yl)acetic acid (Example 16)

To a stirred solution of Example 15 (0.1 g, 0.234 mmol) in THF (1 mL), LiOH (0.011 g, 0.468 mmol in 1 mL H$_2$O) was added and the reaction mass was stirred at rt for 12 h. The progress of the reaction was monitored by TLC. Upon completion the reaction mixture was concentrated to dryness under reduced pressure. The residue obtained was acidified with 1N HCl up to pH=2 and extracted with ethyl acetate. The combined organic layers were dried over Na$_2$SO$_4$ and concentrated under reduced pressure. The crude compound was purified by acetonitrile and diethyl ether washings to afford the desired compound Example 16 (0.076 g, 82%). LCMS: 399.15 (M+1)$^+$; HPLC: 98.51% (@ 210 nm-400 nm) (Rt; 7.463; Method: YMC ODS-A (150 mm×4.6 mm×3µ); ID:E-AC-2/13/COL/01, Mobile Phase: A; 0.05% TFA in water/B: 0.05% TFA in acetonitrile Inj. Vol: 10 µL, Col. Temp.: Ambient; Flow rate: 1.0 mL/min.; Gradient: 15% B to 95% B in 8 min, Hold till 9.5 min, 15% B in 13.0 min. hold till 15.0 min); $^1$H NMR (400 MHz, DMSO-d6) δ 13.06 (s, 1H), 8.22 (t, J=1.8 Hz, 1H), 8.10 (dt, J=7.9, 1.5 Hz, 1H), 7.97-7.84 (m, 3H), 7.77 (t, J=7.8 Hz, 1H), 7.59 (d, J=8.1 Hz, 2H), 6.35 (s, 1H), 4.88 (s, 2H), 2.91 (p, J=6.9 Hz, 1H), 1.24 (dd, J=6.8, 1.1 Hz, 6H), 3H merged in solvent peak.

Example 17: Additional Examples

Additional example compounds can be prepared as shown in the table below using modified versions of the schemes described and from procedures and reagents described for related compounds.

| Example | Name | Structure | Synthetic Scheme |
|---|---|---|---|
| 17A | ethyl 2-(4-isopropyl-1-(3'-(methylsulfonyl)-[1,1'-biphenyl]-4-yl)-1H-imidazol-2-yl)acetate | 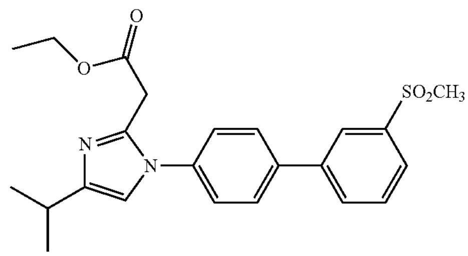 [SMILES: CCOC(=O)Cc1nc(C(C)C)cn1-c1ccc(-c2cccc(S(C)(=O)=O)c2)cc1] | A |
| 17B | 2-(4-isopropyl-1-(3'-(methylsulfonyl)-[1,1'-biphenyl]-4-yl)-1H-imidazol-2-yl)acetic acid | 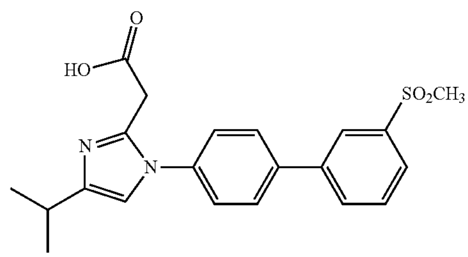 [SMILES: CC(C)c1cn(-c2ccc(-c3cccc(S(C)(=O)=O)c3)cc2)c(CC(=O)O)n1] | A |
| 17C | 2-(4-(2-hydroxypropan-2-yl)-1-(3'-(methylsulfonyl)-[1,1'-biphenyl]-4-yl)-1H-imidazol-2-yl)acetic acid | 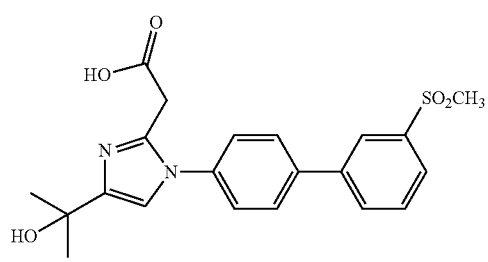 [SMILES: CC(C)(O)c1cn(-c2ccc(-c3cccc(S(C)(=O)=O)c3)cc2)c(CC(=O)O)n1] | C |
| 17D | ethyl 2-(1-(4'-(hydroxymethyl)-3'-(methylsulfonyl)-[1,1'-biphenyl]-4-yl)-4-isopropyl-1H-imidazol-2-yl)acetate | 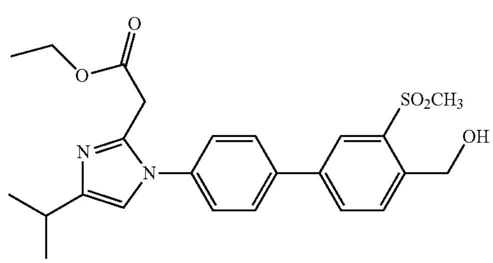 [SMILES: CCOC(=O)Cc1nc(C(C)C)cn1-c1ccc(-c2ccc(CO)c(S(C)(=O)=O)c2)cc1] | A |
| 17E | 2-(1-(4'-(hydroxymethyl)-3'-(methylsulfonyl)-[1,1'-biphenyl]-4-yl)-4-isopropyl-1H-imidazol-2-yl)acetic acid | 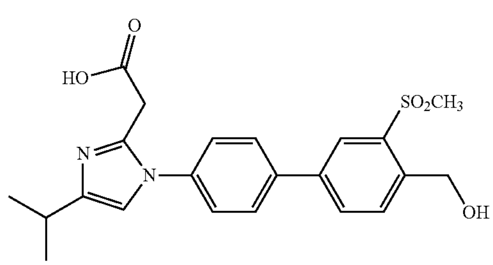 [SMILES: CC(C)c1cn(-c2ccc(-c3ccc(CO)c(S(C)(=O)=O)c3)cc2)c(CC(=O)O)n1] | A |
| 17F | ethyl 2-(3-(2-hydroxypropan-2-yl)-5-(3'-(methylsulfonyl)-[1,1'-biphenyl]-4-yl)-1H-pyrazol-1-yl)acetate | 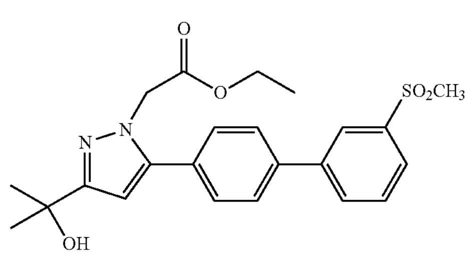 [SMILES: CCOC(=O)Cn1nc(C(C)(C)O)cc1-c1ccc(-c2cccc(S(C)(=O)=O)c2)cc1] | B |

-continued

| Example | Name | Structure | Synthetic Scheme |
|---------|------|-----------|------------------|
| 17G | ethyl 2-(5-(4'-(hydroxymethyl)-3'-(methylsulfonyl)-[1,1'-biphenyl]-4-yl)-3-(2-hydroxypropan-2-yl)-1H-pyrazol-1-yl)acetate | 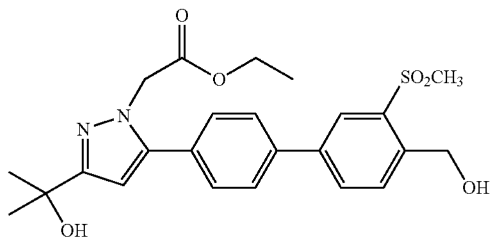 [SMILES: CCOC(=O)Cn1nc(C(C)(C)O)cc1-c1ccc(-c2ccc(CO)c(S(C)(=O)=O)c2)cc1] | B |
| 17H | ethyl 2-(5-(4'-(hydroxymethyl)-3'-(methylsulfonyl)-[1,1'-biphenyl]-4-yl)-3-(prop-1-en-2-yl)-1H-pyrazol-1-yl)acetate | 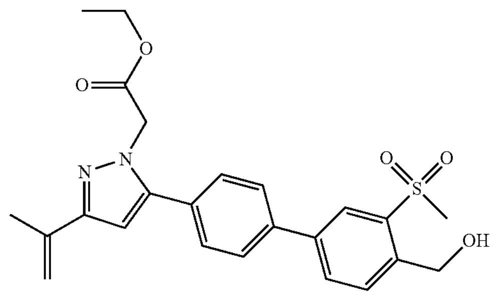 | D |
| 17I | 2-(5-(4'-(hydroxymethyl)-3'-(methylsulfonyl)-[1,1'-biphenyl]-4-yl)-3-(prop-1-en-2-yl)-1H-pyrazol-1-yl)acetic acid | 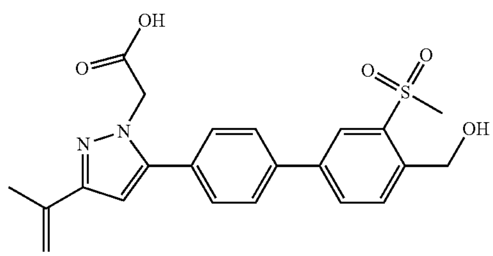 [SMILES: C=C(C)c1cc(-c2ccc(-c3ccc(CO)c(S(C)(=O)=O)c3)cc2)n(CC(=O)O)n1] | D |
| 17J | ethyl 2-(5-(4'-(hydroxymethyl)-3'-(methylsulfonyl)-[1,1'-biphenyl]-4-yl)-3-isopropyl-1H-pyrazol-1-yl)acetate | 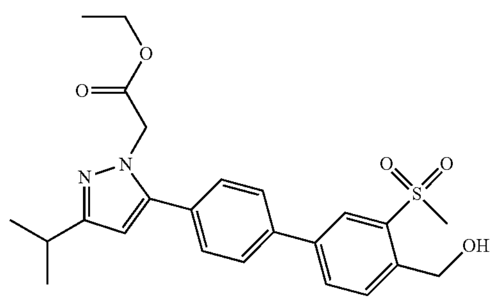 [SMILES: CCOC(=O)Cn1nc(C(C)C)cc1-c1ccc(-c2ccc(CO)c(S(C)(=O)=O)c2)cc1] | E |
| 17K | 2-(5-(4'-(hydroxymethyl)-3'-(methylsulfonyl)-[1,1'-biphenyl]-4-yl)-3-isopropyl-1H-pyrazol-1-yl)acetic acid | 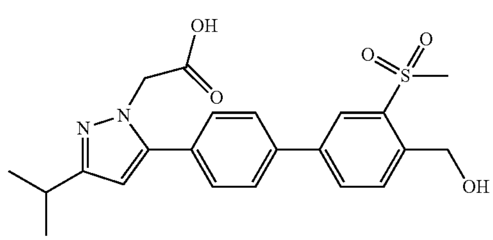 [SMILES: CC(C)c1cc(-c2ccc(-c3ccc(CO)c(S(C)(=O)=O)c3)cc2)n(CC(=O)O)n1] | E |
| 17L | ethyl 2-(4-(2-hydroxypropan-2-yl)-1-(3'-(methylsulfonyl)-[1,1'-biphenyl]-4-yl)-1H-imidazol-2-yl)acetate | 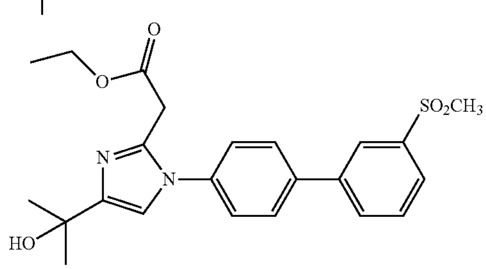 | C |

Example A1: RNA Extraction

Add QIAzol® Lysis Reagent (QIAGEN Cat Number 79306) to the cells. Scrape the cells and place into a Falcon Polypropylene tube. Let stand at room temperature for 5 minutes. Add 1 ml of cells to microfuge tubes. Add 200 µl of chloroform, vortex, let stand for 5 minutes. Centrifuge at 4° C. for 15 minutes at 14,000 RPM. Add an equal volume of 70% ETOH (diluted with DEPC water). Add 600 µl to the RNeasy® column from the RNeasy® Mini Kit (QIAGEN Cat. Number 74106) centrifuge at 14,000 RPM at room temperature for 1 minute, discard flow-through. Add remainder of sample to the column, centrifuge, discard flow-through. Add 350 µl of RW1 buffer from the RNeasy® Mini Kit to the column, centrifuge at room temperature for 1 minute, discard flow-through. DNase column with RNase-Free DNase Set (QIAGEN cat. Number 79254) by making DNase I stock solution, add 550 µl of water to the DNase, add 10 µl of DNase to 70 µl of BufferRDD for each sample, mix, add 80 µl to the column, let stand for 15 minutes. Add 350 µl of RW1 buffer to column, centrifuge for 1 minute, discard flow-through. Add 500 µl RPE buffer to column, centrifuge for 1 minute, discard flow-through. Add 500 µl RPE buffer to column, centrifuge for 1 minute, discard flow-through. Put column into a clean 2.0 ml microfuge tube, centrifuge for 2 minutes. Put column into a microfuge tube, add 50 µl of water, allow column to stand for 2 minutes, centrifuge for 1 minute.

Quantitative PCR

TaqMan technology is used for quantitative PCR for the evaluation of MMP, TNFα, TIMP, IL-8, ASAH1, SPTLC$_1$, SMPD1, LASS2, TXNRD1, GPX3, GSR, CAT, ApoE, ABCA1, ABCA2, ABCA12, ABCA13, ABCG1, aSyn, decorin, and LXRα/β gene expression in keratinocytes and fibroblasts.

Conditions for use of TaqMan Reverse Transcriptase Reagents (Applied Biosystems Cat. Number N808-0234): 10×RT buffer: 10 µl, MgCl$_2$ solution: 22 µl, DNTP mix: 20 µl, Random Hexamers: 5 µl, Multi Scribe RT: 2.5 µl, RNase Inhibitor: 2.5 µl, 2 µg RNA. Thermocycler: 25° C.-10 minutes, 48° C.-30 minutes, 95° C.-5 minutes.

Setup TaqMan with QuantiTect Multiplex PCR Kit (QIAGEN cat. Number 204543): 2× master mix: 25 µl; Single Tube Assay: 2.5 µl; Applied Biosystems Primers Probe set (part number 4308329)-18S forward primer: 0.25 µl, 18S reverse primer: 0.25 µl, 18S probe: 0.25 µl; water to 50 µl; 5 µl cDNA. Thermocycler: 50° C.-2 minutes, 95° C.-10 minutes, 95° C.-15 seconds, 60° C.-1 minute.

Example A2: Induction of Expression of LXR Receptors

Clonetics® Normal Human Epidermal Keratinocytes (NHEKs) are obtained from Cambrex Bio Science, Inc. The proliferating T-25 (C$_{2503}$TA25) pooled, neonatal keratinocytes are expanded in Clonetics® KGM-2 serum-free medium (CC-3107) and subcultured as needed using the recommended Clonetics® ReagentPack™ (CC-5034). Due to a light-sensitive component in the medium, all manipulations are done in low light.

For experiments, 1.6 million NHEK cells are plated in growth medium on 100 mm dishes and allowed to grow to ~75% confluence. On the day of treatment, the dishes are rinsed once with KGM-2 minus hydrocortisone; then, vehicle (0.1% DMSO) or 1 µM or an LXR agonist described herein, is added for 6 h in hydrocortisone-deficient KGM-2. After 6 h, the treatment medium is temporarily removed, the dishes washed with Dulbecco's Phosphate Buffered Saline, and then half of the treatments are exposed to 8 J/m$^2$ ultraviolet light using a Stratagene UV Stratalinker® 2400. Treatments are replaced and 18 h later the samples are harvested for RNA processing using TRIzol®D Reagent (Invitrogen).

RNA is extracted as described above. UV irradiation of NHEKs slightly reduced the expression of LXRα. Treatment of keratinocytes with the LXR modulator (1 µM) induces the expression of LXRα in both UV-unexposed and UV-exposed keratinocytes. UV treatment of NHEKs down-regulates LXRβ expression, and this UV-mediated inhibition of LXRβ expression is reversed by treatment with the LXR modulator. Therefore, induction of expression of both LXR receptors in UV-exposed keratinocytes by an LXR modulator indicates efficacy of the LXT modulator. Further, LXR modulators may help the UV-exposed keratinocytes/skin to be more responsive to its effects.

Gal4 LXRβ Cotransfection Assay

For transient transfection of HEK 293 cells, 6×10$^3$ cells are plated into 96-well dishes. Each well is transfected with 25 ng 5×UAS-luciferase reporter (pG5luc) and 25 ng of µM human LXRβ (AA 153-461) LBD plasmid using Fugene 6 reagent (Roche; Indianapolis, Ind.). The chimeric protein is assessed for the ability to transactivate a Gal4-responsive luciferase reporter plasmid in a concentration-responsive manner to compounds (0.01-10 µM). Luciferase activity at each dose concentration is measured in triplicate using standard substrate reagents (BD Biosciences; San Diego, Calif.). Data is expressed as relative light units and are shown below in Table 1.

TABLE 1

| EC$_{50}$ values for LXR modulators in LXRβ Gal fusion assay | |
|---|---|
| Example | LXRβ Gal (EC$_{50}$) µM |
| 1 | B |
| 2 | C |
| 3 | A |
| 4 | C |
| 5 | A |
| 6 | C |
| 7 | B |
| 8 | C |
| 9 | B |
| 10 | C |
| 11 | B |
| 12 | C |
| 13 | A |
| 14 | C |
| 15 | B |
| 16 | C |

A: EC$_{50}$ < 1 µM;
B: EC$_{50}$ 1-10 µM;
C: EC$_{50}$ > 10 µM

Example A3: ABCG1 Expression

NHEKs (Cambrex/Lanza, Walkersville, Md.) are cultured as per vendor's recommendations. In general, cells were trypsinized and seeded on day 0, and treated with Compounds (1 µM) on day 1. The cells are harvested on day 2 with lysis buffer (AppliedBiosystems/Ambion, Foster City, Calif.) directly added to the cultured cells after a PBS wash. NHEKs were either used for RNA purification using Qiagen RNeasy RNA purification column (Qiagen, Hilden, Germany) as pervendor's protocol or directly processed to cDNA using "Cell-to-cDNA" lysis buffer (Ambion, Foster City, Calif.). RNA is isolated and ABCG1 gene expression analyzed by real-time PCR.

Example A4: TNFalpha Expression

NHEKs are treated and RNA extracted as described in Example A1. UV exposure of keratinocytes causes induction of TNFα expression. A reduced expression of UV-induced TNFα expression in the presence of an LXR agonist described herein indicates less activation of dermal fibroblasts, and less production of metalloproteases that degrade the dermal matrix.

Example A5: MMP3 Expression

NHEKs are treated and RNA extracted as described in Example A1. UV exposure of keratinocytes causes induction of MMP3 expression. A reduced expression of UV-induced MMP-3 expression in the presence of an LXR agonist described herein indicates reduced degradation of the dermal matrix.

Example A6: TIMP1 Expression

NHEKs are treated and RNA extracted as described in Example A1. UV exposure of keratinocytes causes reduction of the basal level of expression of TIMP1 expression. A reduced expression of UV-induced TIMP1 expression in the presence of an LXR agonist described herein is expected to neutralize the metalloprotease activities, resulting in the protection of dermal matrix from the action of MMPs.

Example A7: IL-8 Expression

NHEKs are treated and RNA extracted as described in Example A1. UV exposure of keratinocytes causes induction of IL-8 expression. Because IL-8 is a chemotactic molecule, a reduced expression of UV-induced IL-8 expression in the presence an LXR agonist described herein is expected to result in less recruitment of activated neutrophils into the dermis. Active neutrophils are also a source of MMPs and elastase that degrade the dermal matrix in photoaging.

Example A8: Synthesis of Lipids

Photoaged or photodamaged skin shows defective epidermal barrier function. ABCA12 is a lipid transporter that is essential for the maintenance and development of the epidermal barrier function of the skin. Therefore, LXR ligands may induce the synthesis of lipids and their loading into epidermal lamellar bodies by inducing the expression of lipid binding proteins and ABC transporter family members required for cholesterol and lipid efflux. These gene regulations also indicate that the LXR ligands may exhibit potent anti-xerosis therapeutic effect, thus alleviating one of the major symptoms of aged skin that leads to deterioration of epidermal barrier function and responsible for initiating other serious cutaneous conditions.

NHEK cells are treated and RNA extracted as described in Example A1. UV exposure of keratinocytes causes down-regulation of ABCA12 expression in UV-exposed keratinocytes. A reversal of the expression of UV-induced ABCA12 expression by treatment an LXR agonist described herein is expected to result in normalization of epidermal barrier function in the photoaged skin. Improved epidermal barrier function is expected to reduce skin dryness, a hallmark of photodamaged/photoaged skin. Improved epidermal barrier function is expected to reduce skin dryness, a hallmark of photodamaged/photoaged skin.

Example A9: Collagen

Photoaged and chronologically aged skin shows decreased levels of collagen. Collagen is a component of the extracellular matrix that is required for imparting rigidity to cellular as well as dermal matrix structures. Collagen molecules are arranged in the form of collagen fibrils that is required for the normal architecture of the skin. This fibrillar architecture of the collagen is degraded in aged/wrinkled skin. Therefore, restoration of the collagen fibrillar structure is also expected to result in therapeutic improvement of the photodamaged/photoaged skin.

Decorin is an extracellular matrix component that associates with collagen I. Further, decorin-collagen interaction is required for collagen fibril formation. In other words, decorin is a critical regulator of collagen 1 fibrillar-genesis. Therefore, increased decorin expression in UV-exposed photodamaged skin is expected to induce the generation of collagen fibrils, a process that may improve skin laxity and wrinkles.

NHEK cells are treated and RNA extracted as described in Example A1. UV exposure of NHEKs causes inhibition of decorin expression. A reversal of the UVB-mediated inhibition of decorin expression by treatment with an LXR agonist described herein is expected to result in normalized decorin expression in UV-exposed keratinocytes. The induction of decorin expression is expected to result in increased extracellular matrix formation.

Example A10: MMP1 Expression

The BJ cell line (ATCC # CRL-2522) is obtained from ATCC. It is a normal human fibroblast cell line originally derived from foreskin, demonstrating extended lifespan in culture of 80-90 population doublings. The cells are maintained in Eagle's Minimal Essential medium with Earle's BSS (EMEM) supplemented with penicillin-streptomycin, 1.0 mM sodium pyruvate, 0.1 mM non-essential amino acids, 2 mM GlutaMAX-1™ and 10% HyClone fetal bovine serum (FBS). With the exception of serum, all reagents are obtained from Invitrogen. The cells are subcultured with 0.05% trypsin-EDTA twice a week and maintained in a humidified incubator at 37° C. and 5% $CO_2$.

For experiments, 5 million BJ cells are plated in 150 mm dishes in growth medium. The following day, the phenol red-containing growth medium is removed and plates are rinsed once with phenol red-free EMEM without serum. Experimental medium is phenol red-free EMEM supplemented as above with the addition of 5% Lipoprotein Deficient Serum (Sigma S-5394) instead of HyClone FBS.

DMSO vehicle (0.1%) or 1 μM or an LXR agonist described herein is added to the dishes for 6 h; at which time 5 ng/ml rhTNFα (R&D 210-TA) is added to half of the treatments. Samples are harvested with TRIzol® 18 h later and processed.

RNA is extracted as described above. TNFα treatment of BJ human fibroblasts causes induction of MMP1 expression Inhibition of TNFα-induced MMP1 expression upon treatment of human fibroblasts with an LXR agonist described herein is expected to result in reduced degradation of the dermal matrix because MMP1 is the major destroyer of the dermal matrix collagen.

Example A11: MMP3 Expression

BJ cells are treated and RNA extracted as described in Example A1. TNFα treatment of BJ human fibroblasts causes induction of MMP3 expression Inhibition of TNFα-induced MMP-3 expression upon treatment of human fibroblasts with an LXR agonist described herein is expected to result in reduced degradation of the dermal matrix.

Example A12: TIMP1 Expression

BJ cells are treated and RNA extracted as described in Example A1. TNFα exposure of human BJ fibroblasts does not cause reduction of the basal level expression of TIMP1 expression. An LXR agonist described herein which induces TIMP1 expression in both TNFα-unexposed as well as TNFα-exposed fibroblasts is expected to neutralize the metalloprotease activities, resulting in the protection of dermal matrix from the action of MMPs.

Example A13: Ceramide and Lipid Second Messenger Sphingolipids Biosynthetic Pathway NHEK cells are treated and RNA is extracted as described in Example A1. Ceramide is one of the major lipids in differentiated keratinocytes and it plays a pivotal role in skin barrier function. A comparison of chronologically aged and young skin revealed a decrease in ceramide content with age. The decline in ceramide content may result from reduced keratinocyte differentiation as well as because of reduced ceramide synthase and sphingomyelin (SM) phosphodiesterase activities in chronological aging. Serine palmitoyltransferase ($SPTLC_1$) catalyzes the formation of sphinganine from serine and palmitoyl-CoA. Ceramide synthase (LASS2) converts sphinganine into ceramide. SM phosphodiesterase (SMPD) also produces ceramide from SM, and acid ceramidase (ASAH1) produces lipid second messenger sphingosine from ceramide.

An induction of the expression of enzymes involved in ceramide and lipid second messenger sphingolipids biosynthetic pathway by an LXR agonist described herein is indicative of therapeutic efficacy. Since ceramides and other sphingolipids are involved in keratinocyte proliferation, differentiation and desquamation, an increase in the expression of enzymes involved in the synthesis of sphingolipids may help in these processes and alleviate the epidermal problems (dry skin, decreased keratinocyte proliferation and differentiation, fine scales) that stem from decreased sphingolipid production.

Example A14: Antioxidant Activities in Keratinocytes

NHEK cells are treated and RNA extracted as described in Example A1. UV-mediated cumulative oxidative damage in both epidermis and dermis due to accumulation of free radicals throughout life in all likelihood also promotes cellular aging. Free radicals or reactive oxygen species cause damage to lipids, protein and DNA, and cause cells to enter a senescent-like stage. There are many reports describing the reduction of antioxidant enzymes in skin with age, including superoxide dismutase, catalase and glutathione peroxidase.

An induction of the expression of enzymes involved in the expression of enzymes involved in antioxidant activities in keratinocytes, e.g., expression of anti-oxidant enzymes, glutathione peroxidase (GPX3), thioredoxin reductase, glutathione reductase and catalase, by an LXR agonist described herein is indicative of therapeutic efficacy. LXR modulators increase the free-radical fighting defense system of the body, which may reduce the insult of hydrogen peroxide and free-radicals on skin cell proteins, lipids and DNA.

Example A15: Allergic Contact Dermatitis of the Mouse Ear

The mouse contact dermatitis model (ear edema model) has been previously used for the characterization of topical application of LXR activators for their effect on skin inflammation (Fowler et al. J Invest Dermatol 120:246 (2003)). Phorbol 12-myristate-13-acetate (PMA) is applied topically to both the inner and outer surface (10 μL each surface, 20 μL total) of the left ears to induce irritant contact dermatitis. Acetone alone (vehicle) is applied to the right ears. 30 min prior and 15 min after PMA application, 20 μL of test compounds, are applied to both surfaces of left ear (40 μL total). Identical treatments are performed with 20 μL of the positive control, 0.05% clobetasol, while the vehicle group receives acetone application alone.

After 6 h, blood samples (approximately 60 μL) are collected from retro-orbital plexus of 5 mice (from each group) at 6 h time point, into labeled micro-tubes, containing $K_2EDTA$ solution as an anticoagulant. Plasma is immediately harvested by centrifugation at 4000 rpm for 10 min at 4±2° C. and stored below −70° C. until bioanalysis. The inflammatory insult induced by PMA is assessed as the percentage increase in ear thickness and/or ear weight in the treated left ear versus the vehicle-treated right ear. Ear thickness is measured with a digital caliper followed by whole ear weight to ascertain changes in ear weights. The extent of inflammation is quantitated according to the following equation: ear swelling (%)=100×(a−b)/b, where a is the thickness/weight of the left (treated) ear and b is the thickness/weight of the right (untreated control) ear. After obtaining the samples for assessment of ear thickness/weight, biopsies are obtained from adjacent sites for routine histopathology fixation in 4% freshly prepared paraformaldehyde in phosphate-buffered saline.

Example A16: Phase II Clinical Trial of the Safety and Efficacy of Compounds of Formula (I), (II), (III), or (IV) in Patients with Mild to Moderate Chronic Plaque Psoriasis The purpose of this phase II trial is to investigate the safety and efficacy of a topical administration of a compound of Formula (I), (II), or (III) in patients with mild to moderate chronic plaque psoriasis.

Patients: Eligible subjects will be men and women 18 years of age and older.

Criteria:

Inclusion Criteria:

Mild to moderate chronic plaque psoriasis (psoriasis vulgaris), with the duration of at least 6 months;

A target plaque of at least 9 sq. cm.

Exclusion Criteria:

Demonstrates "rebound" or "flare" of chronic plaque psoriasis;

Non plaque form of psoriasis;

Currently have or history of psoriatic arthritis;

Current drug induced psoriasis;

Currently on systemic therapy or was on systemic therapy for psoriasis within the previous 6 months;

Currently on phototherapy for psoriasis or was on phototherapy within the previous 3 months.

Study Design:
Allocation: Randomized
Endpoint Classification: Safety/Efficacy Study
Intervention Model: Parallel Assignment
Masking: Double Blind (Subject, Investigator)
Primary Purpose: Treatment
Primary Outcome Measures:
Percent change from baseline at Week 4 in Target Plaque Severity Score (TPSS)
Secondary Outcome Measures:
Proportion of subjects with Treatment Area Overall Severity of Psoriasis response of "clear" (0) or "almost clear" (1) at Weeks 1, 2, 3 and 4;
Proportion of subjects with a difference from baseline of >=2 steps in Treatment Area Overall Severity of Psoriasis score at Weeks 1, 2, 3 and 4
Percent change from baseline at Weeks 1, 2, 3 and 4 in Target Plaque Area
Change from baseline at Weeks 1, 2, 3 and 4 in TPSS subscores for Erythema,
Induration and Scaling
Percent change from Baseline in TPSS at Weeks 1, 2 and 3
Actual and change from baseline on the treatment area Itch Severity Item (ISI) at Weeks 1, 2, 3 and 4
Proportion of subjects in each Patient Satisfaction with Study Medication (PSSM) response category at Week 4
Incidence, nature and severity of observed and reported administration site adverse events over 4 weeks of treatment
Incidence and severity of burning/stinging of psoriatic or perilesional skin in the treatment area over 4 weeks of treatment
Incidence and severity of reactions of perilesional skin in the treatment area as measured by Draize scoring over 4 weeks of treatment
Incidence and severity of adverse events over 4 weeks of treatment Incidence of clinical laboratory abnormalities and change from baseline in clinical laboratory values over 4 weeks of treatment
Incidence of clinically significant changes in physical examination from baseline over 4 weeks of treatment
Incidence of vital sign (blood pressure and heart rate) abnormalities and change from baseline in vital sign measures over 4 weeks of treatment
Incidence of electrocardiogram (ECG) abnormalities and change from baseline in ECG measures over 4 weeks of treatment
Plasma CP-690,550 concentrations, from blood sampling at Week 4 (Day 29)

| Arms | Assigned Interventions |
| --- | --- |
| Treatment Group A: Experimental Intervention: Drug: Compound of Formula I, IA, IB, II, IIA, IIB, III, IIIA, IIIB, IV, IVA, and IVB Ointment 1 | Drug: Compound of Formula I, IA, IB, II, IIA, IIB, III, IIIA, IIIB, IV, IVA, and IVB Ointment 1 Ointment 1 twice daily for 4 weeks |
| Treatment Group B: Placebo Comparator Intervention: Drug: Vehicle 1 | Drug: Vehicle 1 Vehicle 1 twice daily for 4 weeks |
| Treatment Group C: Experimental Intervention: Drug: Compound of Formula I, IA, IB, II, IIA, IIB, III, IIIA, IIIB, IV, IVA, and IVB Ointment 2 | Drug: Compound of Formula I, IA, IB, II, IIA, IIB, III, IIIA, IIIB, IV, IVA, and IVB Ointment 2 2% CP-690, 550 Ointment 2 twice daily for 4 weeks |
| Treatment Group D: Placebo Comparator Intervention: Drug: Vehicle 2 | Drug: Vehicle 2 Vehicle 2 twice daily for 4 weeks |

The examples and embodiments described herein are for illustrative purposes only and in some embodiments, various modifications or changes are to be included within the purview of disclosure and scope of the appended claims.

What is claimed is:

1. A compound of Formula (IA):

(IA)

wherein:
   $L_1$ and $L_2$ are each independently a bond, $C_1$-$C_6$alkyl, or $C_1$-$C_6$heteroalkyl; wherein $C_1$-$C_6$alkyl and $C_1$-$C_6$heteroalkyl are optionally substituted with at least one $R_7$;
   $R_1$ is halogen, —$CF_3$, —$OR_8$, —$N(R_8)_2$, —$C(=O)R_8$, —$C(=O)OR_8$, —$C(=O)N(R_8)_2$, —$C(=N$—$OH)R_8$, —$C(=S)N(R_8)_2$, $C_1$-$C_6$heteroalkyl, or optionally substituted $C_2$-$C_7$heterocycloalkyl;
   $R_2$ is —$C(=O)OR_9$;
   $R_3$ is hydrogen, halogen, $C_1$-$C_6$alkyl, or $C_1$-$C_6$haloalkyl;
   each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;
   each $R_8$ and each $R_{10}$ are each independently hydrogen, $C_1$-$C_6$alkyl, $C_1$-$C_6$heteroalkyl, —$C_1$-$C_6$alkyl-aryl, aryl, or heteroaryl;
   $R_9$ is $C_1$-$C_6$alkyl, $C_1$-$C_6$heteroalkyl, —$C_1$-$C_6$alkyl-aryl, aryl, or heteroaryl;
   m is 0 or 1;
   $R_{11a}$ is —$NR_{10}SO_2R_{10}$, —$SO_2R_{10}$, or —$SO_2N(R_{10})_2$;
   each $R_{11}$ is independently halogen, nitro, —$OR_{10}$, —$N(R_{10})_2$, —$CN$, —$C(=O)R_{10}$, —$C(=O)OR_{10}$, —$C(=O)N(R_{10})_2$, —$NR_{10}C(=O)R_{10}$, —$NR_{10}SO_2R_{10}$, —$SO_2R_{10}$, —$SO_2R_{10}$, —$SO_2N(R_{10})_2$, —$C(=O)OCH_2SCH_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl;
or a pharmaceutically acceptable salt thereof.

2. The compound of claim 1, wherein the compound is a compound of Formula (IB):

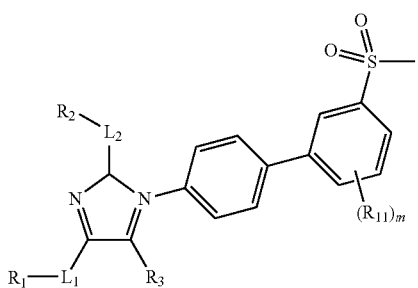

(IB)

wherein m is 0 or 1;
or a pharmaceutically acceptable salt thereof.

3. The compound of claim 1, or a pharmaceutically acceptable salt thereof, wherein:
$L_2$ is $C_1$-$C_6$alkyl;
$R_2$ is —C(=O)$OR_9$;
$R_9$ is $C_1$-$C_6$alkyl;
$L_1$ is a bond; and $R_1$ is $C_1$-$C_6$ alkyl or —$CF_3$; or
$L_1$ is $C_1$-$C_6$ alkyl; and $R_1$ is —$OR_8$;
each $R_{11}$ is independently $C_1$-$C_6$ alkyl or —$SO_2R_{10}$; wherein said $C_1$-$C_6$ alkyl is optionally substituted by 1 hydroxy;
each $R_{10}$ is independently $C_1$-$C_6$ alkyl; and
$R_3$ is hydrogen.

4. The compound of claim 1, selected from:

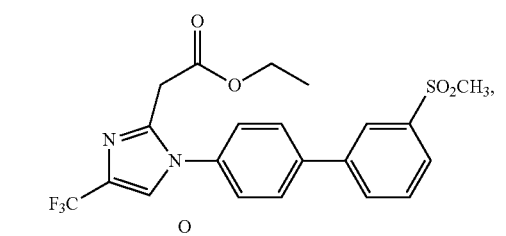

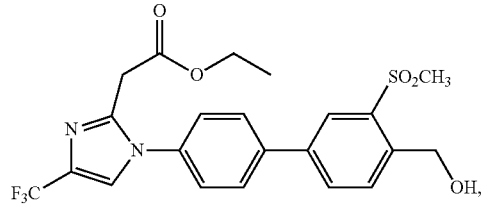

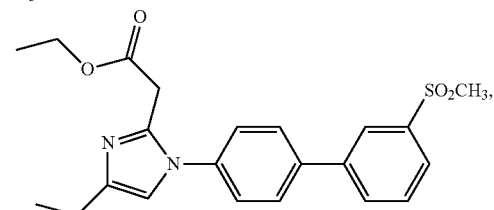

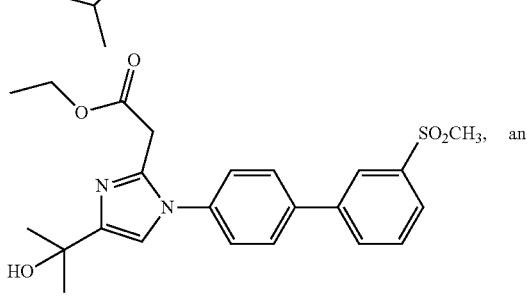

and

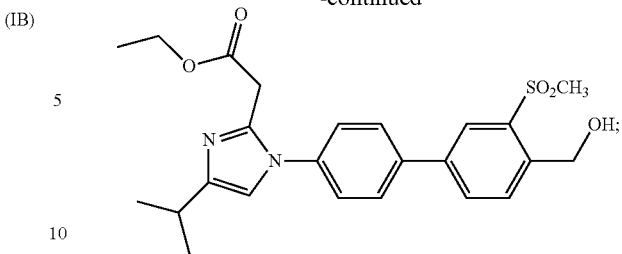

or a pharmaceutically acceptable salt thereof.

5. A compound of Formula (II):

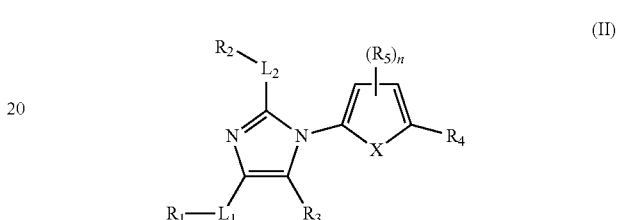

(II)

or a pharmaceutically acceptable salt thereof, wherein:
X is C($R_6$)=C($R_6$)—;
$L_1$ is a bond, $C_1$-$C_6$alkyl, or $C_1$-$C_6$heteroalkyl; wherein $C_1$-$C_6$alkyl and $C_1$-$C_6$heteroalkyl are optionally substituted with at least one $R_7$;
$L_2$ is a $C_1$-$C_6$alkyl, or $C_1$-$C_6$heteroalkyl;
$R_1$ is —C(=O)$OR_8$;
$R_2$ is hydrogen, —$OR_9$, —N($R_9$)$_2$, —C(=O)$R_9$, —C(=O)N($R_9$)$_2$, —C(=N—OH)$R_9$, —C(=S)N($R_9$)$_2$, $C_1$-$C_6$alkyl, $C_3$-$C_8$cycloalkyl, $C_1$-$C_6$haloalkyl, $C_1$-$C_6$heteroalkyl, or optionally substituted heterocycloalkyl;
$R_3$ is hydrogen, halogen, $C_1$-$C_6$alkyl, or $C_1$-$C_6$haloalkyl;
$R_4$ is aryl or heteroaryl; wherein aryl and heteroaryl are substituted with at least one $R_{11}$;
each $R_5$ is independently halogen, $C_1$-$C_6$alkyl, or $C_1$-$C_6$haloalkyl;
each $R_6$ is independently hydrogen, halogen, $C_1$-$C_6$alkyl, or $C_1$-$C_6$haloalkyl;
each $R_7$ is independently $C_1$-$C_6$alkyl, $C_3$-$C_8$cycloalkyl, $C_1$-$C_6$haloalkyl, $C_1$-$C_6$heteroalkyl, —$C_1$-$C_6$alkyl-aryl, optionally substituted aryl, or optionally substituted heteroaryl;
each $R_9$ and each $R_{10}$ are each independently hydrogen, $C_1$-$C_6$alkyl, $C_1$-$C_6$heteroalkyl, —$C_1$-$C_6$alkyl-aryl, aryl, or heteroaryl;
each $R_8$ is $C_1$-$C_6$alkyl, $C_1$-$C_6$heteroalkyl, —$C_1$-$C_6$alkyl-aryl, aryl, or heteroaryl;
each $R_{11}$ is independently halogen, nitro, —$OR_{10}$, —N($R_{10}$)$_2$, —CN, —C(=O)$R_{10}$, —C(=O)$OR_{10}$, —C(=O)N($R_{10}$)$_2$, —$NR_{10}$C(=O)$R_{10}$, —$NR_{10}SO_2R_{10}$, —$SOR_{10}$, —$SO_2R_{10}$, —$SO_2$N($R_{10}$)$_2$, —C(=O)$OCH_2SCH_3$, optionally substituted $C_1$-$C_6$alkyl, optionally substituted $C_3$-$C_8$cycloalkyl, optionally substituted $C_1$-$C_6$haloalkyl, optionally substituted $C_1$-$C_6$heteroalkyl, optionally substituted —$C_1$-$C_6$alkyl-aryl, optionally substituted aryl, or optionally substituted heteroaryl; and
n is 0-2.

6. The compound of claim 5, wherein the compound is a compound of Formula (IIB):

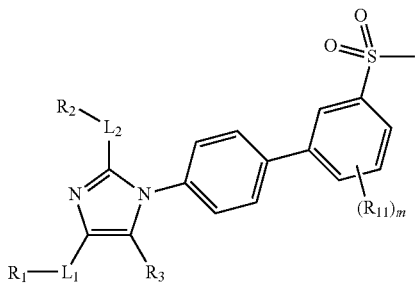

(IIB)

wherein m is 0 or 1;
or a pharmaceutically acceptable salt thereof.

7. The compound of claim 5, or a pharmaceutically acceptable salt thereof, wherein:
X is —CH=CH—;
$R_1$ is a —C(=O)O$R_8$; and $R_8$ is $C_1$-$C_6$alkyl;
$L_2$ is $C_1$-$C_6$alkyl;
$R_2$ is hydrogen;
$R_4$ is phenyl substituted with at least one $R_{11}$;
each $R_{11}$ is independently $C_1$-$C_6$ alkyl or -$SO_2R_{10}$; wherein said $C_1$-$C_6$ alkyl is optionally substituted by 1 hydroxy;
provided that at least one $R_{11}$ is —$SO_2R_{10}$;
each $R_{10}$ is independently $C_1$-$C_6$ alkyl;
n is 0; and
$R_3$ is hydrogen.

8. The compound of claim 5, selected from:

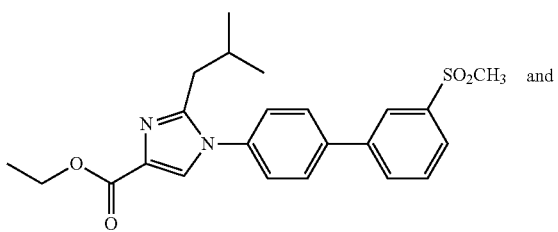

and

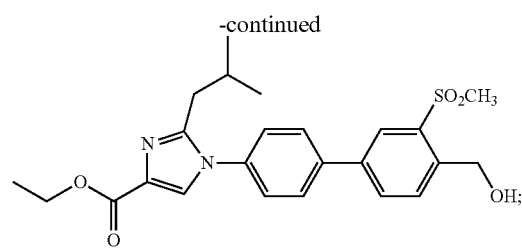

or a pharmaceutically acceptable salt thereof.

9. A pharmaceutical composition comprising a compound of claim 1, or a pharmaceutically acceptable salt thereof, and a pharmaceutically acceptable carrier.

10. A method of treating a dermal disease, disorder or condition selected from skin aging, psoriasis, and dermatitis comprising administering to the mammal a compound according to claim 1, or a pharmaceutically acceptable salt thereof.

11. A method of agonizing LXR activity comprising contacting LXR, or portion thereof, with a compound according to claim 1, or a pharmaceutically acceptable salt thereof.

12. A pharmaceutical composition comprising a compound of claim 5, or a pharmaceutically acceptable salt thereof, and a pharmaceutically acceptable carrier.

13. A method of treating a dermal disease, disorder or condition selected from skin aging, psoriasis, and dermatitis comprising administering to the mammal a compound according to claim 5, or a pharmaceutically acceptable salt thereof.

14. A method of agonizing LXR activity comprising contacting LXR, or portion thereof, with a compound according to claim 5, or a pharmaceutically acceptable salt thereof.

* * * * *

UNITED STATES PATENT AND TRADEMARK OFFICE
CERTIFICATE OF CORRECTION

PATENT NO. : 9,981,913 B2
APPLICATION NO. : 14/916292
DATED : May 29, 2018
INVENTOR(S) : Raju Mohan Page 1 of 1

It is certified that error appears in the above-identified patent and that said Letters Patent is hereby corrected as shown below:

On the Title Page

Column 1, item (*) Notice, Line 3, after "0 days." delete "days."

In the Claims

Column 122, Line 36, Claim 1, after "-C(=S)N($R_8$)$_2$," insert -- $C_1$-$C_6$alkyl, --

Column 122, Line 53, Claim 1, after "-$NR_{10}SO_2R_{10}$," insert -- -$SOR_{10}$, --

Column 122, Line 57, Claim 1, delete "-$SO_2R_{10}$, -$SO_2R_{10}$," and insert -- -$SOR_{10}$, -$SO_2R_{10}$, --

Column 122, Line 67, Claim 2, delete "(TB):" and insert -- (IB): --

Column 125, Line 25, Claim 7, delete "or-$SO_2R_{10}$;" and insert -- or -$SO_2R_{10}$; --

Signed and Sealed this
Seventh Day of August, 2018

Andrei Iancu
*Director of the United States Patent and Trademark Office*